US008545486B2

(12) United States Patent
Malkowski

(10) Patent No.: US 8,545,486 B2
(45) Date of Patent: Oct. 1, 2013

(54) SURGICAL CLIP APPLIER

(75) Inventor: Jaroslaw T. Malkowski, Trumbull, CT (US)

(73) Assignee: Covidien LP, Mansfield, MA (US)

(*) Notice: Subject to any disclaimer, the term of this patent is extended or adjusted under 35 U.S.C. 154(b) by 500 days.

(21) Appl. No.: 12/943,045

(22) Filed: Nov. 10, 2010

(65) Prior Publication Data

US 2011/0144665 A1 Jun. 16, 2011

Related U.S. Application Data

(60) Provisional application No. 61/286,569, filed on Dec. 15, 2009.

(51) Int. Cl.
*A61B 17/00* (2006.01)

(52) U.S. Cl.
USPC .................................................. 606/1

(58) Field of Classification Search
None
See application file for complete search history.

(56) References Cited

U.S. PATENT DOCUMENTS

| 3,120,230 | A | 2/1964 | Skold |
| 3,638,847 | A | 2/1972 | Noiles et al. |
| 4,242,902 | A | 1/1981 | Green |
| 4,296,751 | A | 10/1981 | Blake, III et al. |
| 4,372,316 | A | 2/1983 | Blake, III et al. |
| 4,408,603 | A | 10/1983 | Blake, III et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A | 4/1985 | McGarry et al. |
| 4,512,345 | A | 4/1985 | Green |
| 4,522,207 | A | 6/1985 | Klieman et al. |
| 4,532,925 | A | 8/1985 | Blake, III |

(Continued)

FOREIGN PATENT DOCUMENTS

| EP | 0 085 931 A2 | 8/1983 |
| EP | 0 089 737 A1 | 9/1983 |

(Continued)

OTHER PUBLICATIONS

The extended European Search Report corresponding to European Application No. EP 11250214.1, completed May 25, 2011; mailed Jun. 1, 2011; (3 Pages).

(Continued)

*Primary Examiner* — Melanie Tyson
*Assistant Examiner* — Son Dang

(57) ABSTRACT

Surgical clip appliers are provided and include a housing; at least one handle pivotably connected to the housing; a channel assembly extending distally from the housing; a clip carrier disposed within the channel assembly and defining a channel and a plurality of windows therein; and a plurality of clips slidably disposed within the channel of the clip carrier. The surgical clip appliers further include a drive channel reciprocally disposed within at least one of the housing and the channel assembly; a wedge plate reciprocally disposed within the channel assembly; a pusher bar reciprocally positioned within the housing and the channel assembly; and a motion multiplier system having a plurality of linkage members configured to distally move the pusher bar by an incremental amount upon an initial actuation of the handles, and configured to proximally move the pusher bar and the wedge plate subsequent to the initial actuation of the handles.

18 Claims, 42 Drawing Sheets

(56) References Cited

U.S. PATENT DOCUMENTS

| | | |
|---|---|---|
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |

| Patent | Date | Inventor |
|---|---|---|
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B2 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |

| | | | | | | |
|---|---|---|---|---|---|---|
| 6,837,893 B2 | 1/2005 | Miller | | 2002/0128668 A1 | 9/2002 | Manetakis et al. |
| 6,837,894 B2 | 1/2005 | Pugsley, Jr. et al. | | 2002/0177859 A1 | 11/2002 | Monassevitch et al. |
| 6,837,895 B2 | 1/2005 | Mayenberger | | 2002/0198537 A1 | 12/2002 | Smith et al. |
| 6,840,945 B2 | 1/2005 | Manetakis et al. | | 2002/0198538 A1 | 12/2002 | Kortenbach et al. |
| 6,843,794 B2 | 1/2005 | Sixto, Jr. et al. | | 2002/0198539 A1 | 12/2002 | Sixto, Jr. et al. |
| 6,849,078 B2 | 2/2005 | Durgin et al. | | 2002/0198540 A1 | 12/2002 | Smith et al. |
| 6,849,079 B1 | 2/2005 | Blake, III et al. | | 2002/0198541 A1 | 12/2002 | Smith et al. |
| 6,853,879 B2 | 2/2005 | Sunaoshi | | 2003/0014060 A1 | 1/2003 | Wilson, Jr. et al. |
| 6,869,435 B2 | 3/2005 | Blake, III | | 2003/0018345 A1 | 1/2003 | Green |
| 6,869,436 B2 | 3/2005 | Wendlandt | | 2003/0023249 A1 | 1/2003 | Manetakis |
| 6,889,116 B2 | 5/2005 | Jinno | | 2003/0040759 A1 | 2/2003 | de Guillebon et al. |
| 6,896,682 B1 | 5/2005 | McClellan et al. | | 2003/0105476 A1 | 6/2003 | Sancoff et al. |
| 6,905,503 B2 | 6/2005 | Gifford, III et al. | | 2003/0114867 A1 | 6/2003 | Bolduc et al. |
| 6,911,032 B2 | 6/2005 | Jugenheimer et al. | | 2003/0135224 A1 | 7/2003 | Blake, III |
| 6,911,033 B2 | 6/2005 | de Guillebon et al. | | 2003/0167063 A1 | 9/2003 | Kerr |
| 6,913,607 B2 | 7/2005 | Ainsworth et al. | | 2003/0225423 A1 | 12/2003 | Huitema |
| 6,916,327 B2 | 7/2005 | Northrup, III et al. | | 2003/0233105 A1 | 12/2003 | Gayton |
| 6,923,818 B2 | 8/2005 | Muramatsu et al. | | 2004/0010272 A1 | 1/2004 | Manetakis et al. |
| 6,939,356 B2 | 9/2005 | Debbas | | 2004/0097970 A1 | 5/2004 | Hughett |
| 6,942,674 B2 | 9/2005 | Belef et al. | | 2004/0097971 A1 | 5/2004 | Hughett |
| 6,942,676 B2 | 9/2005 | Buelna | | 2004/0138681 A1 | 7/2004 | Pier |
| 6,945,978 B1 | 9/2005 | Hyde | | 2004/0153100 A1 | 8/2004 | Ahlberg et al. |
| 6,945,979 B2 | 9/2005 | Kortenbach et al. | | 2005/0080440 A1 | 4/2005 | Durgin et al. |
| 6,949,107 B2 | 9/2005 | McGuckin, Jr. et al. | | 2005/0085830 A1 | 4/2005 | Lehman et al. |
| 6,953,465 B2 | 10/2005 | Dieck et al. | | 2005/0090837 A1 | 4/2005 | Sixto, Jr. et al. |
| 6,955,643 B2 | 10/2005 | Gellman et al. | | 2005/0090838 A1 | 4/2005 | Sixto et al. |
| 6,959,852 B2 | 11/2005 | Shelton, IV et al. | | 2005/0096670 A1 | 5/2005 | Wellman et al. |
| 6,960,218 B2 | 11/2005 | Rennich | | 2005/0096671 A1 | 5/2005 | Wellman et al. |
| 6,960,221 B2 | 11/2005 | Ho et al. | | 2005/0096672 A1 | 5/2005 | Manetakis et al. |
| 6,962,594 B1 | 11/2005 | Thevenet | | 2005/0101975 A1 | 5/2005 | Nguyen et al. |
| 6,963,792 B1 | 11/2005 | Green | | 2005/0107807 A1 | 5/2005 | Nakao |
| 6,964,363 B2 | 11/2005 | Wales et al. | | 2005/0107809 A1 | 5/2005 | Litscher et al. |
| 6,964,668 B2 | 11/2005 | Modesitt et al. | | 2005/0107810 A1 | 5/2005 | Morales et al. |
| 6,966,875 B1 | 11/2005 | Longobardi | | 2005/0107811 A1 | 5/2005 | Starksen et al. |
| 6,966,917 B1 | 11/2005 | Suyker et al. | | 2005/0107812 A1 | 5/2005 | Starksen et al. |
| 6,966,919 B2 | 11/2005 | Sixto, Jr. et al. | | 2005/0107871 A1 | 5/2005 | Realyvasquez et al. |
| 6,969,391 B1 | 11/2005 | Gazzani | | 2005/0113847 A1 | 5/2005 | Gadberry et al. |
| 6,972,023 B2 | 12/2005 | Whayne et al. | | 2005/0119671 A1 | 6/2005 | Reydel et al. |
| 6,972,027 B2 | 12/2005 | Fallin et al. | | 2005/0119673 A1 | 6/2005 | Gordon et al. |
| 6,973,770 B2 | 12/2005 | Schnipke et al. | | 2005/0119677 A1 | 6/2005 | Shipp |
| 6,974,462 B2 | 12/2005 | Sater | | 2005/0125010 A1 | 6/2005 | Smith et al. |
| 6,974,466 B2 | 12/2005 | Ahmed et al. | | 2005/0143767 A1 | 6/2005 | Kimura et al. |
| 6,974,475 B1 | 12/2005 | Wall | | 2005/0149063 A1 | 7/2005 | Young et al. |
| 6,981,505 B2 | 1/2006 | Krause et al. | | 2005/0149064 A1 | 7/2005 | Peterson et al. |
| 6,981,628 B2 | 1/2006 | Wales | | 2005/0149068 A1 | 7/2005 | Williams et al. |
| 6,991,635 B2 | 1/2006 | Takamoto et al. | | 2005/0149069 A1 | 7/2005 | Bertolero et al. |
| 7,052,504 B2 | 5/2006 | Hughett | | 2005/0165415 A1 | 7/2005 | Wales |
| 7,056,330 B2 | 6/2006 | Gayton | | 2005/0165418 A1 | 7/2005 | Chan |
| 7,108,703 B2 | 9/2006 | Danitz et al. | | 2005/0171560 A1 | 8/2005 | Hughett |
| 7,144,402 B2 | 12/2006 | Kuester, III | | 2005/0177176 A1 | 8/2005 | Gerbi et al. |
| 7,175,648 B2 | 2/2007 | Nakao | | 2005/0177177 A1 | 8/2005 | Viola |
| 7,179,265 B2 | 2/2007 | Manetakis et al. | | 2005/0203547 A1 | 9/2005 | Weller et al. |
| 7,207,997 B2 | 4/2007 | Shipp et al. | | 2005/0203548 A1 | 9/2005 | Weller et al. |
| 7,211,091 B2 | 5/2007 | Fowler et al. | | 2005/0216036 A1 | 9/2005 | Nakao |
| 7,211,092 B2 | 5/2007 | Hughett | | 2005/0216056 A1 | 9/2005 | Valdevit et al. |
| 7,214,230 B2 | 5/2007 | Brock et al. | | 2005/0222588 A1 | 10/2005 | Vandenbroek et al. |
| 7,214,232 B2 | 5/2007 | Bowman et al. | | 2005/0222590 A1 | 10/2005 | Gadberry et al. |
| 7,223,271 B2 | 5/2007 | Muramatsu et al. | | 2005/0222665 A1 | 10/2005 | Aranyi |
| 7,223,272 B2 | 5/2007 | Francese et al. | | 2005/0228411 A1 | 10/2005 | Manzo |
| 7,232,445 B2 | 6/2007 | Kortenbach et al. | | 2005/0228416 A1 | 10/2005 | Burbank et al. |
| 7,261,724 B2 | 8/2007 | Molitor et al. | | 2005/0234478 A1 | 10/2005 | Wixey et al. |
| 7,261,725 B2 | 8/2007 | Binmoeller | | 2005/0251183 A1 | 11/2005 | Buckman et al. |
| 7,264,625 B1 | 9/2007 | Buncke | | 2005/0251184 A1 | 11/2005 | Anderson |
| 7,288,098 B2 | 10/2007 | Huitema et al. | | 2005/0256529 A1 | 11/2005 | Yawata et al. |
| 7,297,149 B2 | 11/2007 | Vitali et al. | | 2005/0267495 A1 | 12/2005 | Ginn et al. |
| 7,316,693 B2 | 1/2008 | Viola | | 2005/0273122 A1 | 12/2005 | Theroux et al. |
| 7,316,696 B2 | 1/2008 | Wilson, Jr. et al. | | 2005/0277951 A1 | 12/2005 | Smith et al. |
| 7,326,223 B2 | 2/2008 | Wilson, Jr. | | 2005/0277952 A1 | 12/2005 | Arp et al. |
| 7,329,266 B2 | 2/2008 | Royse et al. | | 2005/0277953 A1 | 12/2005 | Francese et al. |
| 7,331,968 B2 | 2/2008 | Arp et al. | | 2005/0277954 A1 | 12/2005 | Smith et al. |
| 7,338,503 B2 | 3/2008 | Rosenberg et al. | | 2005/0277955 A1 | 12/2005 | Palmer et al. |
| 7,357,805 B2 | 4/2008 | Masuda et al. | | 2005/0277957 A1 | 12/2005 | Francese et al. |
| 2001/0047178 A1 | 11/2001 | Peters | | 2005/0277958 A1 | 12/2005 | Levinson |
| 2002/0068947 A1 | 6/2002 | Kuhns et al. | | 2005/0288689 A1 | 12/2005 | Kammerer et al. |
| 2002/0082618 A1 | 6/2002 | Shipp et al. | | 2005/0288690 A1 | 12/2005 | Bourque et al. |
| 2002/0087169 A1 | 7/2002 | Brock et al. | | 2006/0004388 A1 | 1/2006 | Whayne et al. |
| 2002/0087170 A1 | 7/2002 | Kuhns et al. | | 2006/0004390 A1 | 1/2006 | Rosenberg et al. |
| 2002/0099388 A1 | 7/2002 | Mayenberger | | 2006/0009789 A1 | 1/2006 | Gambale et al. |
| 2002/0120279 A1 | 8/2002 | Deguillebon et al. | | 2006/0009790 A1 | 1/2006 | Blake et al. |

| | | |
|---|---|---|
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1 | 10/2008 | Whitfield et al. |
| 2010/0274262 A1 | 10/2010 | Schulz et al. |

FOREIGN PATENT DOCUMENTS

| | | |
|---|---|---|
| EP | 0 324 166 A2 | 7/1989 |
| EP | 0 392 750 A1 | 10/1990 |
| EP | 0 409 569 A1 | 1/1991 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 191 A2 | 10/2006 |
| EP | 1 813 199 A1 | 8/2007 |
| EP | 1 908 423 A2 | 4/2008 |
| EP | 1 913 881 A1 | 4/2008 |
| EP | 2 229 895 A1 | 9/2010 |
| JP | 2003 033361 A | 2/2003 |
| WO | WO 2005/091457 A1 | 9/2005 |
| WO | WO 2006/042076 A2 | 4/2006 |
| WO | WO 2006/042084 A2 | 4/2006 |
| WO | WO 2006/042110 A2 | 4/2006 |
| WO | WO 2008/118928 A2 | 10/2008 |
| WO | WO 2008/127968 A2 | 10/2008 |

OTHER PUBLICATIONS

The extended International Search Report corresponding to European Application No. 07 25 3905.9, completed Jan. 29, 2008; mailed Feb. 7, 2008; (7 Pages).

The partial International Search Report corresponding to European Application No. EP 07 25 3807.7, completed Jul. 23, 2008; mailed Aug. 1, 2008; (3 pages).

International Search Report corresponding to International Application No. PCT/US08/58185, completed Sep. 4, 2008; mailed Sep. 9, 2008; (2 Pages).

The International Search Report corresponding to International Application No. PCT/US08/59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

The extended European Search Report corresponding to European Application No. EP 09252049.3, completed Dec. 11, 2009; mailed Jan. 12, 2010; (3 Pages).

The extended European Search Report corresponding to European Application No. EP 09252050.1, completed Dec. 23, 2009; mailed Jan. 21, 2010; (3 Pages).

The extended European Search Report corresponding to European Application No. EP 09252051.9, completed Dec. 21, 2009; mailed Jan. 28, 2010; (3 Pages).

The extended European Search Report corresponding to European Application No. EP 09252052.7, completed Nov. 16, 2009; mailed Nov. 24, 2009; (3 Pages).

The extended European Search Report corresponding to European Application No. EP 09252053.5, completed Nov. 24, 2009; mailed Dec. 1, 2009; (3 Pages).

The extended European Search Report corresponding to European Application No. EP 09252054.3, completed Jan. 7, 2010; mailed Jan. 22, 2010; (3 Pages).

Extended European Search Report corresponding to European Application No. EP 09252056.8, completed Jan. 8, 2010; mailed Feb. 5. 2010; (3 Pages).

Extended European Search Report corresponding to European Application No. EP 10250497.4, completed May 4, 2010; mailed May 12, 2010; (6 Pages).

"Salute II Disposable Fixation Device", Technique Guide—Laparoscopic and Open Inguinal and Ventral Hernia Repair; Davol, A Bard Company, 2006; (7 Pages).

The extended European Search Report corresponding to European Application No. EP 12 18 6401.1, completed Nov. 22, 2012 and mailed Nov. 30, 2012; (7 Pages).

The extended European Search Report corresponding to European Application No. EP 12 18 6448.2, completed Nov. 28, 2012 and mailed Dec. 10, 2012; (6 Pages).

The extended European Search Report corresponding to European Application No. EP 12 19 1706.6, completed Dec. 19, 2012 and mailed Jan. 8, 2013; (6 Pages).

The extended European Search Report corresponding to European Application No. EP 11 25 0754.6, completed Oct. 22, 2012 and mailed Oct. 31, 2012; (6 Pages).

European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

Extended European Search Report corresponding to EP 10252079.8, date of mailing is Mar. 17, 2011; date of completion of Search is Mar. 8, 2011 (3 Pages).

European Search Report corresponding to EP 05810218.7, mailed on May 20, 2011; completed on Apr. 18, 2011; 3 pages.

European Search Report corresponding to EP 05807612.6, mailed on May 20, 2011; completed on May 2, 2011; 3 pages.

Extended European Search Report corresponding to EP 10251737.2, mailed on May 20, 2011; completed on May 9, 2011; 4 pages.

The extended European Search Report corresponding to European Application No. EP 12 16 2288.0, completed Jun. 4, 2012 and mailed Jul. 7, 2012; (6 Pages).

The extended European Search Report corresponding to European Application No. EP 12 16 5891.8, completed Jun. 12, 2012 and mailed Jun. 20, 2012; (6 Pages).

The extended European Search Report corresponding to European Application No. EP 12 16 4955.2, completed Aug. 23, 2012 and mailed Sep. 4, 2012; (5 Pages).

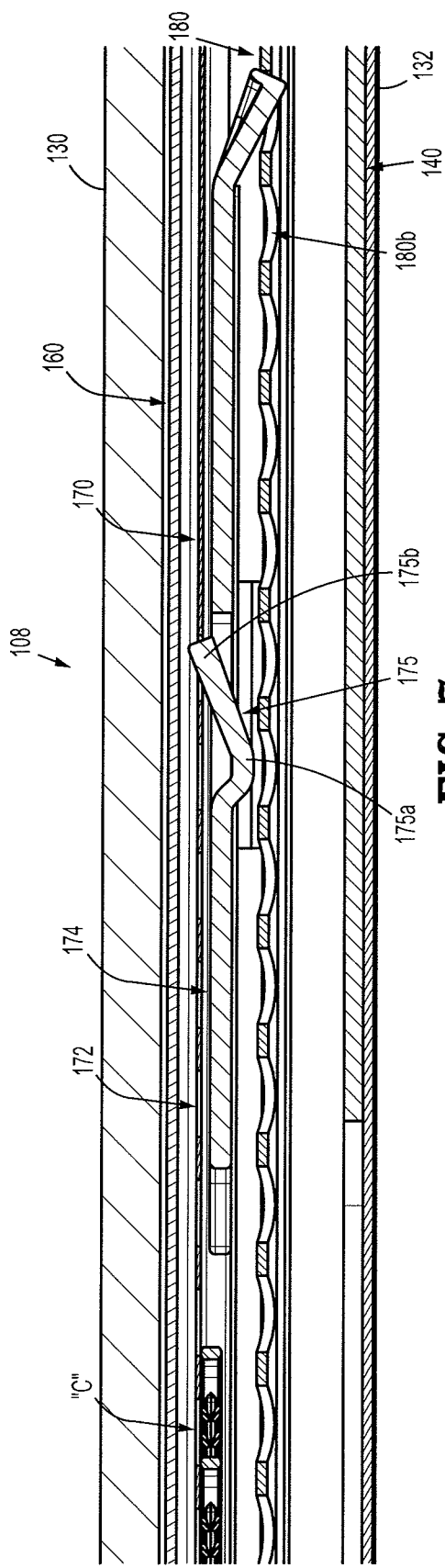
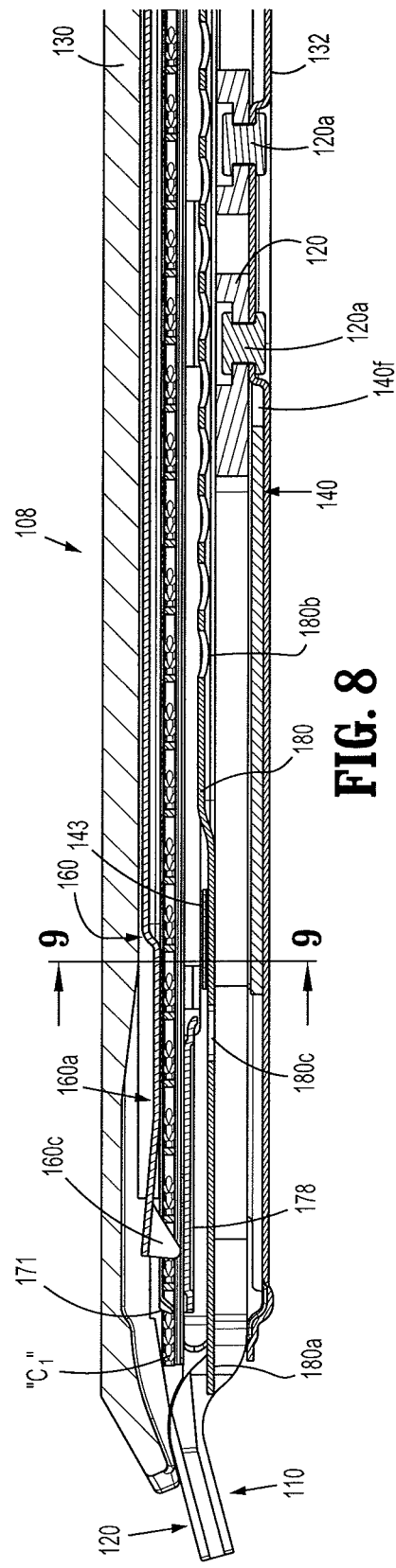
FIG. 7
FIG. 8

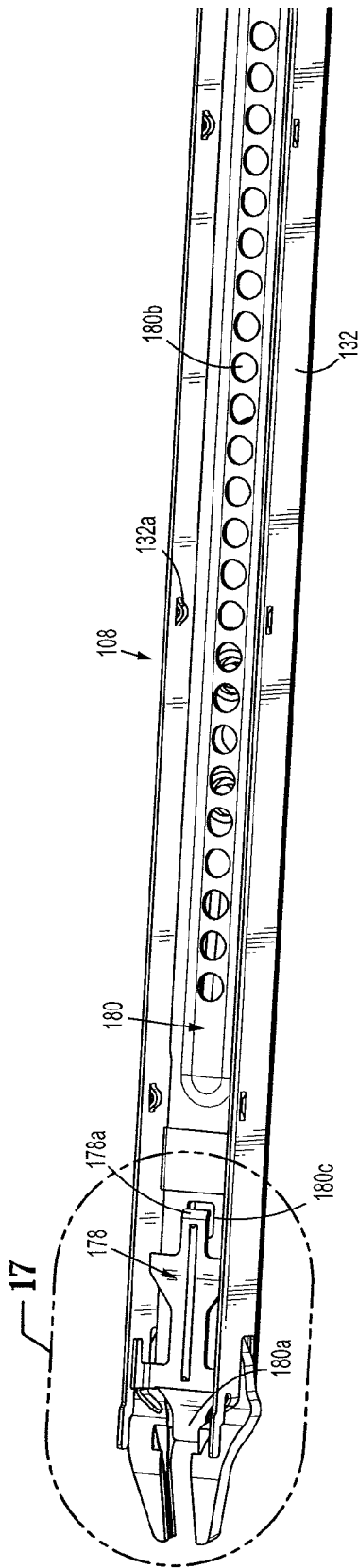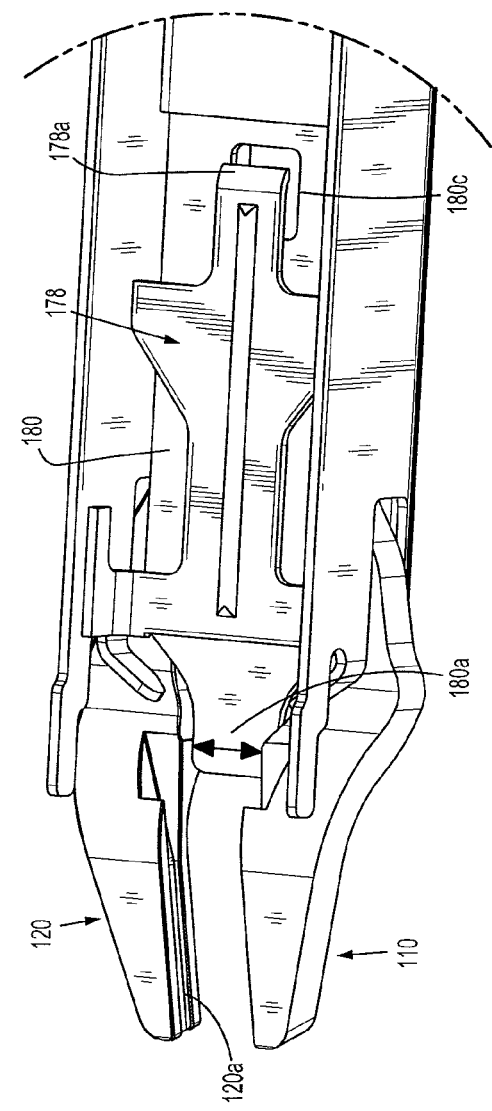
FIG. 16
FIG. 17

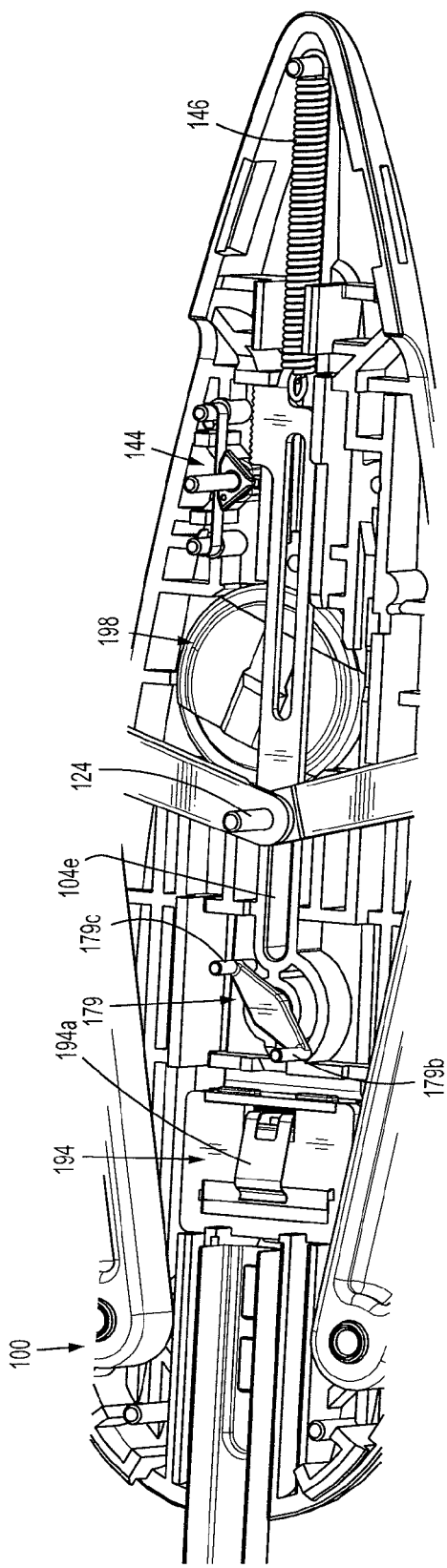
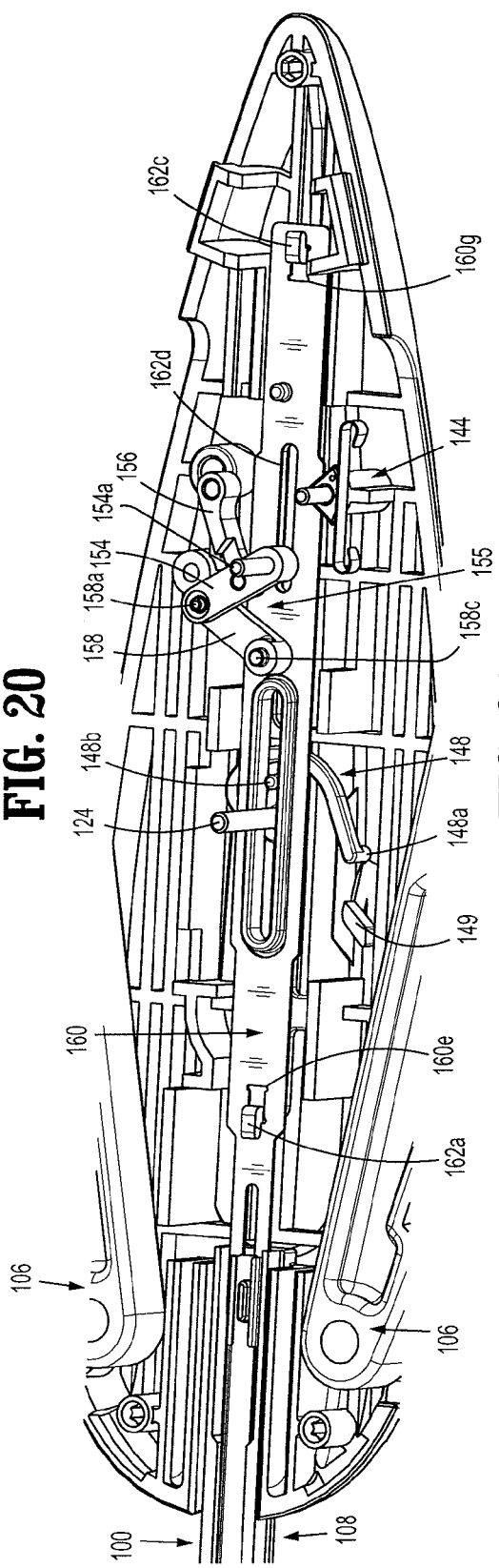
FIG. 20
FIG. 21

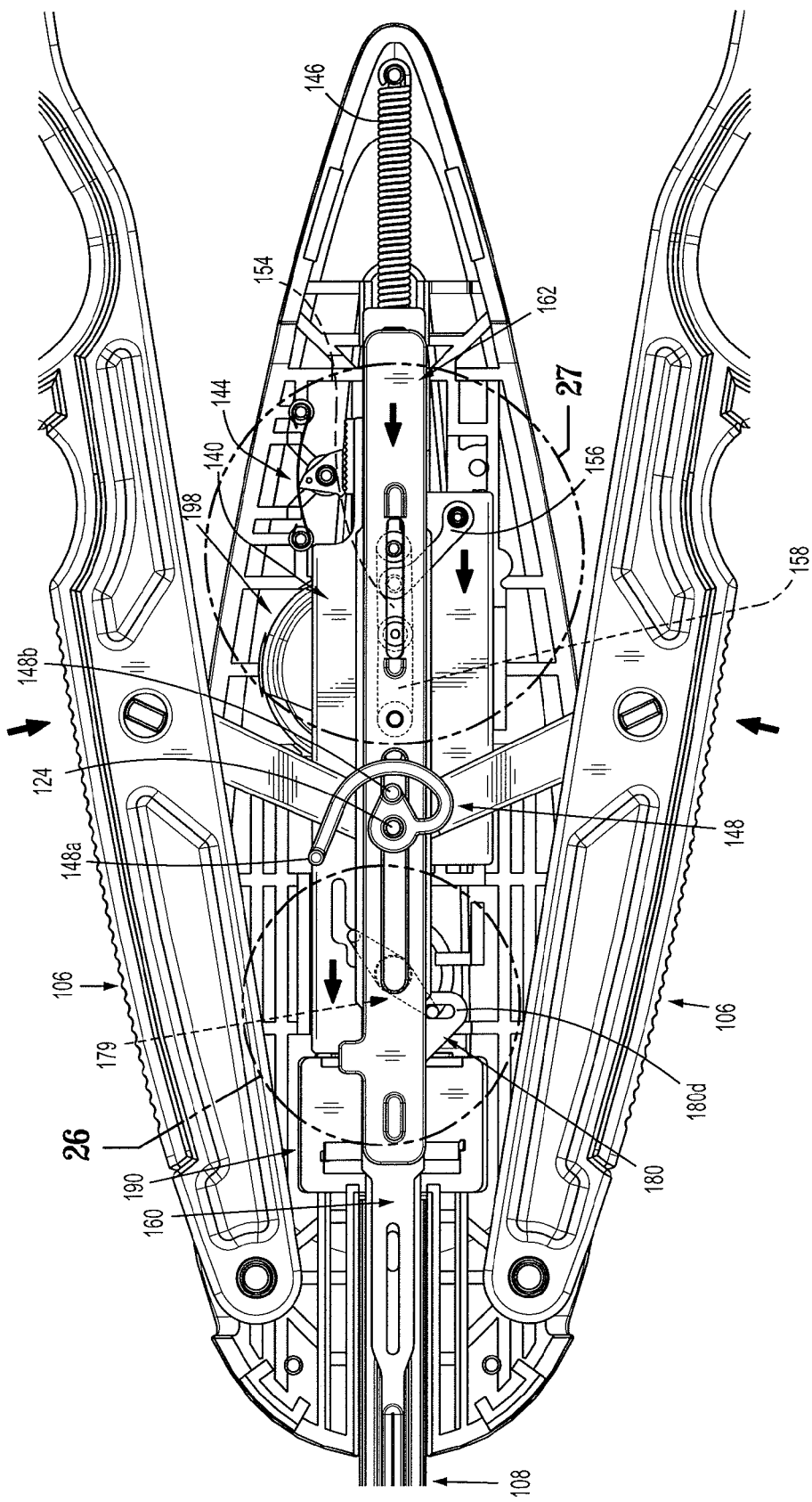

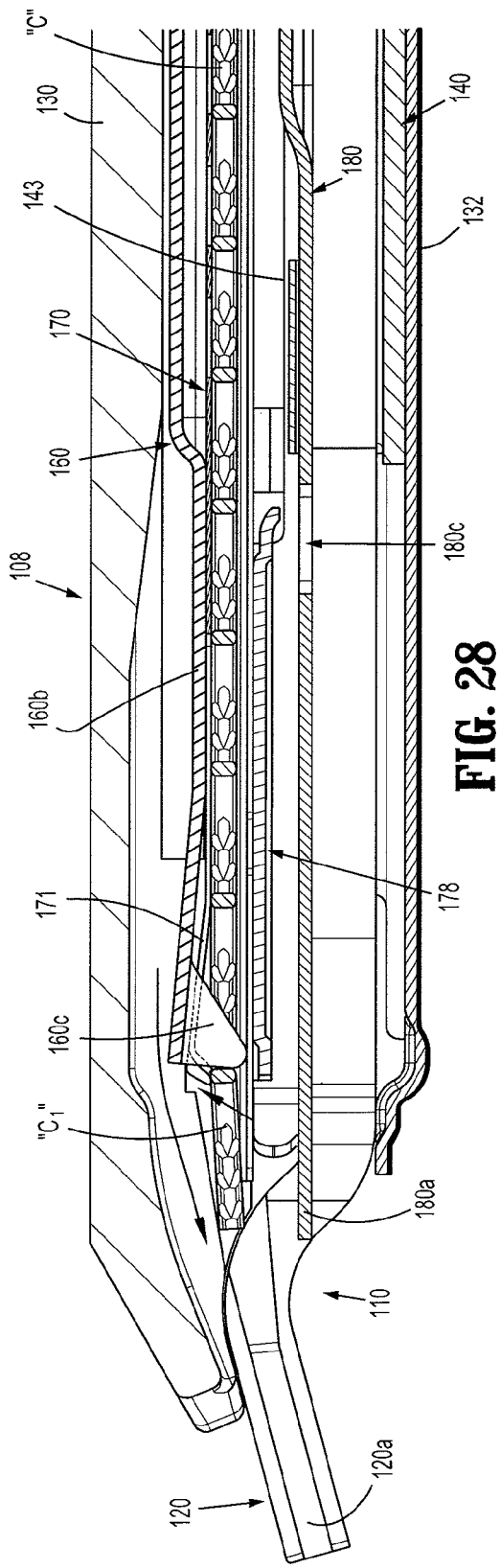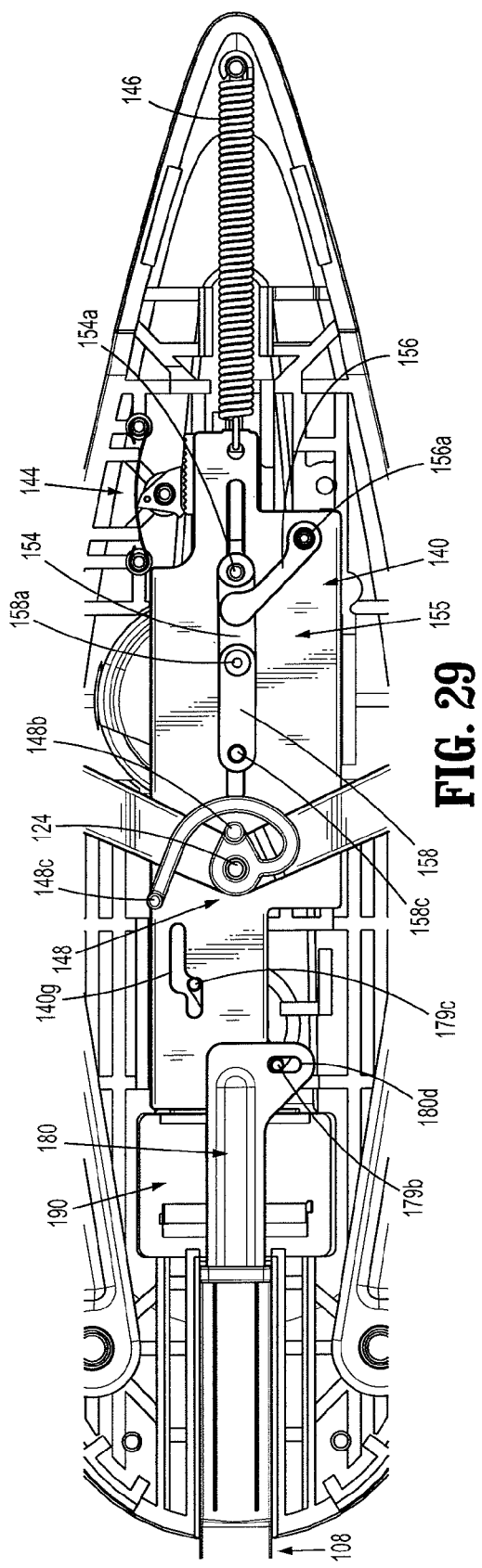

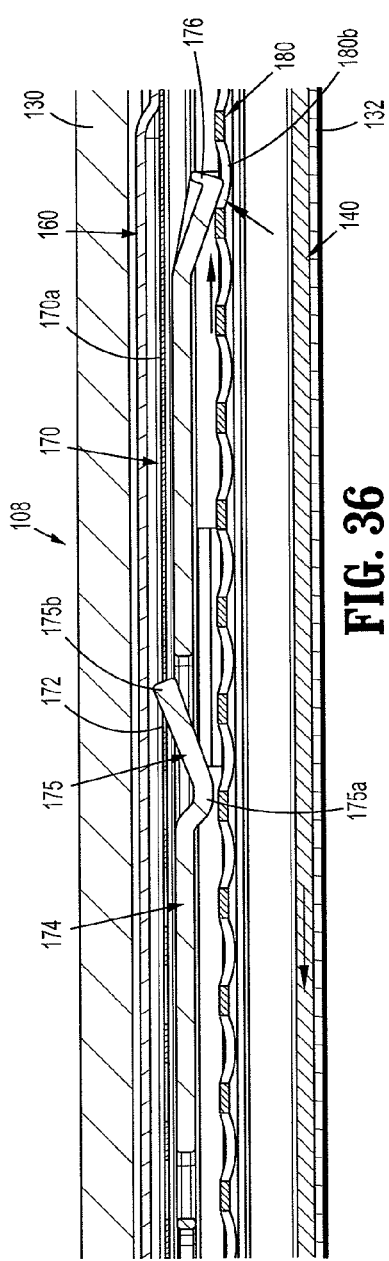
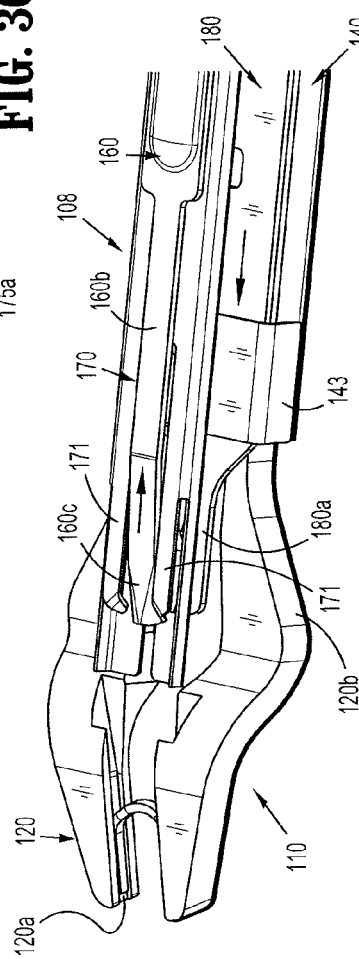
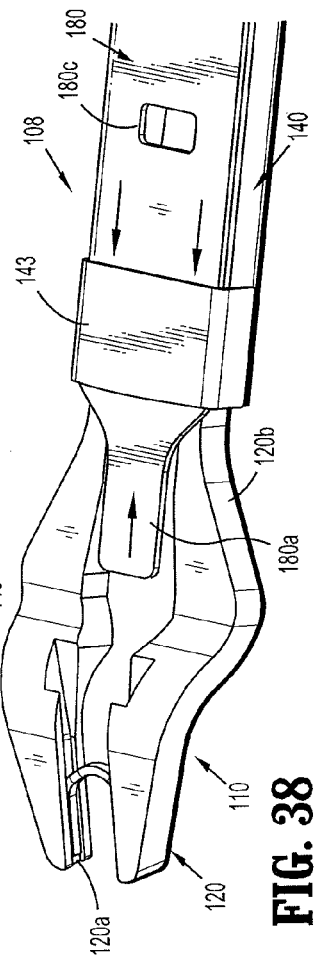
FIG. 36
FIG. 37
FIG. 38

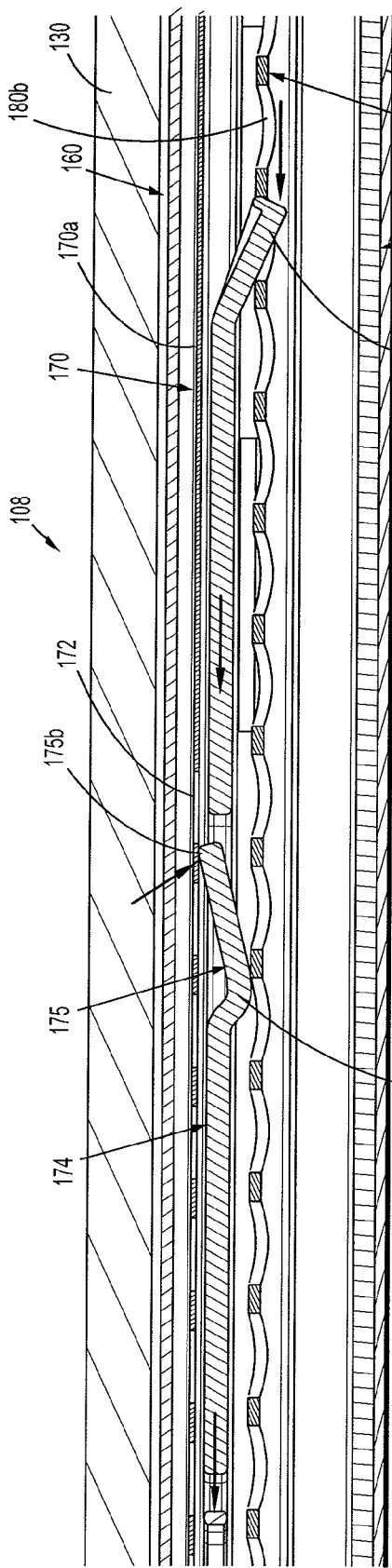
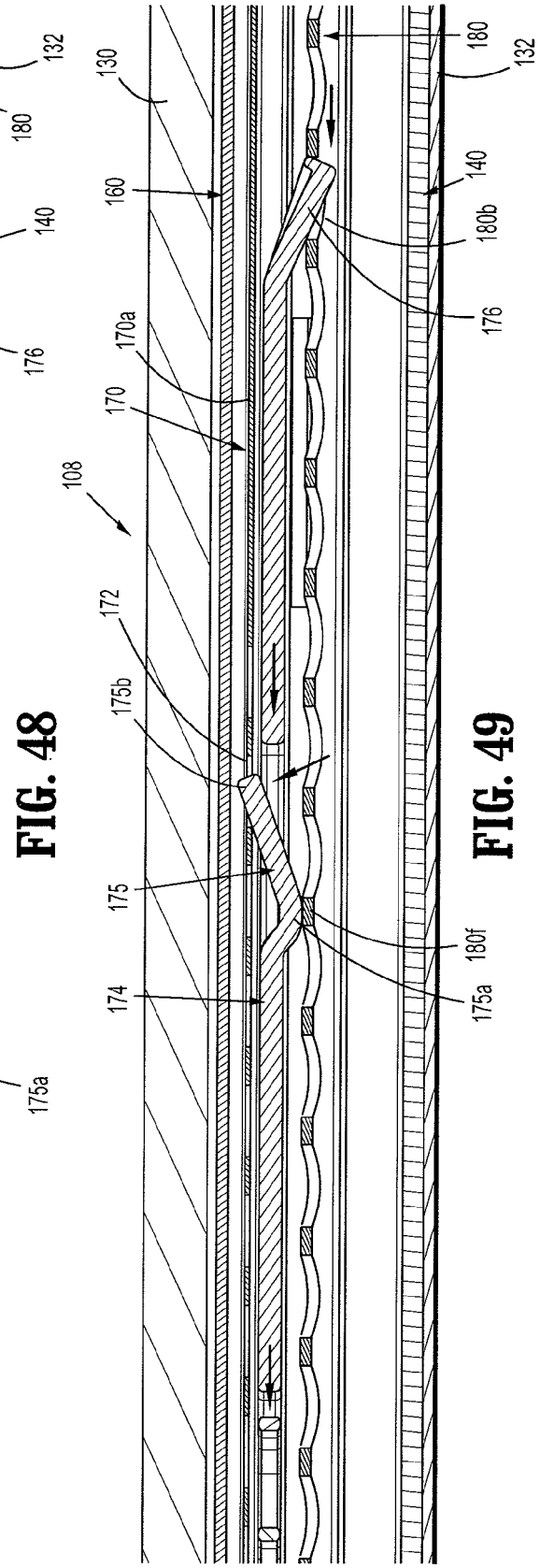
FIG. 48
FIG. 49

SURGICAL CLIP APPLIER

CROSS REFERENCE TO RELATED APPLICATION

The present application claims the benefit of and priority to U.S. Provisional Application Ser. No. 61/286,569, filed on Dec. 15, 2009, the entire content of which is incorporate herein by reference.

BACKGROUND

1. Technical Field

The present application relates to surgical instruments, and more particularly, to surgical clip appliers having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Surgical clip appliers are typically available in a variety of sizes and/or scales ranging from relatively small, relatively medium to relatively large. Generally, each particular size of surgical clip appliers includes different components. As such, the method of assembling the various sized surgical clip appliers differs from one size to another.

As a consequence, each different size clip applier requires a different stroke length of external components (e.g., clip applier actuation) that, in turn, affects different timing of internal components (e.g., clip deployment components). The need therefore exists where certain essential components can be configured for each different sized clip applier by only changing geometry without changing functionality.

In addition, the need therefore exists for a surgical clip applier that is configured to accommodate simple internal components that function in a similar fashion as all of the different sized clip appliers, with only changing the geometry of the components. At the same time not compromising a high clip pushing force with low driving force. Better motion and force characteristics and simpler components resulting in better performance of the device.

SUMMARY

The present application relates to surgical clip appliers having a plurality of clips for applying the clips to body tissues and vessels during surgical.

According to an aspect of the present disclosure, a surgical clip applier is provided including a housing; at least one handle pivotably connected to the housing; a channel assembly extending distally from the housing; a clip carrier disposed within the channel assembly and defining a channel and a plurality of windows therein; a plurality of clips slidably disposed within the channel of the clip carrier; a drive channel reciprocally disposed within at least one of the housing and the channel assembly, the drive channel having a first end operatively connected to the at least one handle and a second end operatively connected to a distal end of the channel assembly; a wedge plate reciprocally disposed within the channel assembly, the wedge plate being operatively connected to the at least one handle and including a plurality of apertures formed along a length thereof; a pusher bar reciprocally positioned within the housing and the channel assembly, the pusher bar having a proximal end operatively connected to at least one handle and a distal end defining a pusher, wherein the distal end of the pusher bar is configured for engagement with a distal-most clip of the plurality of clips; and a motion multiplier system having a plurality of linkage members configured to distally move the pusher bar by an incremental amount upon an initial actuation of the handles, and configured to proximally move the pusher bar and the wedge plate subsequent to the initial actuation of the handles.

The plurality of linkages of the motion multiplier system may include a proximal linkage member pivotally supported in the housing and operatively connected to the drive channel; a pivoting drive arm interconnecting the drive channel and the proximal linkage member; and a distal linkage member interconnecting the proximal linkage member the pusher bar, such that a distal translation of the drive channel causes a pivotal rotation of the proximal linkage member via the pivoting drive arm, wherein the pivotal rotation of the proximal linkage member causes a pivotal rotation of the distal linkage member. The pivotal rotation of the distal linkage member causes a distal translation of the pusher bar. The proximal linkage member may be pivotally connected to the housing by a pivot pin. The distal linkage member may be pivotally connected to the proximal linkage member.

A further distal translation of the drive channel may cause a further pivotal rotation of the proximal linkage member via the pivoting drive arm, wherein the further pivotal rotation of the proximal linkage member causes a further pivotal rotation of the distal linkage member, and wherein the further pivotal rotation of the distal linkage member causes a proximal translation of the pusher bar.

In embodiments, when the proximal linkage member, the distal linkage member, the pivoting drive arm, the drive channel and the pusher bar are in a first position, the proximal linkage member and the distal linkage member define a first angle. Proximal translation of the drive channel causes the proximal linkage member and the distal linkage member, via the pivoting drive arm, to pivotally rotate thereby increasing the first angle to a second angle of about 180 degrees such that the proximal linkage member and the distal linkage member are linear to each other, such that the proximal linkage member, the distal linkage member, the pivoting drive arm, the drive channel and the pusher bar are in a second position.

Further, when the proximal linkage member, the distal linkage member, the pivoting drive arm, the drive channel and the pusher bar are in the second position, further proximal translation of the drive channel causes the proximal linkage member and the distal linkage member, via the pivoting drive arm, to pivotally rotate thereby decreasing the second angle of about 180 degrees to a third angle, such that the distal linkage member, the pivoting drive arm, and the drive channel are in a third position, while the pusher bar is in the first position.

The rotation of the proximal linkage member via the pivoting drive arm causes the proximal linkage member and the distal linkage member to be linear to each other and along a longitudinal axis defined by a reference axis between the proximal end of the proximal linkage member and the distal end of the distal linkage member, such that the distal linkage member causes a distal translation of the pusher bar.

Further rotation of the proximal linkage member via the pivoting drive arm causes the proximal member and the distal linkage member to be angularly offset from each other, such that the distal linkage member causes a proximal translation of the pusher bar.

A longitudinal axis, defined by a reference axis between the proximal end of the proximal linkage member and the distal end of the distal linkage member, and the proximal linkage member define a first acute angle on a first side of the longitudinal axis, and the pusher bar is in a proximal position. The distal translation of the drive channel may cause the proximal linkage member and the distal linkage member to pivot such that the first acute angle on the first side of the longitudinal axis increases until the proximal linkage member and the distal linkage member are linear to each other and the pusher bar has been distally translated via the distal linkage member to a distal position.

Further distal translation of the drive channel causes the proximal linkage member and the distal linkage member to pivot from the side of the longitudinal axis to a second side of the longitudinal axis such that the proximal linkage member and the longitudinal axis define a second acute angle and the pusher bar has been proximally translated via the distal linkage member to a proximal position.

The clip follower is configured to engage the wedge plate and move distally upon distal translation of the wedge plate, and is configured to engage the clip carrier and stop proximal movement thereof upon proximal translation of the wedge plate.

The clip applier may further include a jaw assembly having a pair of jaws extending from an end of the channel assembly, opposite the housing. The jaw assembly may be adapted to accommodate a clip of the plurality of clips therein and is operable to effect formation of the clip in response to movement of the handles.

The pusher bar may be movable towards the jaws as the handles are approximated in a first direction by an initial amount in order to move a distal-most clip between the jaws. The pusher bar may be configured and adapted to move towards the housing as the handles are approximated an additional amount in the first direction to move the pusher behind a distal-most clip in the plurality of clips.

The drive channel may be configured and dimensioned to at least partially surround the jaws and the wedge plate. The drive channel may include a strap extending across a distal end thereof for maintaining the jaws and the wedge plate within the drive channel.

The drive channel may be moved towards the jaw assembly as the at least one handle is moved actuated in a first direction to move the second end of the drive channel against the jaws to close the jaws, the drive channel being moved away from the jaws as the at least one handle is moved a second amount to move the second end of the drive channel away from the jaws to allow the jaws to open.

In embodiments, the clip applier may further include a motion reversing mechanism operatively connected to the wedge plate and the drive channel. The rotation of the motion reversing mechanism, during distal movement of the drive channel, results in proximal movement of the wedge plate.

In embodiments, the clip applier may further include a clip follower slidably disposed within the channel of the clip carrier and disposed proximally of the plurality of clips, the clip follower being configured and adapted for selective engagement with the windows of the clip carrier and the apertures of the wedge plate. The clip follower may be configured and adapted to urge the plurality of clips, in a distal direction relative to the clip carrier, upon reciprocal movement of the wedge plate.

In embodiments, the clip applier may further include a motion reversing mechanism operatively connected to the drive channel and the wedge plate and selectively engageable with the pusher bar. The rotation of the motion reversing mechanism, during the distal translation of the drive channel, results in proximal movement of the wedge plate and the pusher bar.

In embodiments, the clip applier may further include a ratchet mechanism. The ratchet mechanism may further include a rack, having a plurality of ratchet teeth, associated with the drive channel; and a pawl, having at least one tooth, disposed at a location to selectively engage the rack. The pawl may be biased into engagement with the rack, wherein as the drive channel is longitudinally reciprocated, the plurality of teeth are passed over the pawl. The pawl may prevent inadvertent return of the drive channel before full actuation of the at least one handle.

In embodiments, the clip applier may further include a lockout disposed in a distal end of the channel assembly. The lockout may be actuated by the clip follower when a last clip is expelled from the clip applier. The lockout may be urged by the clip follower to extend across a path of the drive channel, thereby preventing the drive channel from moving distally.

In embodiments, the clip applier may further include a counter display mechanism supported in at least one of the housing and the channel assembly. The counter display mechanism is configured and adapted to display a change in status of the clip applier upon each actuation of the at least one handle.

BRIEF DESCRIPTION OF THE DRAWINGS

The present clip applier will be more fully appreciated as the same becomes better understood from the following detailed description when considered in connection with the following drawings, in which:

FIG. 7 is an enlarged view of the indicated area of detail of FIG. 5;

FIG. 8 is an enlarged view of the indicated area of detail of FIG. 5;

FIG. 16 is a top, perspective view of a distal end of the channel assembly of FIG. 12, with the cover, the pusher bar, the clip carrier, the surgical clips and the clip follower removed therefrom;

FIG. 17 is an enlarged view of the indicated area of detail of FIG. 16;

FIG. 20 is a top, perspective view of the surgical clip applier of FIGS. 1-4, illustrated with the upper housing half, the pusher bar, the wedge plate and a drive channel removed therefrom;

FIG. 21 is a bottom, perspective view of the surgical clip applier of FIGS. 1-4, illustrated with a lower housing half, the drive channel and the wedge plate removed therefrom;

FIG. 25 is a top, plan view of the surgical clip applier of FIGS. 1-4, with the upper housing half removed therefrom and shown during an initial actuation thereof;

FIG. 28 is an enlarged, longitudinal cross-sectional view of the distal end of the channel assembly during the initial actuation of the surgical clip applier;

FIG. 29 is a top, perspective view of the surgical clip applier of FIGS. 1-4, illustrated with the upper housing half and a pusher bar removed therefrom and shown in during an initial actuation thereof;

FIG. 36 is an enlarged view of a ratchet mechanism shown during the final actuation of the surgical clip applier of FIGS. 1-4;

FIGS. 37 and 38 are enlarged perspective view, illustrating the distal end of the channel assembly during the final actuation of the surgical clip applier of FIGS. 1-4;

FIGS. 48 and 49 are longitudinal, cross-sectional views of the channel assembly illustrating the movement of the clip follower during the opening or release of the surgical clip applier of FIGS. 1-4;

DETAILED DESCRIPTION OF EMBODIMENTS

Figure 1:
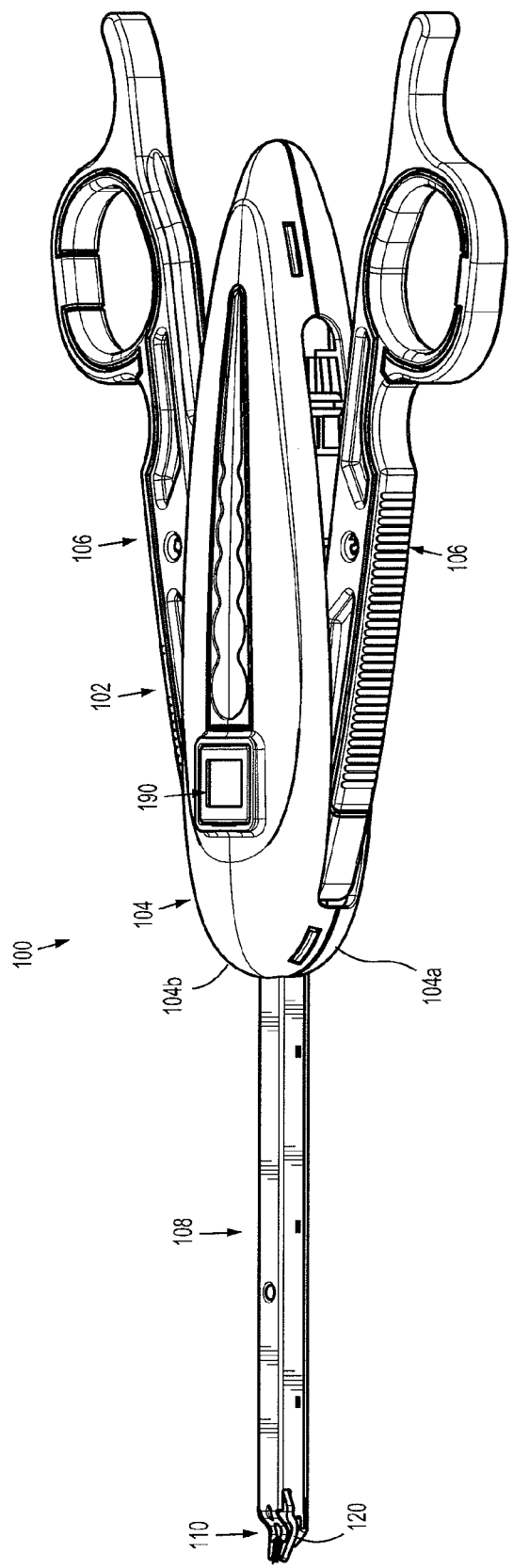
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

FIGS. 1-5 illustrate a surgical clip applier in accordance with an embodiment of the present disclosure and is generally designated as 100. Reference may be made to U.S. Provisional Application No. 61/091,467, filed on Aug. 25, 2008, entitled "Surgical Clip Applier" and U.S. Provisional Application No. 61/091,485, filed on Aug. 25, 2008, entitled "Surgical Clip Applier and Method of Assembly," the entire contents of each of which being incorporated herein by reference, for a detailed discussion of the structure, operation, and method of assembly of surgical clip applier 100.

Surgical clip applier 100 is a surgical instrument including a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in a jaw assembly 110.

As seen in FIGS. 1-4, housing halves 104a and 104b of clip applier 100 fit together by snap fit engagement with one another. Housing 104 defines a window 104c formed in lower housing half 104b for supporting and displaying a counter mechanism, as will be discussed in greater detail below. Housing 104 is formed of a suitable plastic material.

Figure 4:
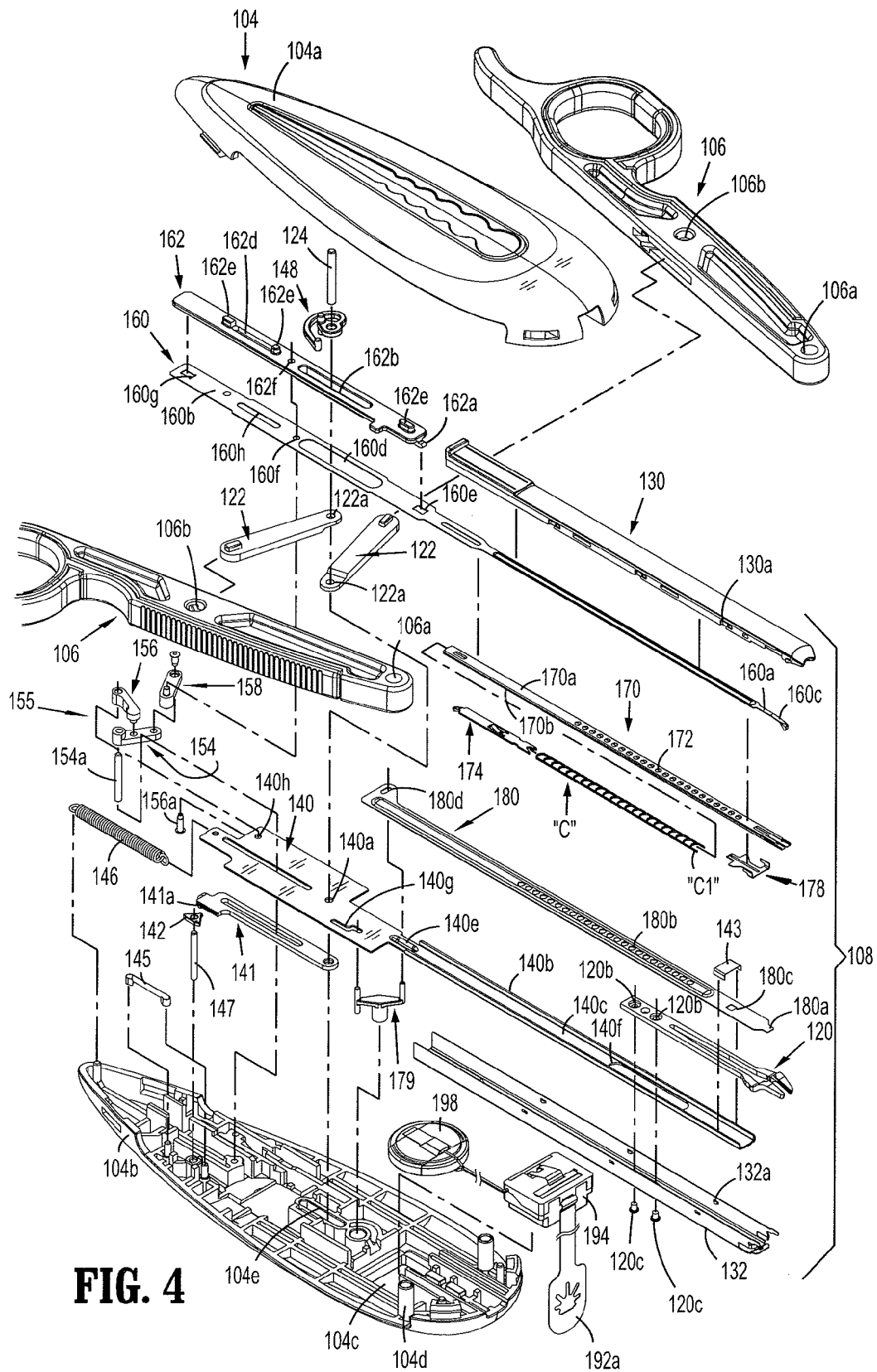
FIG. 4 is an exploded perspective view of the surgical clip applier of FIGS. 1-3.
Figure 4A:
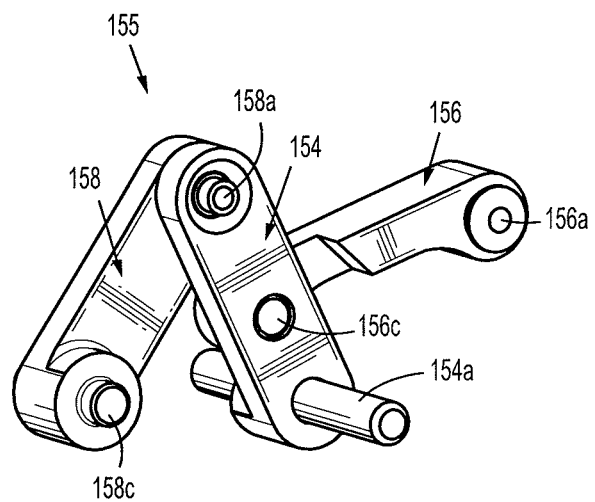
FIG. 4A is a perspective view of a motion multiplier system of the surgical clip applier of FIGS. 1-4.
Figure 4B:
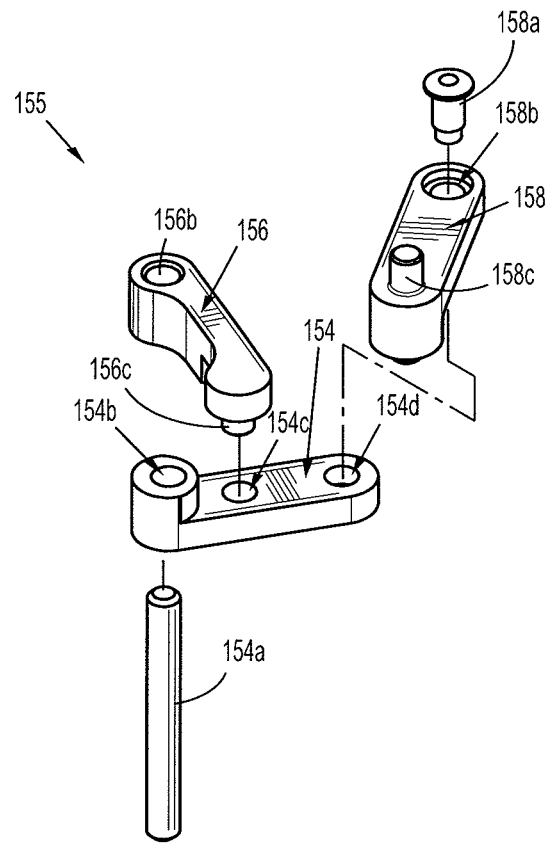
FIG. 4B is an exploded perspective view of the motion multiplier system of the surgical clip applier of FIGS. 1-4.
Figure 4C:
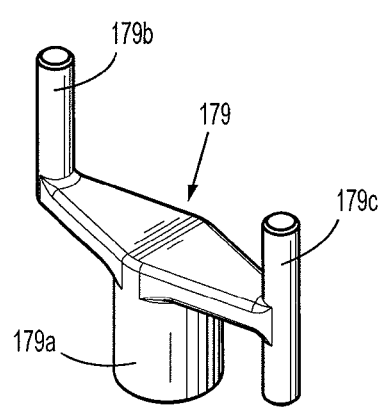
FIG. 4C is a top, perspective view of a pivot arm of the surgical clip applier of FIGS. 1-4.
Figure 4D:
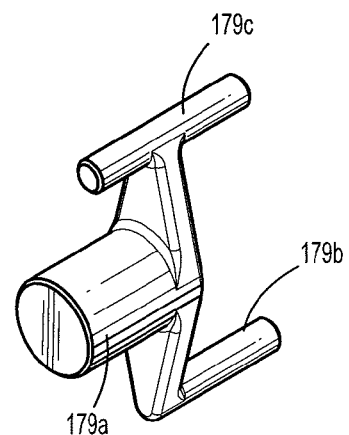
FIG. 4D is a bottom, perspective view of the pivot arm of FIG. 4C.

As seen in FIG. 4, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end 122a of each link member 122 is pivotally connected to a pivot point 140a formed in a drive channel 140 via a drive pin 124. Each end of drive pin 124 is slidably received in an elongate channel 104e formed in a respective upper and lower housing half 104a, 104b. In use, as will be described in greater detail below, as handles 106 are squeezed, link members 122 push drive channel 140 distally via drive pin 124.

Channel assembly 108 includes a channel or cartridge cover 130 and an outer or lower channel 132 each having a proximal end retained in housing assembly 102, between upper and lower housing halves 104a, 104b. Cartridge cover 130 includes at least one retention element 130a configured and adapted to selectively engage, in a snap-fit engagement, a complementary or corresponding retention element 132a provided on outer channel 132.

As seen in FIGS. 4 and 6-12, clip applier 100 includes a clip pusher bar 160 slidably disposed beneath cartridge cover 130. Pusher bar 160 includes a distal end 160a defining a pusher 160c configured and adapted to selectively engage/move a distal-most clip "C1" stored in surgical clip applier 100. Pusher bar 160 further includes a proximal end 160b defining a first proximal window 160d and a second proximal window 160h therein. First proximal window 160d is configured for slidably receiving drive pin 124 therein and second proximal window 160h is configured for slidably receiving fixed rod 154a therein. Pusher bar 160 further defines a distal window 160e and a proximal window 160g therein for operative engagement with a stabilizer 162, as will be discussed in greater detail below. Pusher bar 160 further includes an aperture 160f configured to receive a sliding post 158c of a distal linkage member 158, as will described in greater detail below.

Figure 6:
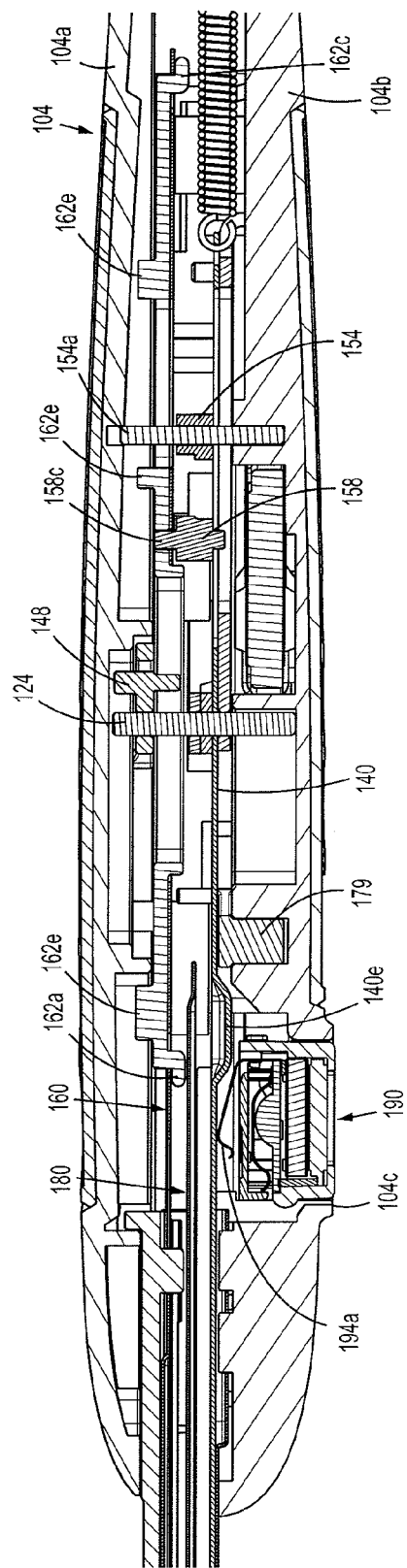
FIG. 6 is an enlarged view of the indicated area of detail of FIG. 5.

Clip applier 100 further includes a stabilizer 162 configured to overlie and engage pusher bar 160. Stabilizer 162 includes a distal tab 162a configured to engage distal window 160e of pusher bar 160, elongate windows 162b and 162d defined therein at a location to substantially overlie and be in registration with respective proximal windows 160d and 160h formed in pusher bar 160. As seen in FIGS. 4 and 6, stabilizer 162 further includes a plurality of tabs 162e extending from a top surface thereof, at a proximal and a distal location, which are configured and dimensioned for receipt in respective channels formed in upper housing half 104a. Stabilizer 162 further includes an aperture 162f that overlies aperture 160f of pusher bar 160. Apertures 160f and 162f are both configured to receive sliding post 158c of distal linkage member 158.

Figure 24:
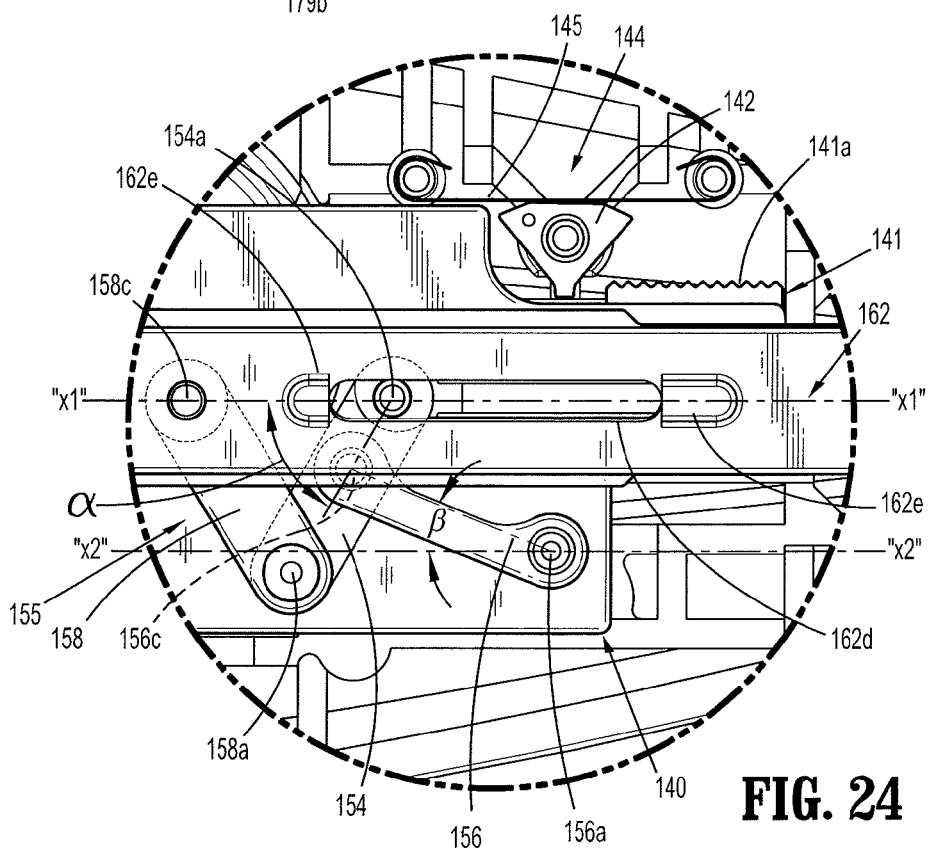
FIG. 24 is an enlarged view of the indicated area of detail of FIG. 22.
Figure 27:
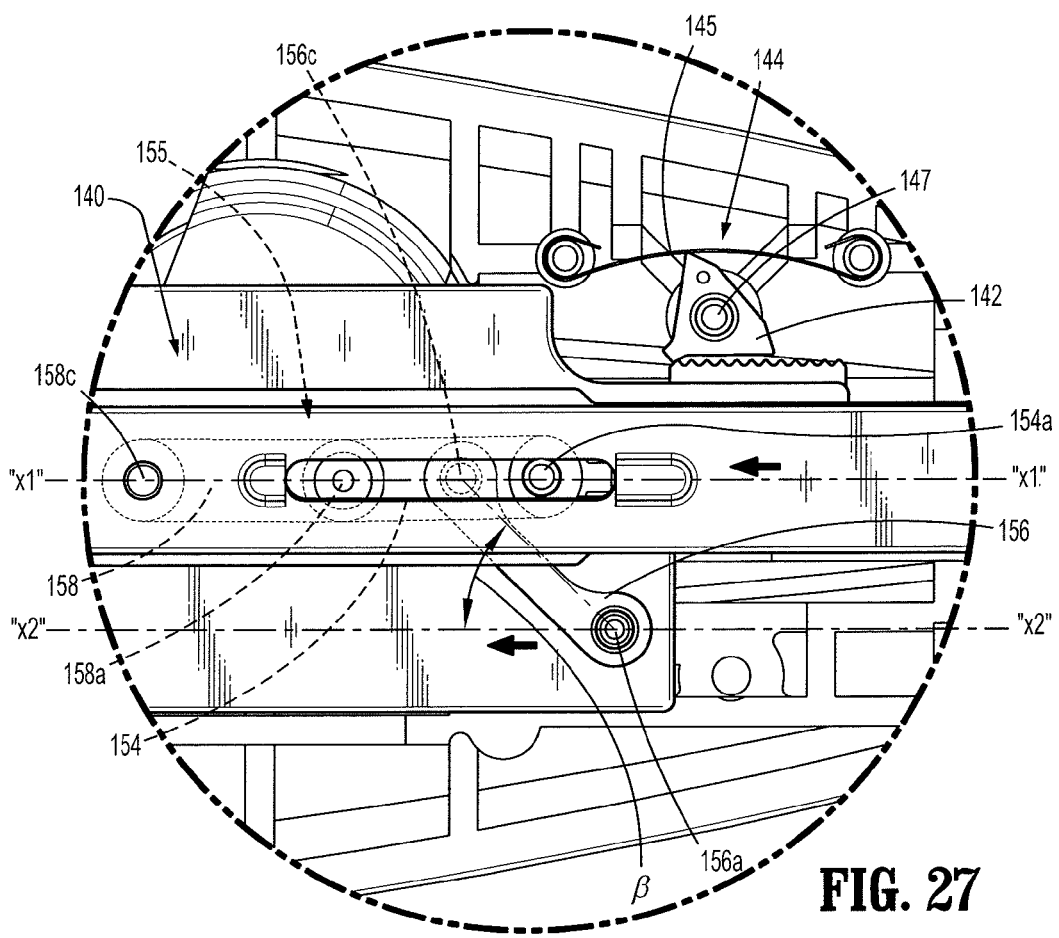
FIG. 27 is an enlarged view of the indicated area of detail of FIG. 25.
Figure 35:
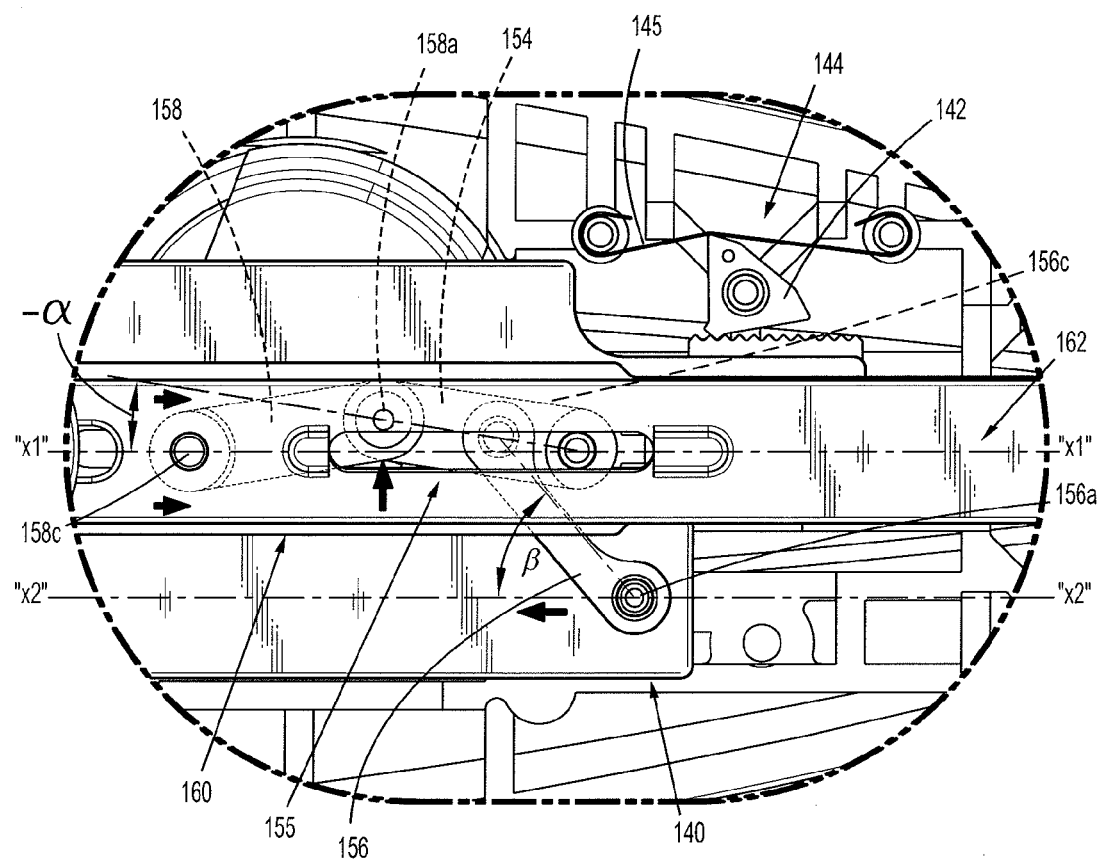
FIG. 35 is an enlarged view of the indicated area of detail of FIG. 32.

As seen in FIGS. 4, 4A, 4B, and 24, clip applier 100 further includes a motion multiplier system 155 in the form of a three-bar linkage system having a proximal linkage member 154 that is pivotally supported in housing 104 and operatively connected to drive channel 140 via a pivoting drive arm 156. Pivoting drive arm 156 is pivotably coupled by a pin 156a via aperture 156b to housing 104. Motion multiplier system 155 further includes a distal linkage member 158 that interconnects proximal linkage member 154 and pusher bar 160. A longitudinal axis "X1" is defined along an axis extending through fixed rod 154a of proximal linkage member 154 and sliding post 158c of distal linkage member 158. A side of longitudinal axis "X1," that includes pivoting drive arm 156, defines a first side and the other side of longitudinal axis "X1" defines a second side. On the first side, proximal linkage member 154 is pivotally oriented at an angle "α" relative to longitudinal axis "X1" (as shown in FIG. 24). On the second side, proximal linkage member 154 is pivotally oriented at an angle "–α" relative to longitudinal axis "X1" (as shown in FIG. 35). In essence, when proximal linkage member 154 is oriented between angle "α" and angle "–α," the angle is 0°, such that proximal linkage member 154 is aligned with longitudinal axis "X1" (as shown in FIG. 27). In this configuration, proximal linkage member 154 is also aligned with distal linkage member 158, as will be discussed in greater detail below. Pivoting drive arm 156 is pivotally supported via a pivot pin 156a secured and driven by drive channel 140. A longitudinal axis "X2" is defined along an axis extending along drive channel 140. In this manner, pivoting drive arm 156 is pivotally oriented at an angle "β" relative to longitudinal axis "X2" (as shown in FIG. 24).

Proximal linkage member 154 includes a hub 154b that is configured to receive a fixed rod 154a therethrough, such that a pivotable connection between proximal linkage member 154 and housing 104 is established. Proximal linkage member 154 also includes a proximal aperture 154c and a distal aperture 154d. Proximal aperture 154c is configured to receive a driving post 156c of pivoting drive arm 156 that selectively drives proximal linkage member 154 in a rotational manner, as will be discussed in greater detail below. Distal aperture 154d is configured to receive a coupling pin 158a via aperture 158b of distal linkage member 158 that pivotally couples proximal linkage member 154 to distal linkage member 158. Distal linkage member 158 further includes a post 158c that is slidably connected to aperture 160f of pusher bar 160 and aperture 162f of stabilizer 162. Distal linkage member 158 via sliding post 158c effectuates translation of pusher bar 160 and stabilizer 162 in a proximal and distal direction.

Clip applier 100 further includes a clip carrier 170 disposed within channel assembly 108 and beneath pusher bar 160. Clip carrier 170 is generally a box-like structure having an upper wall 170a, a pair of side walls 170b and a lower wall 170c defining a channel 170d therethrough. Clip carrier 170 includes a plurality of spaced apart windows 172 formed in upper wall 170a and extending longitudinally along a length thereof. Clip carrier 170 includes an elongate window 170e (as shown in FIG. 9) formed in lower wall 170c and extending longitudinally along a length thereof.

Figure 4E:
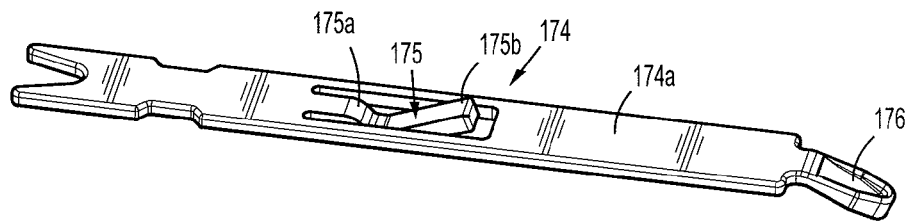
FIG. 4E is a top, perspective view of a clip follower of the surgical clip applier of FIGS. 1-4.
Figure 4F:
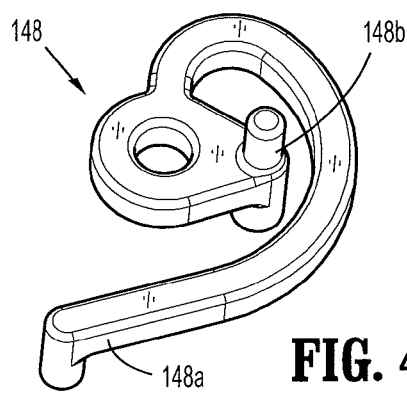
FIG. 4F is a perspective view of an audible/tactile indicator of the surgical clip applier of FIGS. 1-4.
Figure 4G:
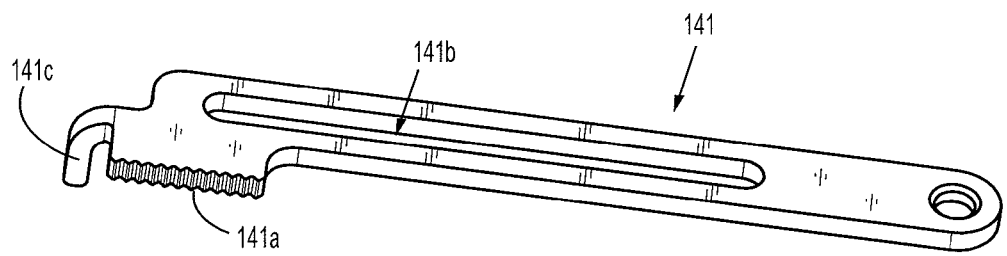
FIG. 4G is a perspective view of a rack member of the surgical clip applier of FIGS. 1-4.
Figure 4H:
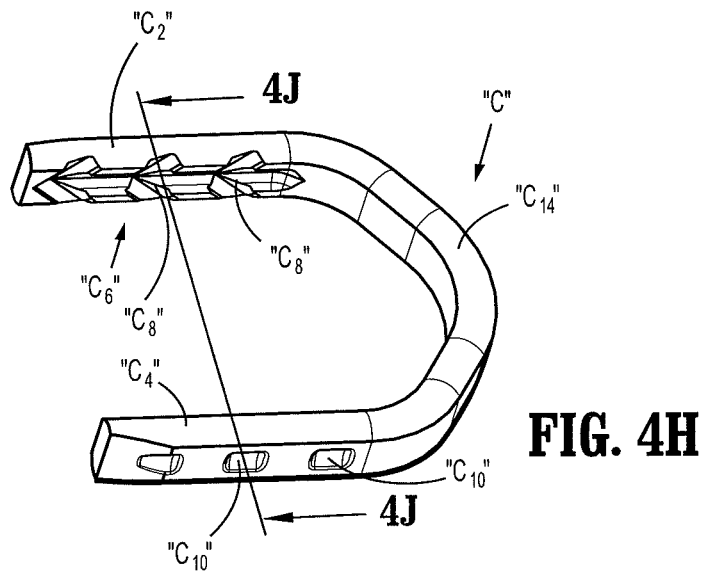
FIG. 4H is a top, perspective view of a surgical clip.
Figure 4I:
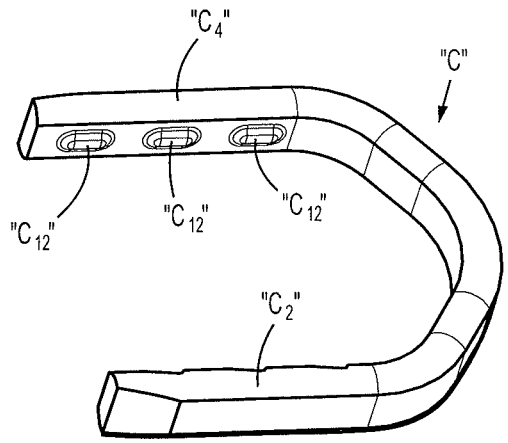
FIG. 4I is a bottom, perspective view of the surgical clip of FIG. 4H.
Figure 4J:
FIG. 4J is a front, cross-sectional view of the surgical clip of FIG. 4H, as taken through 4J-4J of FIG. 4H.
Figure 5:
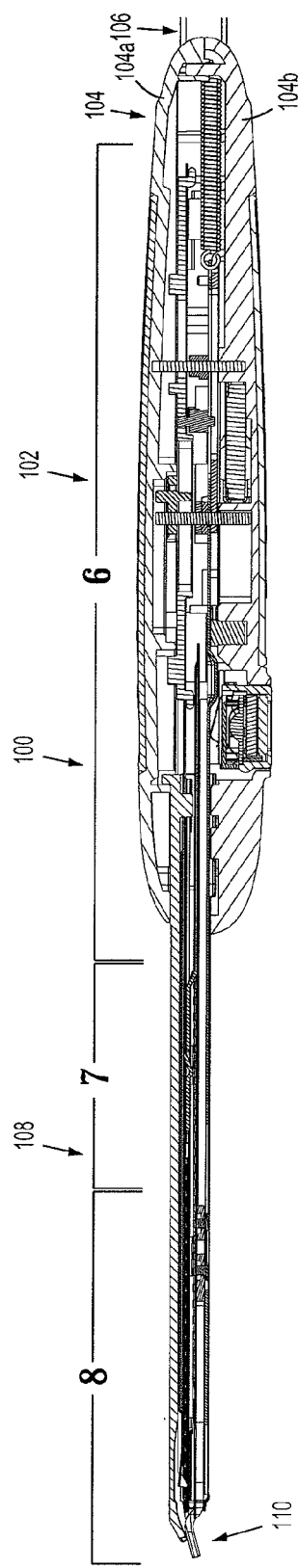
FIG. 5 is a longitudinal cross-sectional view of the surgical clip applier of FIGS. 1-4, illustrating the surgical clip applier in an unactuated condition.

As seen in FIGS. 4H-4J, a surgical clip "C" includes a first leg "C2" and a second leg "C4." Each of legs "C2" and "C4" of surgical clip "C" are connected to one another to form an apex "C14." Apex "C14" of surgical clip "C" has a generally V-shaped configuration as shown in FIGS. 4H-4I. First leg "C2" of surgical clip "C" further includes a gripping pattern "C6" on an interior wall that defines a plurality of recesses "C8." Second leg "C4" of surgical clip "C" includes a plurality of indentations "C10" on an exterior wall and a plurality of protrusions "C12" on an interior wall. When surgical clip "C" is applied to tissue, as the application a clip "C" to tissue will be described in greater detail below, legs "C2" and "C4" come together, such that plurality of indentations "C10" and plurality of protrusions "C12" grip and hold a tissue therebetween. For a more detailed discussion of surgical clip "C," please refer to commonly owned U.S. Publication No. 2007/0173866, filed on Jan. 23, 2006, entitled "Surgical Hemostatic Clip," the entire contents of which is incorporated herein by reference in its entirety.

Figure 9:
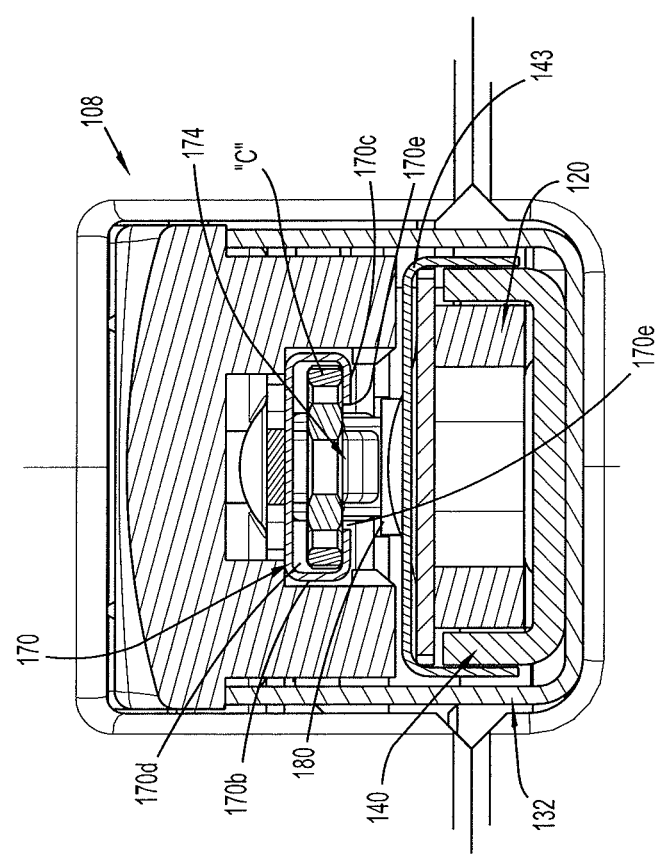
FIG. 9 is a cross-sectional view of the surgical clip applier of FIGS. 1-4, as taken through 9-9 of FIG. 8.
Figure 10:
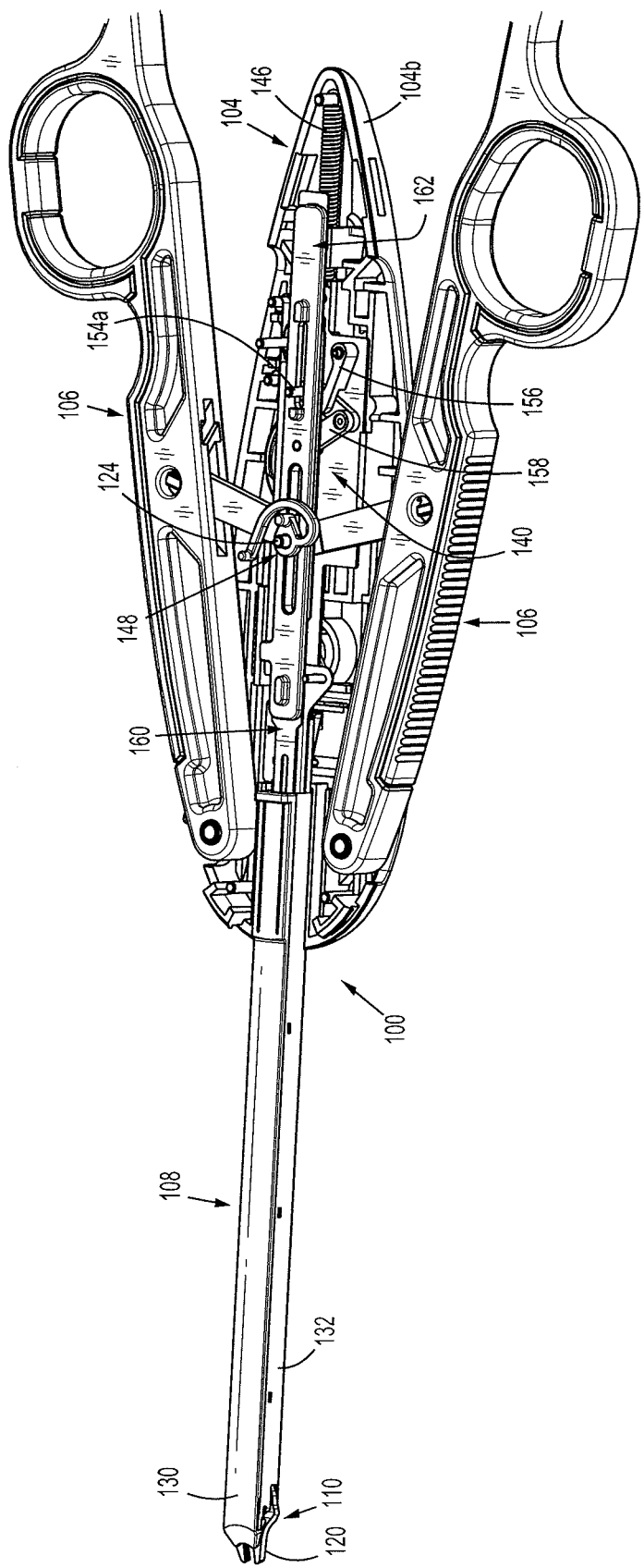
FIG. 10 is a perspective view of the surgical clip applier of FIGS. 1-4, illustrated with an upper housing half removed therefrom.
Figure 11:
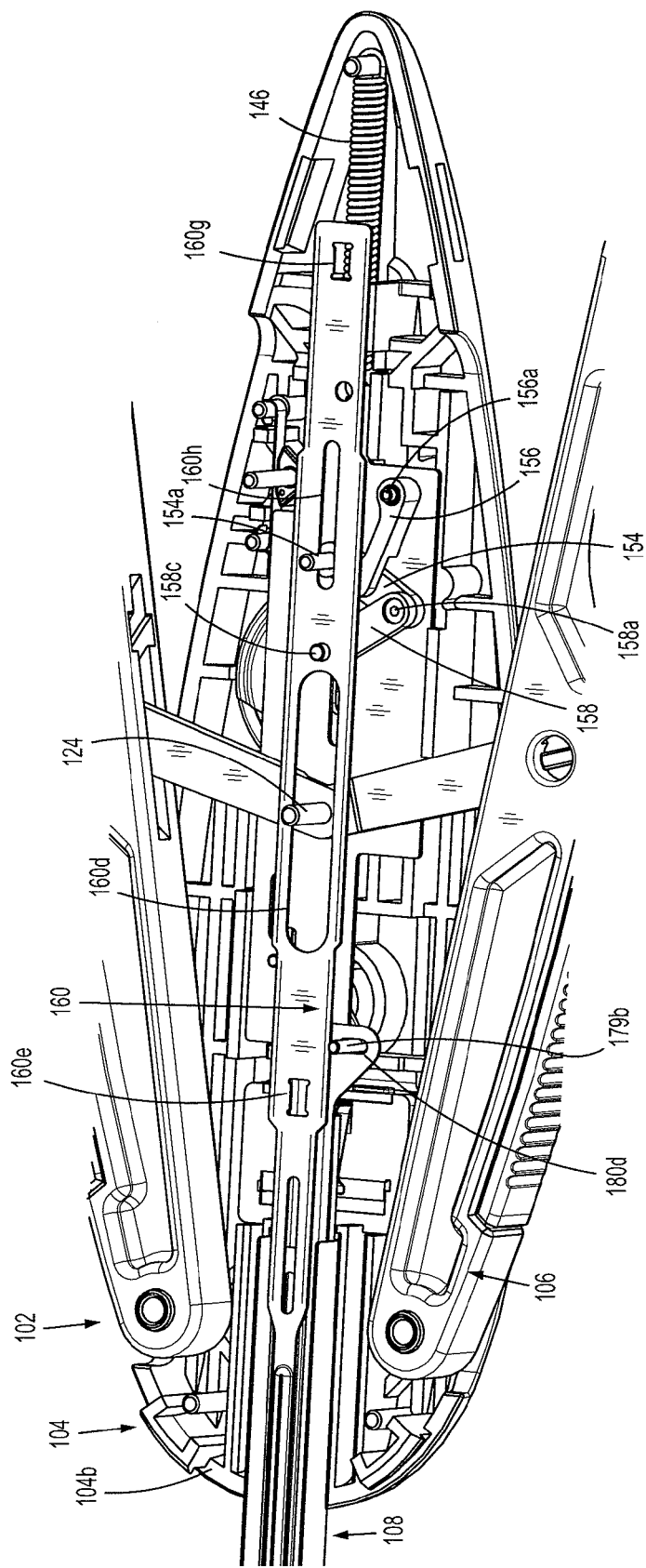
FIG. 11 is an enlarged view of the surgical clip applier of FIGS. 1-4, as shown in FIG. 10.
Figure 14:
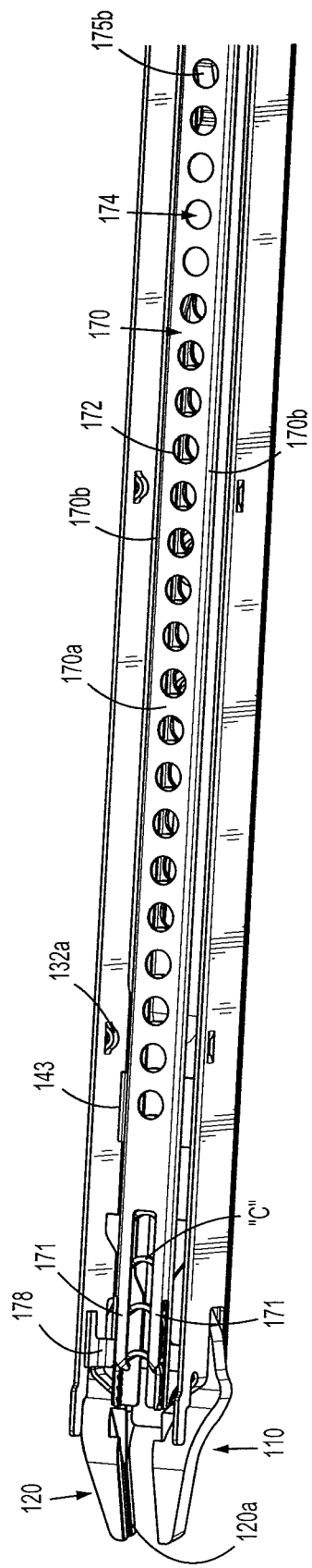
FIG. 14 is a top, perspective view of a distal end of the channel assembly of FIG. 12, with the cover and the pusher bar removed therefrom.
Figure 15:
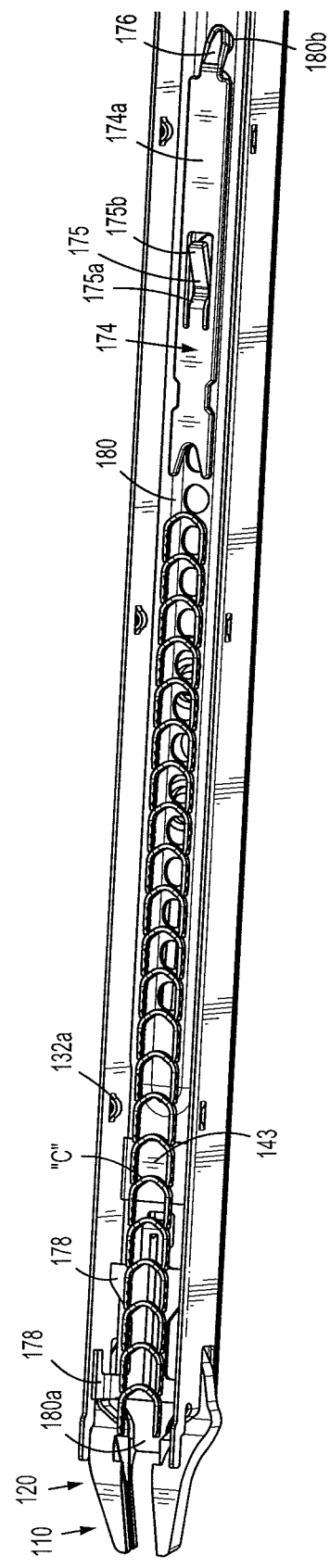
FIG. 15 is a top, perspective view of a distal end of the channel assembly of FIG. 12, with the cover, the pusher bar and a clip carrier removed therefrom.
Figure 18:
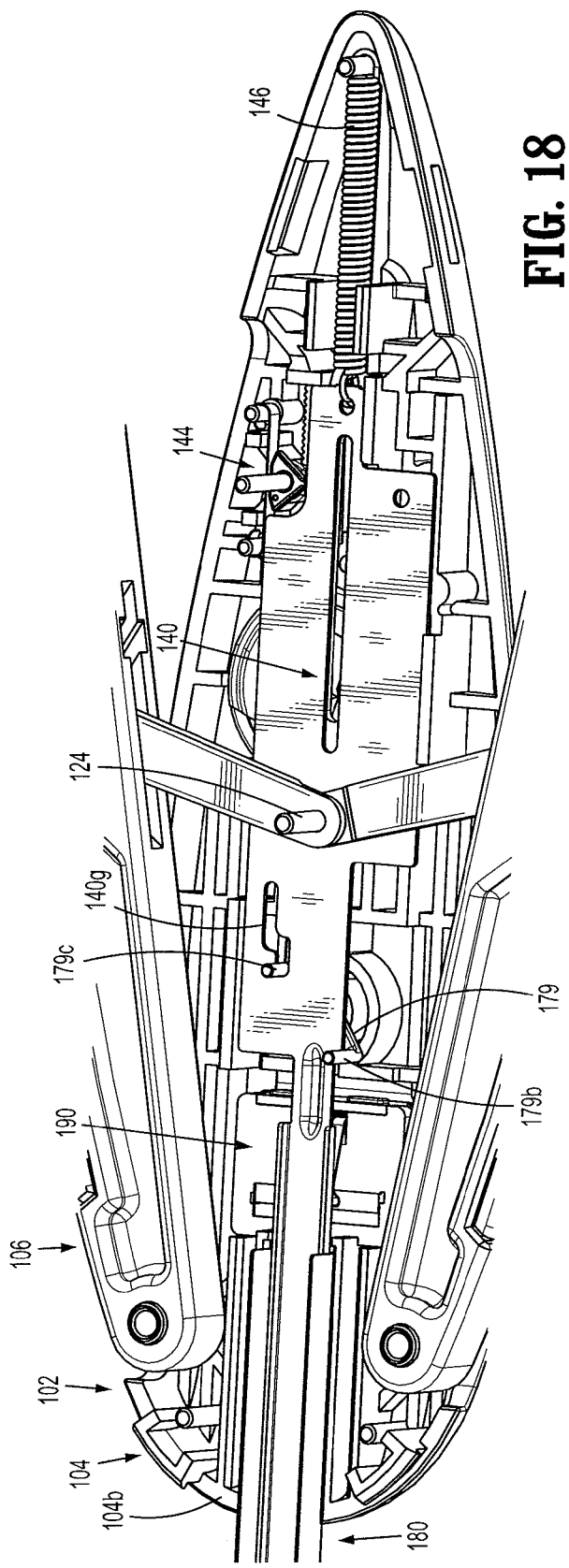
FIG. 18 is a top, perspective view of the surgical clip applier of FIGS. 1-4, illustrated with the upper housing half, the pusher bar and a wedge plate removed therefrom.
Figure 19:
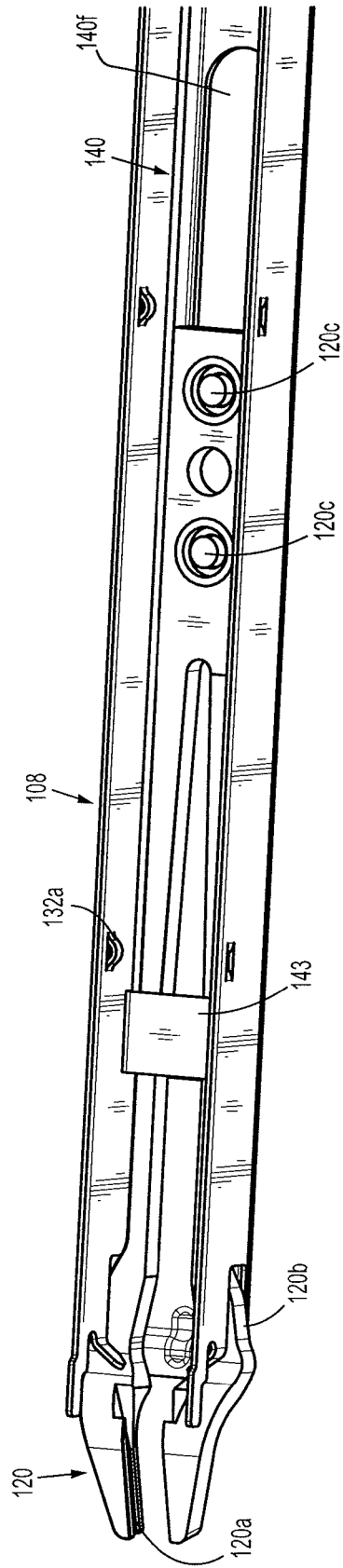
FIG. 19 is a top, perspective view of a distal end of the channel assembly of FIG. 12, with the cover, the pusher bar, the clip carrier, the surgical clips, the clip follower and the wedge plate removed therefrom.

As seen in FIGS. 4, 9 and 14, a stack of surgical clips "C" is loaded and/or retained within channel 170d of clip carrier 170 in a manner so as to slide therewithin and/or therealong. Channel 170d is configured and dimensioned to slidably retain a stack or plurality of surgical clips "C" in tip-to-tail fashion therewithin.

Figure 12:
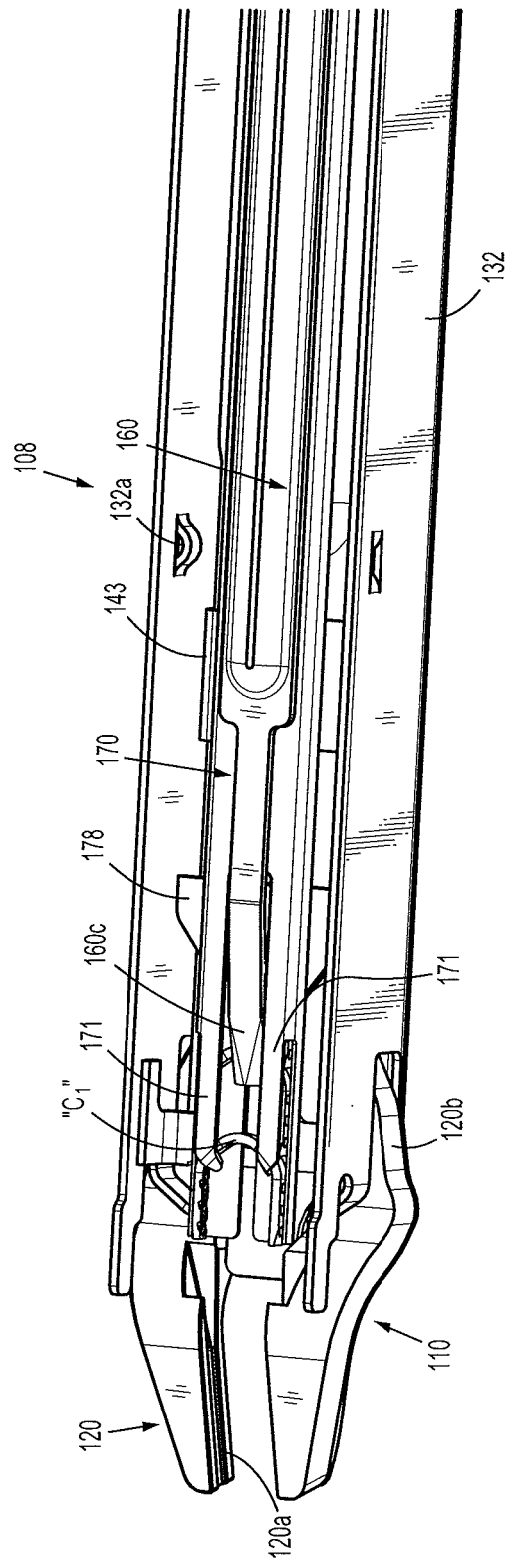
FIG. 12 is a top, perspective view of a distal end of a channel assembly of the surgical clip applier of FIGS. 1-4, with a cover removed therefrom.
Figure 13:
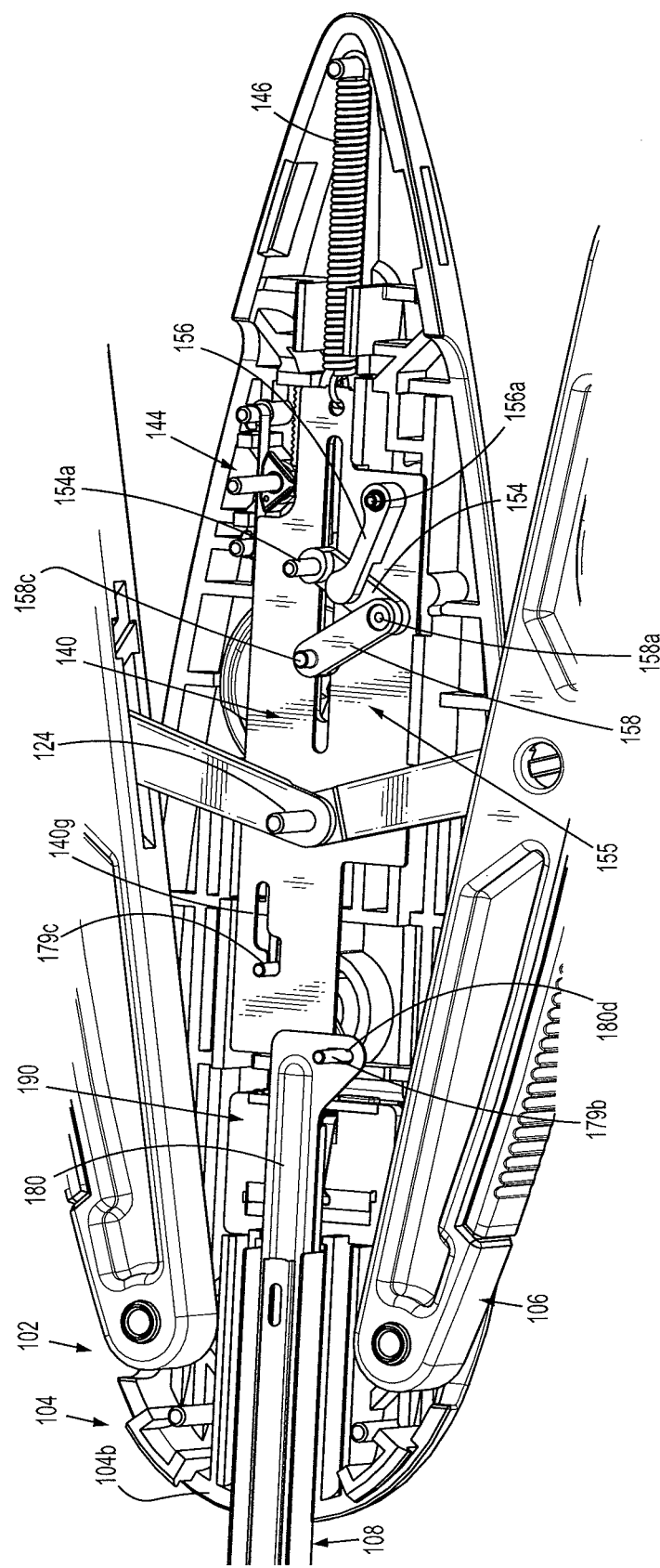
FIG. 13 is a top, perspective view of the surgical clip applier of FIGS. 1-4, illustrated with the upper housing half and a pusher bar removed therefrom.

As seen in FIGS. 12 and 14, a distal end of clip carrier 170 includes a pair of spaced apart, resilient tangs 171. Tangs 171 are configured and adapted to selectively engage a backspan of a distal-most surgical clip "C1" of the stack of surgical clips "C" retained within carrier 170.

As seen in FIGS. 4, 4E, 7 and 15, clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. As will be described in greater detail below, clip follower 174 is actuated by the reciprocating forward and backward motion of wedge plate 180.

As seen in FIGS. 4E and 7, clip follower 174 includes body portion 174a defining a plane, a distal tab 175 extending substantially upwardly and rearwardly from body portion 174a, and a proximal tab 176 extending substantially downwardly and rearwardly from body portion 174a. Distal tab 175 includes a distal portion 175a extending downwardly below the plane defined by body portion 174a and a proximal portion 175b extending upwardly above the plane defined by body portion 174a.

Proximal portion 175b of distal tab 175 is configured and dimensioned to selectively engage windows 172 formed in upper wall 170a of clip carrier 170. In use, engagement of proximal portion 175b of distal tab 175 of clip follower 174 in a window 172 formed in upper wall 170a of clip carrier 170 prevents clip follower from traveling or moving in a proximal direction.

Proximal tab 176 is configured and dimensioned to selectively engage windows 180b formed in wedge plate 180. In use, engagement of proximal tab 176 of clip follower 174 in a window 180b formed in wedge plate 180 allows for clip follower 174 to be advanced or moved distally upon a distal movement of wedge plate 180.

As seen in FIGS. 4, 7-9, 16 and 17, clip applier 100 further includes a wedge plate 180 slidably disposed within handle assembly 102 and channel assembly 108. Wedge plate 180 is positioned or disposed below clip carrier 170. Wedge plate 180 includes a substantially tapered distal end 180a for selective operative interposition between jaws 120. Wedge plate 180 defines a plurality of spaced apart windows or apertures 180b extending longitudinally along a length thereof and formed in a raised section thereof, a distal window or aperture 180c located distal of apertures 180b, and a proximal-most transversely oriented slot 180d located proximal of aperture 180c.

As seen in FIGS. 4, 8, 16 and 17, clip applier 100 includes a distal lockout 178 supported by cartridge cover 130. Distal lockout 178 includes a tail or tab 178a extending substantially rearwardly and downwardly and being configured and dimensioned for receipt in distal window or aperture 180c of wedge plate 180.

As seen in FIGS. 4, 4C, 4D, 6, 11, 13, 18 and 20, clip applier 100 includes a wedge plate motion reversing mechanism, in the form of a pivot arm 179, pivotally supported in lower housing half 104b of housing 104 for transmitting the translation of drive channel 140 to a reverse translation of wedge plate 180. Pivot arm 179 includes a pivot boss 179a configured for pivotable connection to housing 104, a first stem or finger 179b provided at one end of pivot arm 179 and extending in a direction opposite to pivot boss 179a, and second stem or finger 179c provided at a second end of pivot arm 179 and extending in a direction alongside first stem or finger 179b and pivot boss 179a. First stem or finger 179b is configured and adapted for engagement in proximal-most slot 180d of wedge plate 180. Second stem or finger 179c is configured for engagement in a slot 140g formed in drive channel 140 which is connected in a window 140g defined in a drive channel 140. Slot 140g includes a longitudinally extending distal portion and a longitudinally extending proximal portion that are axially and transversely offset from one another, and a transverse portion interconnecting the distal and proximal portions.

In use, as will be discussed in greater detail below, as drive channel 140 is moved distally, after a dwell period (i.e., the length of the longitudinally extending distal portion of slot 140g of drive channel 140), second stem or finger 179c is moved in a distal direction, rotating pivot arm 179 and thereby moving first stem or finger 179b in a second direction. As first stem or finger 179b is moved in the second direction, first stem or finger 179b pulls wedge plate 180 out from between jaws 120 urges against. As wedge plate 180 is moved in a distal direction, as seen n FIG. 17, distal end 180a of wedge plate 180 cams against an inner surface of jaws 120 to thereby maintain jaws 120 spaced apart from one another.

As seen in FIGS. 4, 6-11, 13, 18 and 19, clip applier 100 includes a drive channel 140 reciprocally supported in and extending between housing 104 of handle assembly 102 and channel assembly 108. A proximal end of drive channel 140 is supported between upper and lower housing halves 104a, 104b of housing 104 and a distal end of drive channel 140 is supported between cartridge cover 130 and outer channel 132 of channel assembly 108, at a location below wedge plate 180.

A distal end of drive channel 140 is a substantially U-shaped channel including a pair of spaced apart side walls 140b extending from a backspan 140c thereof, in a direction away from outer channel 132 and toward cartridge cover 130. Drive channel 140 further defines a drive pin recess 140a formed in backspan 140c for pivotally receiving drive pin 124 therethrough. Drive channel 140 further defines a rib 140e projecting from backspan 140c at a location distal of drive pin recess 140a. Drive channel 140 further defines a reciprocation limiting slot 140f formed in backspan 140c at a location distal of slot 140e.

As seen in FIGS. 4, 8, 9, 12, 14-16 and 19, clip applier 100 includes a drive channel strap 143 secured to drive channel 140. Strap 143 is secured to uprights 140b of drive channel 140 so as to extend transversely thereacross. Strap 143 is secured to drive channel 140 at a location distal of reciprocation limiting slot 140f. Strap 143 is secured to drive channel 140 such that wedge plate 180 extends beneath strap 143 and above jaws 120.

As seen in FIGS. 4, 4F, 6, 10 and 21, clip applier 100 further includes an audible/tactile indicator 148 connected to drive channel 140 via drive pin 124. Indicator 148 includes a resilient finger 148a and a pair of bosses 148b. In use, as will be described in greater detail below, as clip applier 100 is actuated and drive channel 140 is reciprocated, first resilient finger 148a of indicator 148 interacts with corresponding complementary structure or ledge 149 provided in clip applier 100 to create an audible and/or a tactile feedback to the user. Bosses 148b of indicator 148 ride within channel 104e formed in upper housing half 104a and provide support to indicator 148 to prevent indicator 148 from rotating.

As seen in FIGS. 4, 6, 10, 11, 13, 18 and 20, clip applier 100 further includes a biasing member 146, in the form of a tension spring, operatively secured to and between a proximal end of drive channel 140 and housing 104, tending to maintain drive channel 140 in a retracted or proximal-most position. Biasing member 146 functions to retract or facilitate retraction of drive channel 140 following formation of a clip "C" positioned between jaws 120.

As seen in FIGS. 4, 4G, 11, 13, 18 and 20, a proximal end of drive channel 140 includes a ratchet rack member 141 secured to drive pin 124 and movable with drive channel 140. Ratchet member 141 includes a slot 141b to slidably receive fixed rod 154a. Ratchet member 141 further includes a tab 141c extending from a proximal end thereof that slidably translates within lower housing half 104b. Ratchet rack member 141 is configured and adapted to engage with a ratchet pawl 142 supported in housing 104. Rack member 141 and ratchet pawl 142 define a ratchet mechanism 144. In use, as drive channel 140 is moved axially, rack member 141 is also moved. Rack member 141 defines a series of rack teeth 141a having a length which allows pawl 142 to reverse and advance back over rack member 141 when rack member 141 changes between proximal and distal movement as drive channel 140 reaches a proximal-most or distal-most position.

Pawl 142 is pivotally connected to lower housing half 104b by a pawl pin 147 at a location wherein pawl 142 is in substantial operative engagement with rack member 141. Pawl 142 is engageable with rack member 141 to restrict longitudinal movement of rack member 141 and, in turn, drive channel 140. Ratchet mechanism 144 further includes a pawl spring 145 configured and positioned to bias pawl 142 into operative engagement with rack member 141. Pawl spring 145 functions to maintain the teeth of pawl 142 in engagement with the teeth 141a of rack member 141, as well as to maintain pawl 142 in a rotated or canted position.

As seen in FIGS. 1-4, 8, 10, 12, 14-17 and 19, clip applier 100 includes a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of drive channel 140 via one or more rivets 120c or the like extending through reciprocation limiting slot 140f of drive channel 140 such that jaws 120 are longitudinally stationary relative to outer channel 132 and drive channel 140. As seen in FIGS. 12, 14, 17 and 19, jaws 120 define a channel 120a therebetween for receipt of a surgical clip "C1" therein.

As seen in FIGS. 1-4, 6, 11, 13 and 20, clip applier 100 further includes a counter mechanism 190 supported in housing 104 of handle assembly 102. Counter mechanism 190 includes a display 192, a processor 194, and an energy source 198 in the form of a battery or the like. Display 192 is a liquid crystal display that displays one or more operating parameters of clip applier 100 to the surgeon. The operating parameter displayed may be an amount or number of remaining clips, a number of clips that have been used, a position parameter, a surgical time of usage, or any other parameter of the procedure.

Figure 1A:
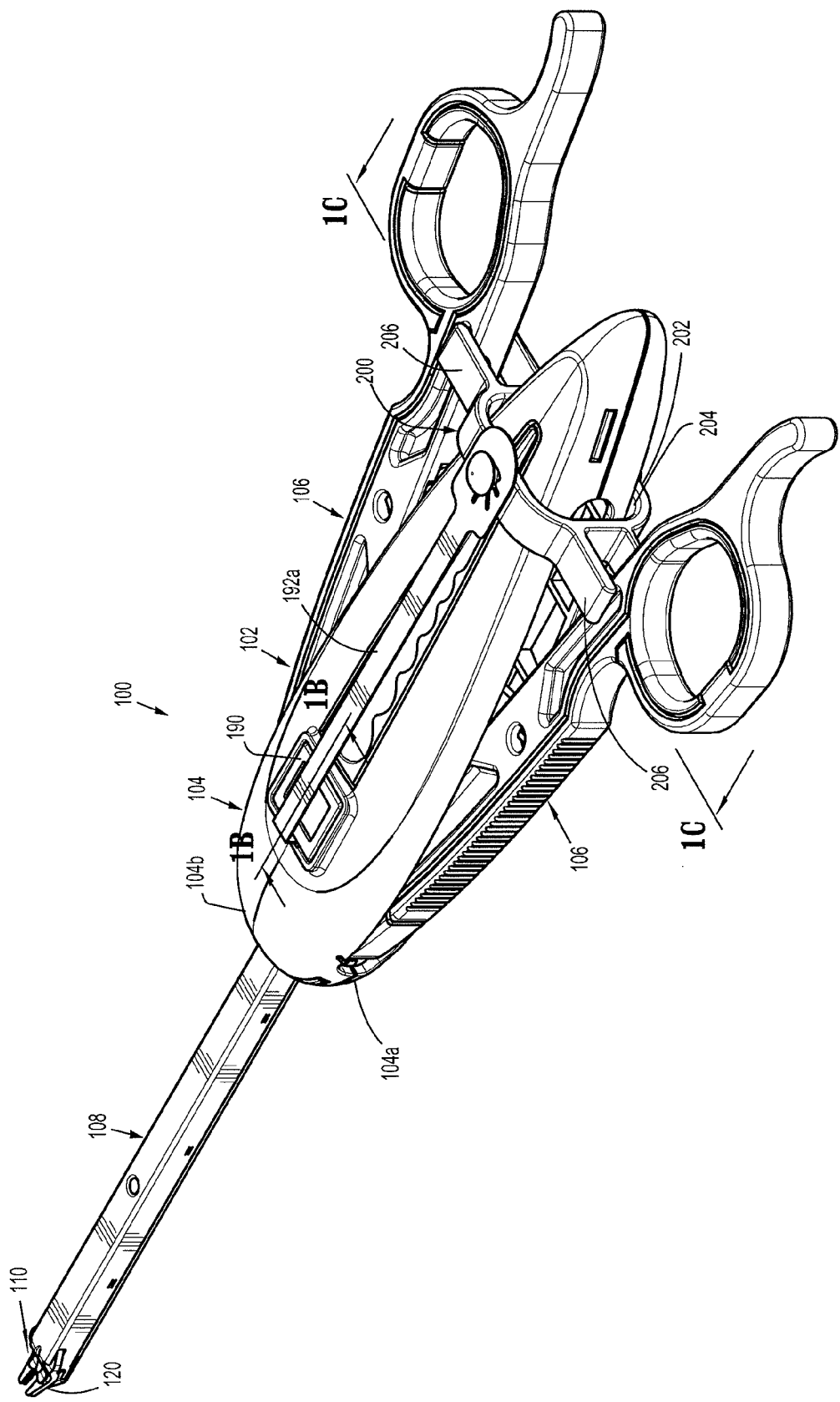
FIG. 1A is a rear, perspective view of the surgical clip applier of FIG. 1, shown with a shipping wedge in position.
Figure 1B:
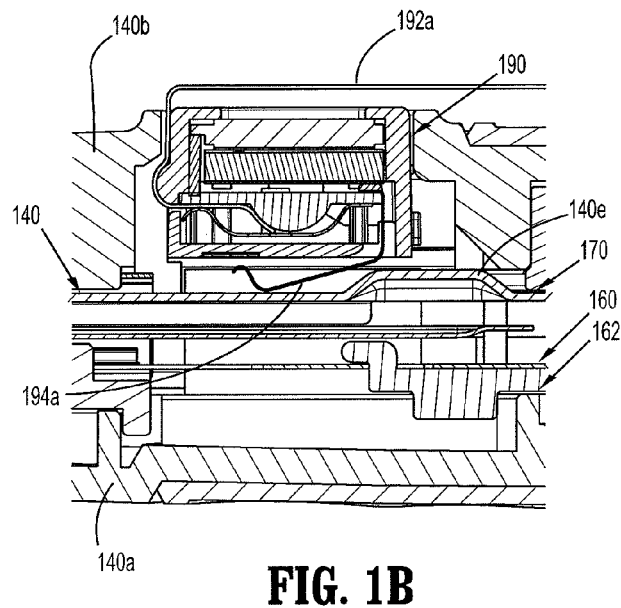
FIG. 1B is a cross-sectional view as taken through 1B-1B of FIG. 1A.

Counter mechanism 190 includes a tab 192a, made from PVC, disposed between battery or energy source 198 and a contact 194a of processor 194 or between the contacts 194a of processor 194 to prevent the battery or energy source 198 from becoming drained during storage. As seen in FIGS. 1A and 1B, tab 192a extends out of housing 104 of clip applier 100 in order to allow for easy removal of the tab therefrom. Once the tab 192a is removed, battery or energy source 198 comes into electrical contact with the contact 194a of processor 194 or between the contacts 194a of the processor 194.

Counter mechanism 190 is actuated by nub 140e formed in drive channel 140. In use, as seen in FIG. 36, as drive channel 140 is driven forward, nub 140e thereof engages contact 194a causing contact 194a to complete a circuit and trigger processor 194 to perform a function (e.g., reduce the number appearing on display 192 by a give increment or value).

Figure 1C:
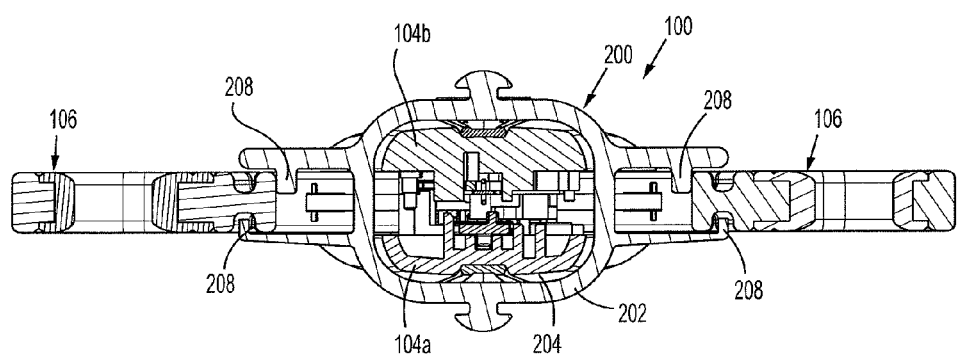
FIG. 1C is a cross-sectional view as taken through 1C-1C of FIG. 1A.
Figure 2:
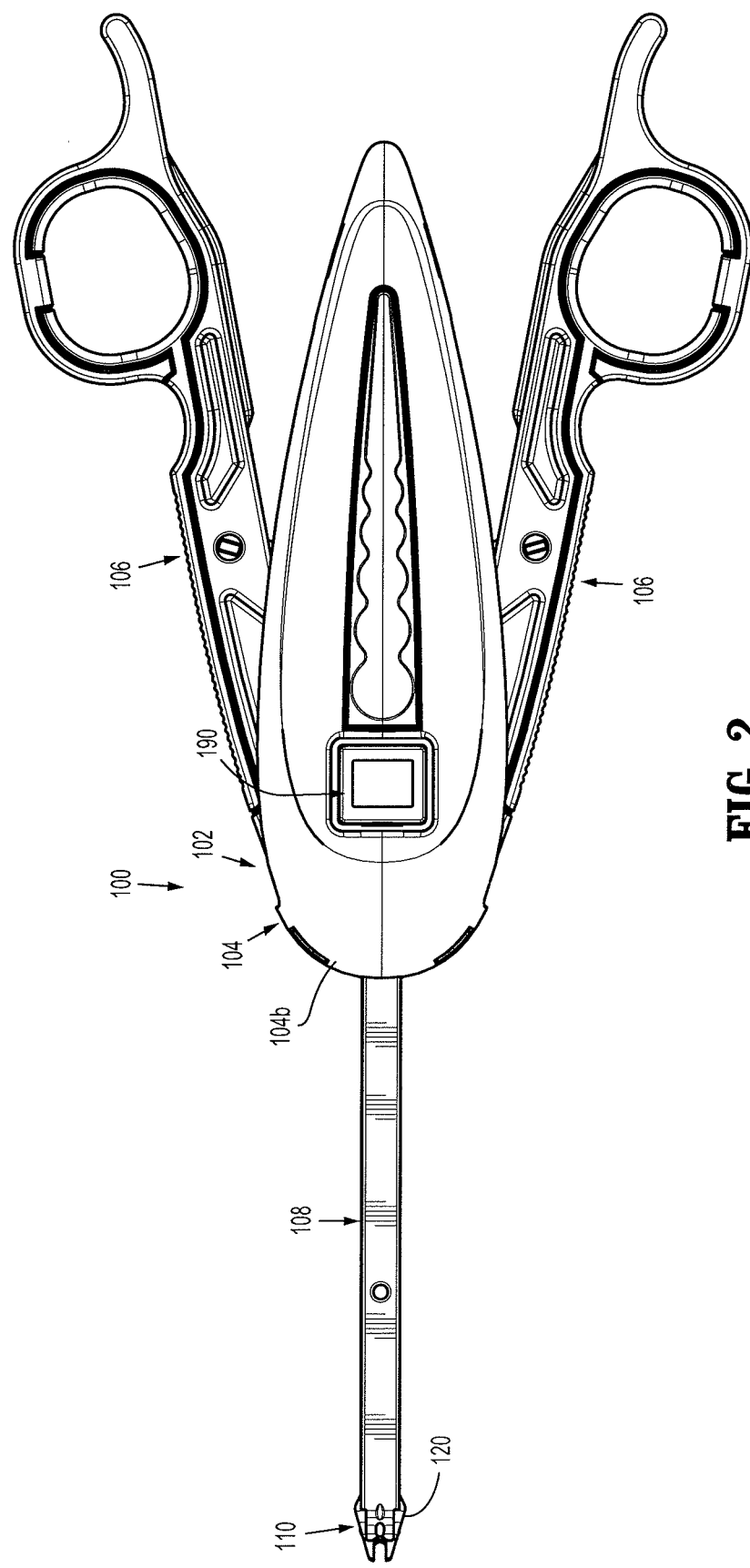
FIG. 2 is a top, plan view of the surgical clip applier of FIG. 1.
Figure 3:
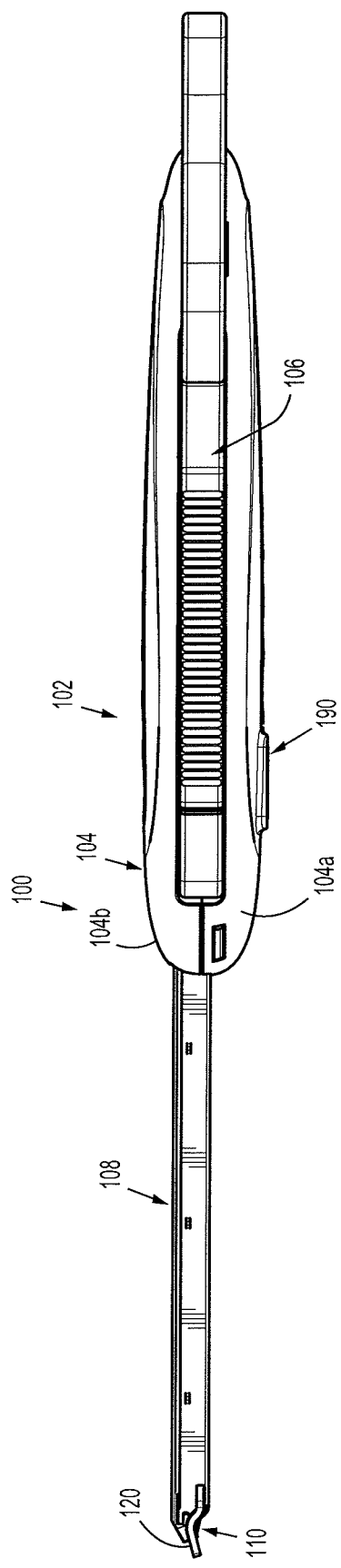
FIG. 3 is a side, elevational view of the surgical clip applier of FIGS. 1 and 2.

As seen in FIGS. 1A and 1C, clip applier 100 includes a shipping wedge 200 supported on housing 104 and interposed between handles 106. Shipping wedge 200 functions to maintain handles 106 spaced apart or un-squeezed during a shipment and/or storage of clip applier 100. Shipping wedge 200 is connected to tab 192a of counter mechanism 190, such that in order for an end user to use clip applier 100, the end user must remove shipping wedge 200 thereby also removing tab 192a to activate counter mechanism 190.

As seen in FIGS. 1A and 1C, shipping wedge 200 includes a body portion 202 in the form of a collar, defining a passage 204 configured and dimensioned for receipt of a portion of housing 104 therein. Shipping wedge 200 includes uprights 206 extending outwardly from opposed sides of body portion 202 and being configured to receive handles 106 therein.

Shipping wedge 200 further includes tabs 208 extending inwardly from opposed sides of uprights 206. Tabs 208 of shipping wedge 200 are configured and dimensioned to engage with handles 106 when shipping wedge 200 is properly secured to clip applier 100.

Figure 22:
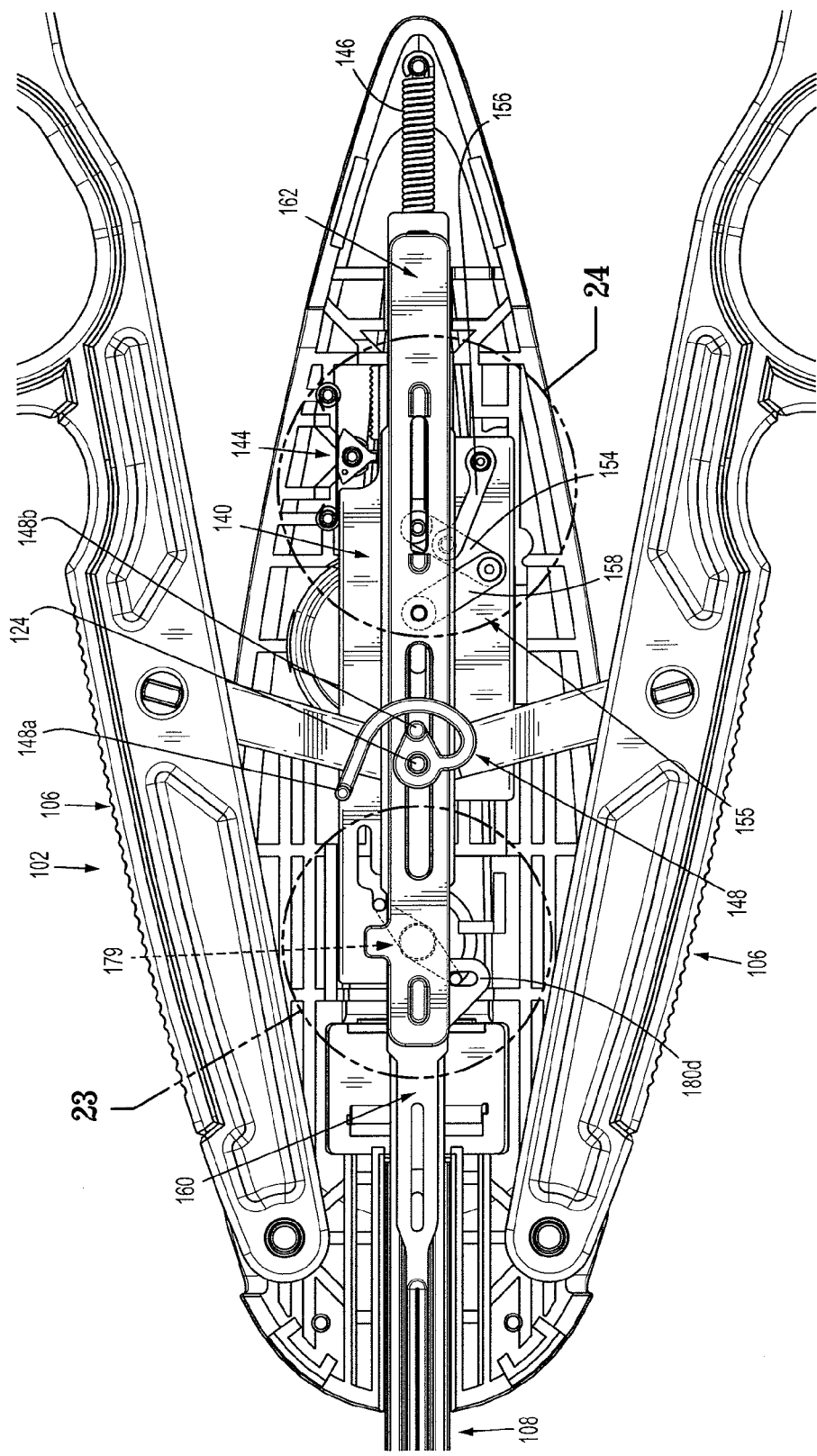
FIG. 22 is a top, plan view of the surgical clip applier of FIGS. 1-4, with the upper housing half removed therefrom and shown in an un-actuated condition.
Figure 23:
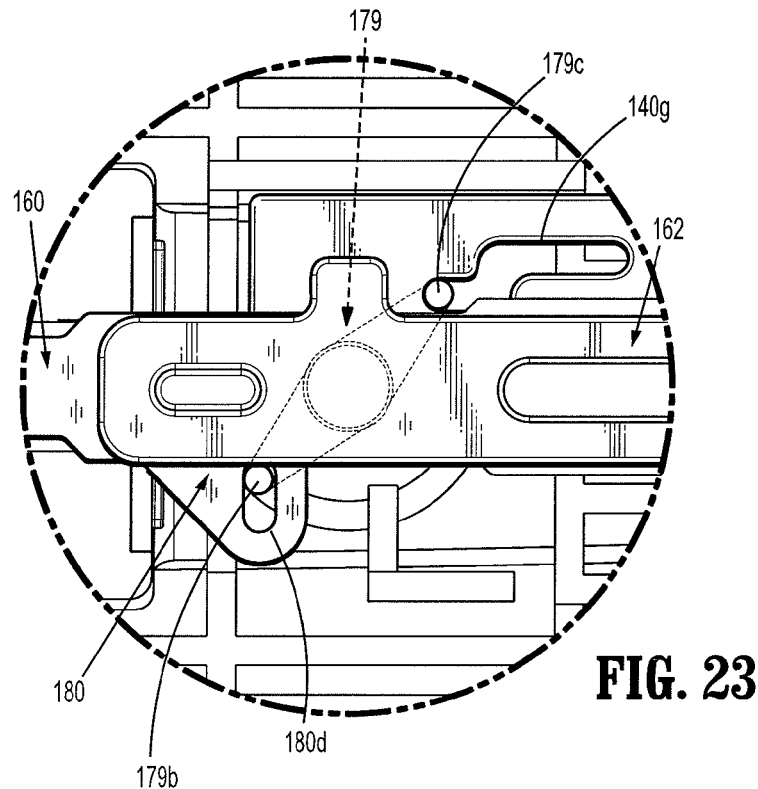
FIG. 23 is an enlarged view of the indicated area of detail of FIG. 22.

With reference to FIGS. 22-53, the operation of clip applier 100 is provided. Prior to any initial squeezing of handles 106 of clip applier 100, as seen in FIGS. 22-24, the internal components of the clip applier 100 are in a so-called "home" position or "starting" position. More particularly, in the "home" position, the drive pin 124 is located at a proximal-most position, pawl 142 is located distal of rack 140d of drive channel 140, second finger 179c of pivot arm 179 is located at a distal-most position in the distal portion of window 140g of drive channel 140 such that wedge plate 180 is located at a distal-most position, and no clips "C" are positioned within jaws 120. Since drive pin 124 is at a proximal-most position, pusher bar 160, stabilizer 162, and drive channel 140 are also at a proximal-most position.

As seen in FIG. 24, when drive channel 140 and pusher bar 160 are located at the proximal-most position, driving post 156c of pivoting drive arm 156 is located at a proximal-most position and second resilient finger 148b of indicator 148 is disposed proximal of edge 149 formed in lower housing half 104b. In embodiments, edge 149 may be formed in upper housing half 104a with slight modification to indicator 148. In the "home" position, angle "α" of proximal linkage member 154 may range from about 45° to about 60°, while angle "β" of pivoting drive arm 156 may range from about 20° to about 25°. Also, prior to an initial squeezing of handles 106 of clip applier 100, with wedge plate 180 located at a distal-most position, distal end 180a thereof is interposed between jaws 120.

Figure 24A:
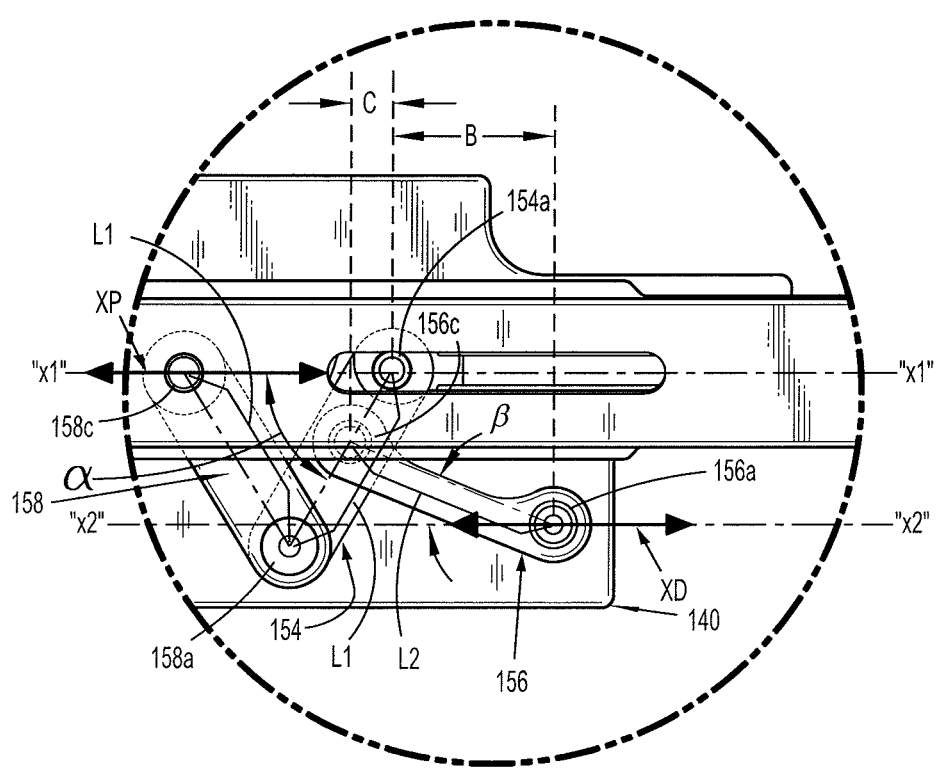
FIG. 24A is a schematic illustration of the motion multiplier system of FIG. 24.
Figure 26:
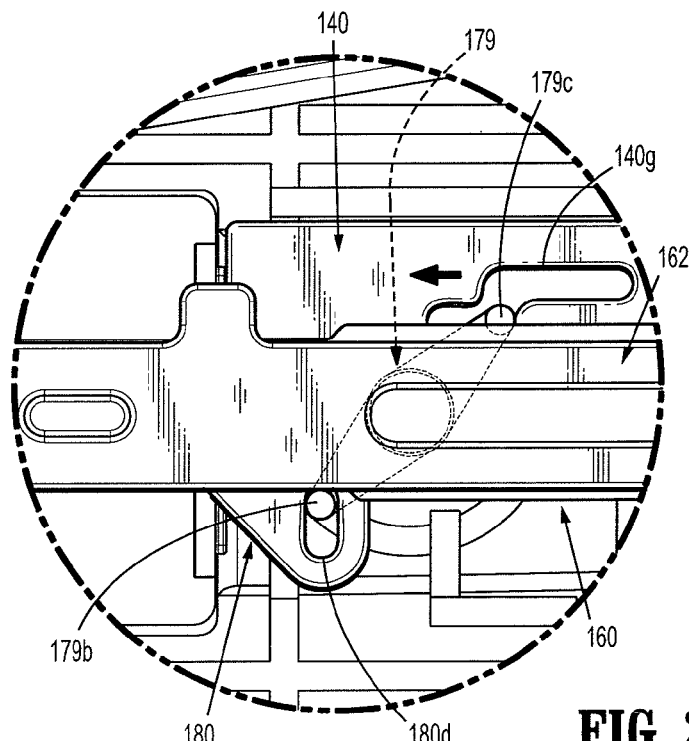
FIG. 26 is an enlarged view of the indicated area of detail of FIG. 25.

As seen in FIGS. 22, 24 and 24A, also in the "home" position coupling pin 158a of distal linkage member 158 is located on a first side of the longitudinal axis "X1."

The following equations are used to calculate the mechanics of the motion multiplier system 155 in a "home" position. The "home" position directly relates to when pusher bar 160 is in the "home" position (i.e., proximal-most position), for example, when "α" is about 60°.

$$XP=(2)(L1)(\cos \alpha)-(L1) \quad (1)$$

where distance "XP" is the distance traveled by sliding post 158c and length "L1" is the length of proximal and distal linkage members 154 and 156, as shown in FIG. 24A.

$$XD=(B)+(C)(\cos \alpha)-(L2)(\cos \beta) \quad (2)$$

where distance "XD" is the distance traveled by pivot post 156a of pivoting drive arm 156 along longitudinal axis "X2," distance "B" is distance between pivot pin 156a of pivoting drive arm 156 and fixed rod 154a of proximal linkage member 154 taken along the longitudinal axis of "X1," distance "C" is the distance between fixed rod 154a of proximal linkage member 154 and driving post 156c of pivoting drive aim 156, and length "L2" is the length of pivoting drive arm 156 taken from pivot post 156a to driving post 156c, as shown in FIG. 24A.

Also prior to the initial squeeze, there are no clips "C" present within jaws 120. A clip "C" is first loaded into jaws 120 during the initial squeezing of handles 106. As seen in FIGS. 25-33, during an initial squeeze of handles 106 (i.e., a working stroke), distal ends 122a of link members 122 are moved distally relative to housing 104. As distal ends 122a of link members 122 are moved distally, drive pin 124 is moved distally thereby transmitting distal axial movement to drive channel 140.

Subsequently, as seen in FIGS. 25-31, as drive channel 140 is moved distally, motion multiplier system 155 moves from the "home" position to an initial actuated position. More particularly, drive channel 140 advances in a distal direction, which, in turn, causes pivoting drive arm 156 to move in a distal direction. That is, pivoting drive arm 156 pivots and drives proximal linkage member 154 to rotate in a direction such that angle "β" increases, for example, but not limited from about 22° to about 45°. In this manner, when angle "β" is increased, proximal linkage member 154 is rotated about fixed rod 154a of proximal linkage member 154, which, in turn, causes driving post 158c of distal linkage member 158 to be driven distally along slot 162b of stabilizer 162 and proximal window 160d of pusher bar 160. As driving post 158c of distal linkage member 158 is driven distally, driving post 158c of distal linkage member 158 drives pusher bar 160 in a distal direction.

Figure 32:
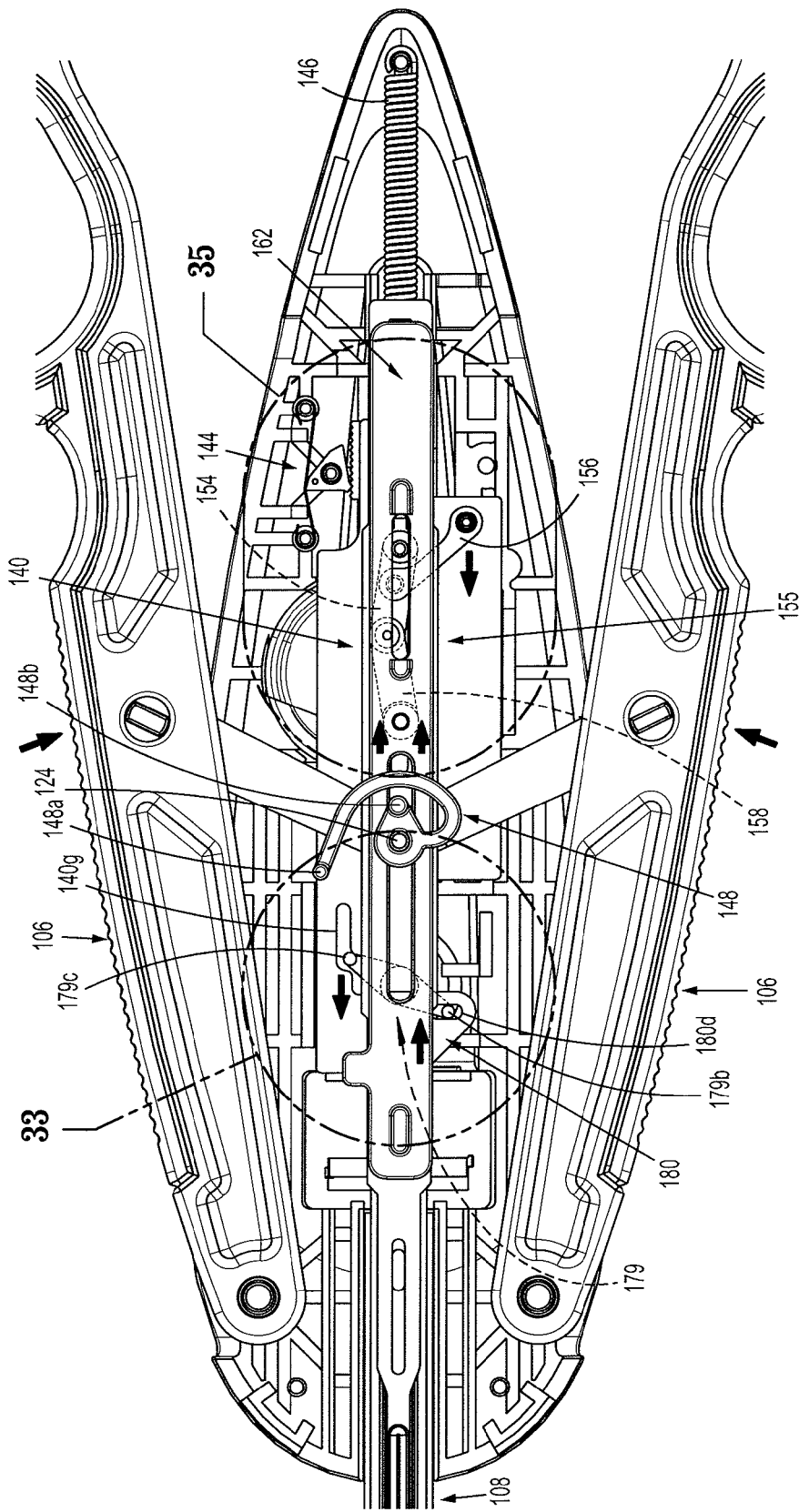
FIG. 32 is a top, plan view of the surgical clip applier of FIGS. 1-4, with the upper housing half removed therefrom and shown during a further actuation of the surgical clip applier.
Figure 33:
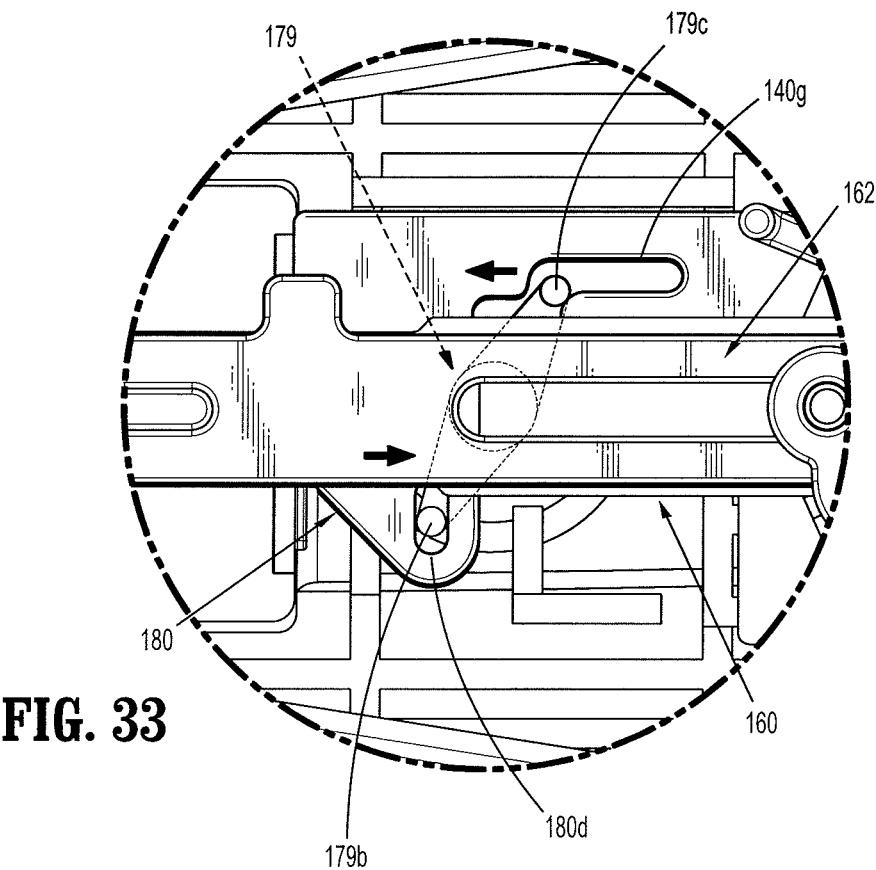
FIG. 33 is an enlarged view of the indicated area of detail of FIG. 32.
Figure 34:
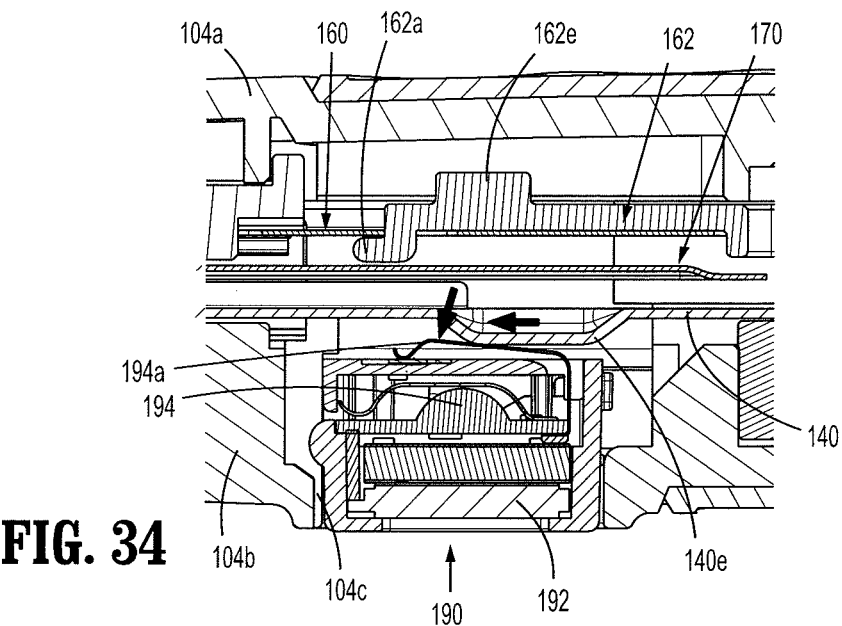
FIG. 34 is an enlarged, cross-sectional view illustrating an actuation of a counter mechanism of the surgical clip applier of FIGS. 1-4.

As seen in FIGS. 25, 32 and 33, during the initial squeeze of handles 106, indicator 148 is moved distally along with the distal movement of drive channel 140. In use, indicator 148 functions to create an audible click and/or a tactile vibration, thereby indicating to the user that handles 106 of surgical clip applier 100 have gone through at least a portion of a stroke. In particular, as seen in FIGS. 32 and 33, as handles 106 are actuated, first resilient arm 148a of audible/tactile indicator 148 rides over and/or along a ledge 149 formed in at least one of upper and lower housing halves 104a, 104b and is flexed thereby. As arm 148a of audible/tactile indicator 148 reaches the proximal end of ledge 149, resilient arm 148a snaps over the proximal end of ledge 149 and comes into contact with a surface 149a of ledge 149, thereby creating a first audible sound and a tactile vibration as resilient arm 148a comes into contact with surface 149a of ledge 149. The first indication of audible/tactile indicator 148 indicates to the user that a clip "C" has been appropriately loaded.

Figure 30:
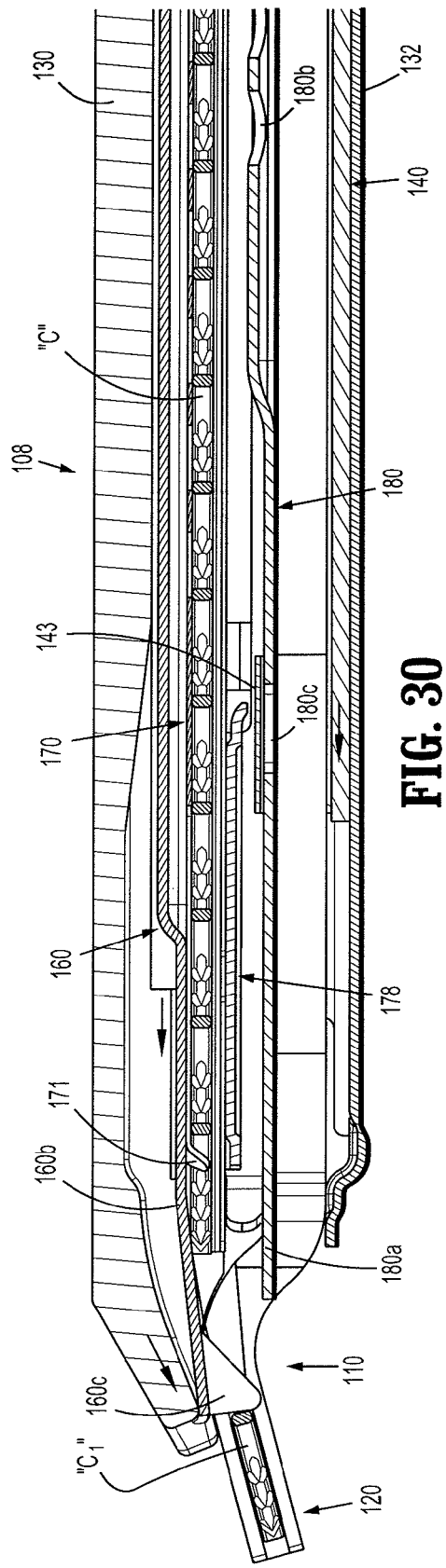
FIG. 30 is an enlarged, longitudinal cross-sectional view of the distal end of the channel assembly during a further initial actuation of the surgical clip applier.

As seen in FIGS. 28 and 30, also during the initial squeeze of handles 106, as pusher bar 160 is moved in a distal direction, pusher 160c thereof engages a backspan of a distal-most clip "C1" and begins to move or urge distal-most clip "C1" distally out of clip carrier 170 and into jaws 120. As distal-most clip "C1" is moved distally, tangs 171 of clip carrier 170 are deflected or cammed out of engagement with distal-most clip "C1" and return to their un-deflected or un-cammed state to capture a subsequent clip of the stack of clips "C". During the initial squeeze of handles 106, pusher bar 160 is advanced an amount sufficient to place distal-most clip "C1" in channels 120a of jaws 120.

Figure 31:
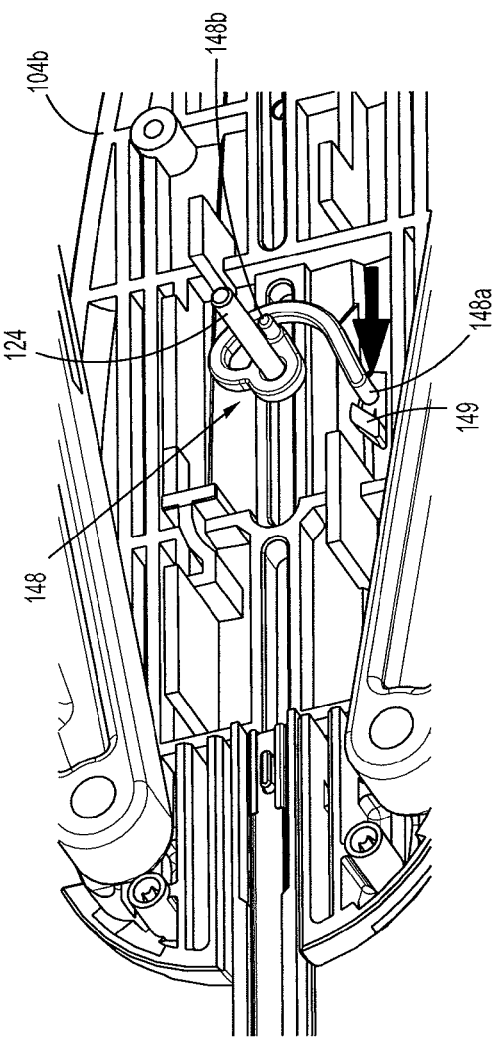
FIG. 31 is bottom, perspective view illustrating the operation of an audible/tactile indicator during the respective initial actuation of the surgical clip applier of FIGS. 1-4.

As seen in FIGS. 27 and 31, also during the initial squeeze of handles 106, as drive channel 140 is moved in a distal direction, rack member 141 of ratchet mechanism 144 is moved distally causing teeth 141a thereof to move into engagement with and over or across a tooth of pawl 142. Once rack member 141 of ratchet mechanism 144 is moved into engagement with pawl 142, drive channel 140 can not return to a home or proximal-most position until rack member 141 has cleared pawl 142.

During the initial squeeze of handles 106, as seen in FIGS. 25-33, drive channel 140 is moved distally until finger 179c of pivot arm 179 is engaged by the transverse portion of slot 140g of drive channel 140 (i.e., the dwell). Once the transverse portion of slot 140g is in abutment with finger 179c of pivot arm 179 (i.e., after the dwell has been exhausted), further distal movement of drive channel 140 causes finger 179c to move and rotate pivot arm 179. Rotation of pivot arm 179 causes movement of finger 179b thereof which, in turn, causes wedge plate 180 to be pulled in a proximal direction, thereby withdrawing distal end 180a thereof from between jaws 120 and allowing for jaws 120 to eventually be closed or approximated thus allowing for jaws 120 to eventually be closed or approximated.

Once the required rotation of pivot arm 179 is achieved, pivot arm 179 stops rotating as finger 179c of pivot arm 179 rides through the proximal portion of slot 140g of drive channel 140. Finger 179c of pivot arm 179 remains in the proximal portion of slot 140g of drive channel 140 until the stroke of drive channel 140 is completed.

As seen in FIGS. 25-31, during a further squeeze of handles 106, pusher bar 160 is moved distally with drive channel 140, as described above, until pivoting drive arm 156 has reached a position, such that angle "β" is 45°. In this configuration, proximal and distal linkage members 154 and 158 are aligned along longitudinal axis "X1" such that angle "α" therebetween is about 0°.

Figure 27A:
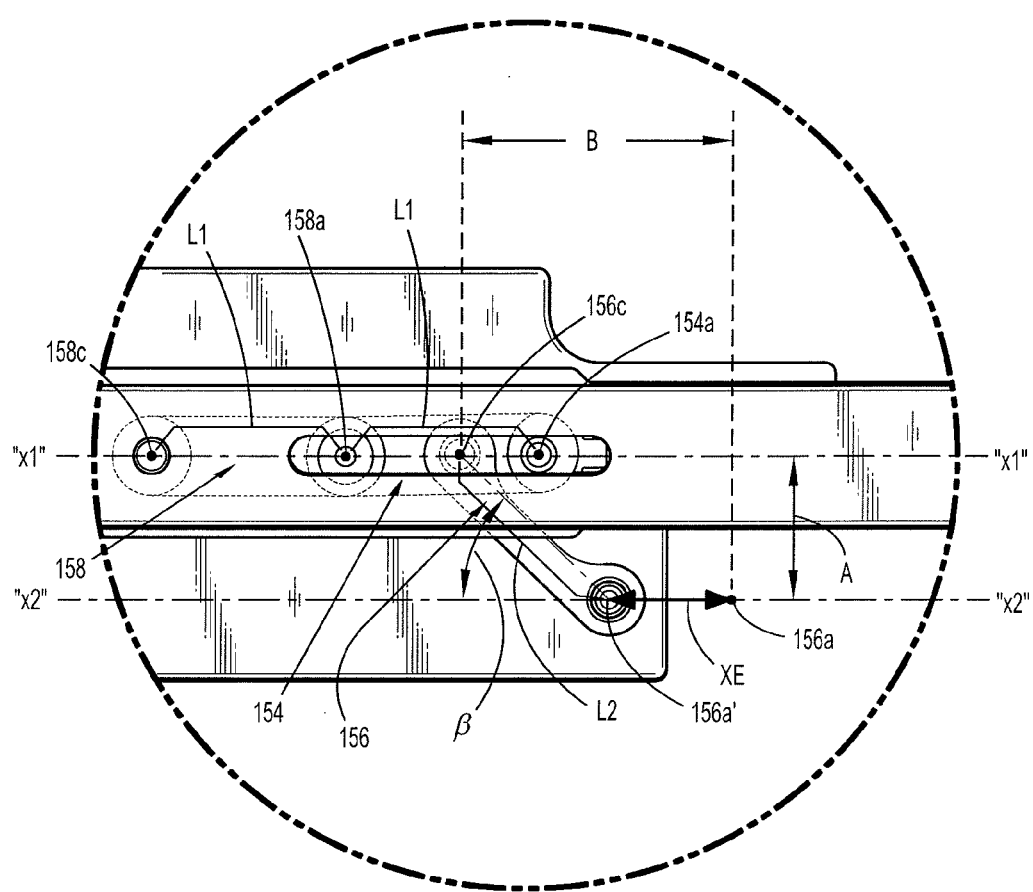
FIG. 27A is a schematic illustration of the motion multiplier system of FIG. 27.

The following equation is used to calculate the mechanics of the motion multiplier system 155 when in a "fully extended" position. The "fully extended" position directly relates to when pusher bar 160 is in a "fully extended" position (i.e., distal-most position), for example, when angle "α" is about 0°.

$$XE=(B)+(C)-(L2)(\cos \beta_0) \quad (3)$$

where distance "XE" is the distance between the "home" position of pivot pin 156a of pivoting drive arm 156 and the "fully extended" position of pivot pin 156a of pivoting drive arm 156 taken along longitudinal axis "X2" of drive channel 140, distance "B" is the distance between pivot pin 156a of pivoting drive arm 156 and fixed rod 154a of proximal linkage member 154 taken along longitudinal axis "X1", distance "C" is the distance between coupling pin 158c of distal linkage member 158 and driving post 156c of pivoting drive arm 156, length "L2" is the length of pivoting drive arm 156 taken from pivot post 156a to driving post 156c, and angle "$\beta_0$" is the "fully extended" position angle of angle "β" when angle "α" is about 0°. In this case, angle "$\beta_0$" of pivoting drive arm 156 is about 45°, as described above and shown in FIG. 27A.

As seen in FIG. 31, as drive channel 140 is further advanced distally, drive channel 140 pulls or flexes resilient finger 148a of indicator 148 over a proximal end of ledge 149. In this manner, a first indication (i.e., audible and/or tactile) is created indicating to a user that a surgical clip "C" has been appropriately loaded.

As seen in FIGS. 25 and 27, also in the "fully extended" position, proximal and distal linkage member 154 and 158 are aligned and/or parallel with longitudinal axis "X1."

Referring now to FIGS. 32-35, during a further squeezing of handles 106, distal ends 122a of link members 122 are caused to be moved further distally relative to housing 104. As distal ends 122a of link members 122 are moved further distally, drive pin 124 is caused to be moved further distally thereby transmitting distal axial movement to drive channel 140.

As seen in FIGS. 32, 33, and 35, as handles 106 are continuously squeezed, pivoting drive arm 156 continues to move in a distal direction such that angle "β", between pivoting drive arm 156 and longitudinal axis "X2" of drive channel 140, continuously increases as drive channel 140 moves in the distal direction to about 90°. This movement also causes proximal linkage member 154 (i.e., positioned on the first side) to pivot or move over-center to the second side, with reference to longitudinal axis "X1", such that angle between proximal linkage member 154 is pivotally oriented at an angle "−α" relative to longitudinal axis "X1" (as shown in FIG. 35). In this manner, as proximal linkage member 154 rotates about longitudinal axis "X1," angle "−α" decreases from about 0° to about 60° causing distal linkage member 158 to move in a proximal direction. In this configuration, sliding post 158c of distal linkage member 158 slides in a proximal direction, which, in turn, slides pusher bar 160 and stabilizer 162 back to a retracted position or a "safe" position. In the "safe" position, other components of clip applier 100, such as drive bar 140, are still moving in a distal direction so that clip "C" may be formed between jaw members 120. However, in the "safe" position, pusher bar 160 is safely retracted to a proximal position such that pusher bar 160 does not interfere with clip applier 100 when jaw members 120 are approximated towards one another.

The following equation is used to calculate the mechanics of the motion multiplier system 155 when in a "safe" position. The "safe" position, as discussed above, directly relates to when pusher bar 160 is in a safe retracted position (i.e., proximal-most position), while other components of clip applier 100, for example, handles 106 are still in a working stroke.

$$(L2)-(C)(\sin(-\alpha))=A \quad (4)$$

where length "L2" is the length of pivoting drive arm 156 taken from pivot post 156a to driving post 156c, distance "C" is the distance between coupling pin 158c of distal linkage member 158 and driving post 156c of pivoting drive arm 156 taken along the longitudinal axis "X1," and distance "A" is the distance between fixed rod 154a of proximal linkage member 154 and pivot pin 156a of pivoting drive arm 156 taken along a reference axis orthogonal to the longitudinal axis "X1," as shown in FIG. 42B.

With continued reference to FIG. 32-38, during the further squeezing of handles 106, with tab 192a removed from counter mechanism 190, as drive channel 140 is advanced distally, nub 140e thereof engages contact 194a of processor 194 thereby completing a circuit and causing processor 194 to perform a function, as described above.

Referring now to FIGS. 39-44, clip applier 100 is illustrated during a final squeezing of handles 106. In this condition, drive channel 140 is at a distal position, pusher bar 160 is at a distal position, wedge plate 180 is at a proximal position, biasing member 146 is stretched, and pawl 142 is located proximal of rack 140d.

Figure 43:
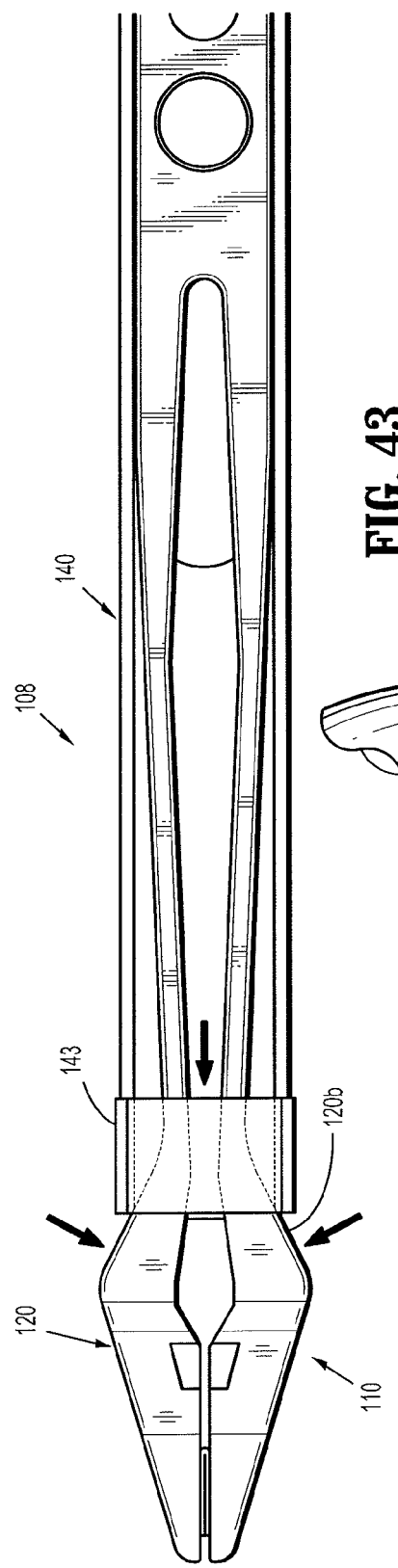
FIG. 43 is a top, plan view of the jaw assembly illustrating the position of the jaw assembly following an actuation of the surgical clip applier of FIGS. 1-4.

Additionally, as seen in FIG. 43, with distal end 180a of wedge plate 180 removed from between jaws 120, as drive channel 140 is moved further distally, a distal edge of drive channel 140 and/or drive channel strap 143 engages against camming surfaces 120b of jaws 120 thus causing jaws 120 to approximate toward one another and to form surgical clip "C1" interposed therebetween. Since drive channel strap 143 is fixed to drive channel 140 and moves therewith, drive channel strap 143 functions to cap drive channel 140 so as to maintain jaws 120 within drive channel 140 during the approximation of jaws 120 and to maintain wedge plate 180 within drive channel 140 during operation of clip applier 100.

Figure 44:
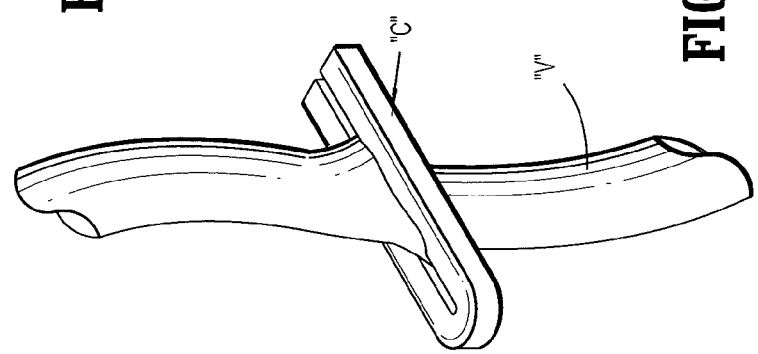
FIG. 44 is a perspective view of a body vessel including a clip of the surgical clip applier, shown applied thereto.
Figure 45:
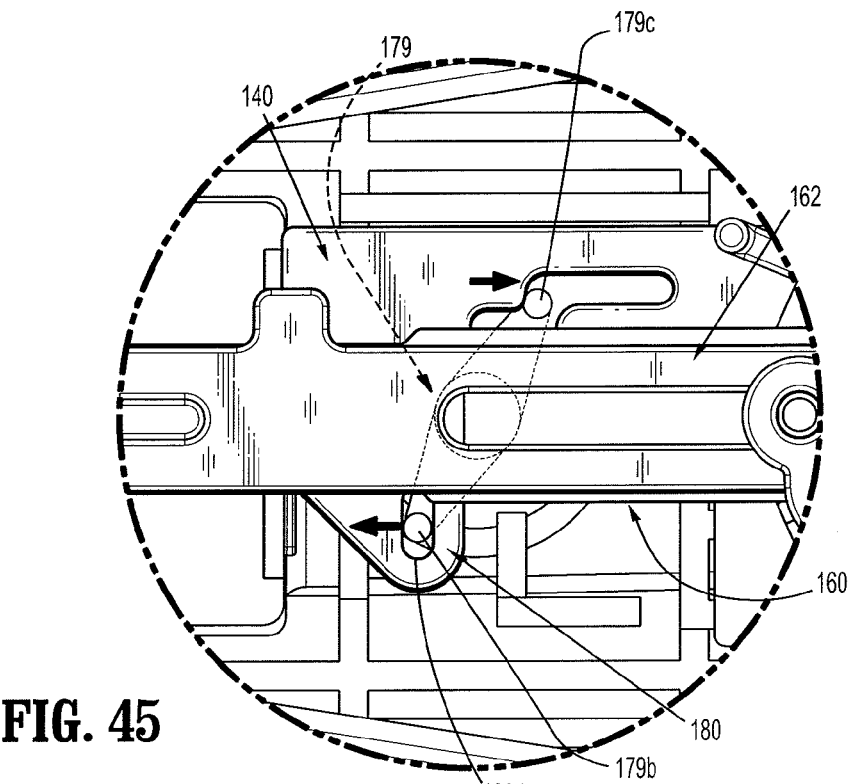
FIG. 45 is an enlarged view of the indicated areas of detail of FIGS. 22, 25, 32, and 39, illustrating the operation of the pivot aim during an opening or release of the surgical clip applier following a complete actuation thereof.
Figure 46:
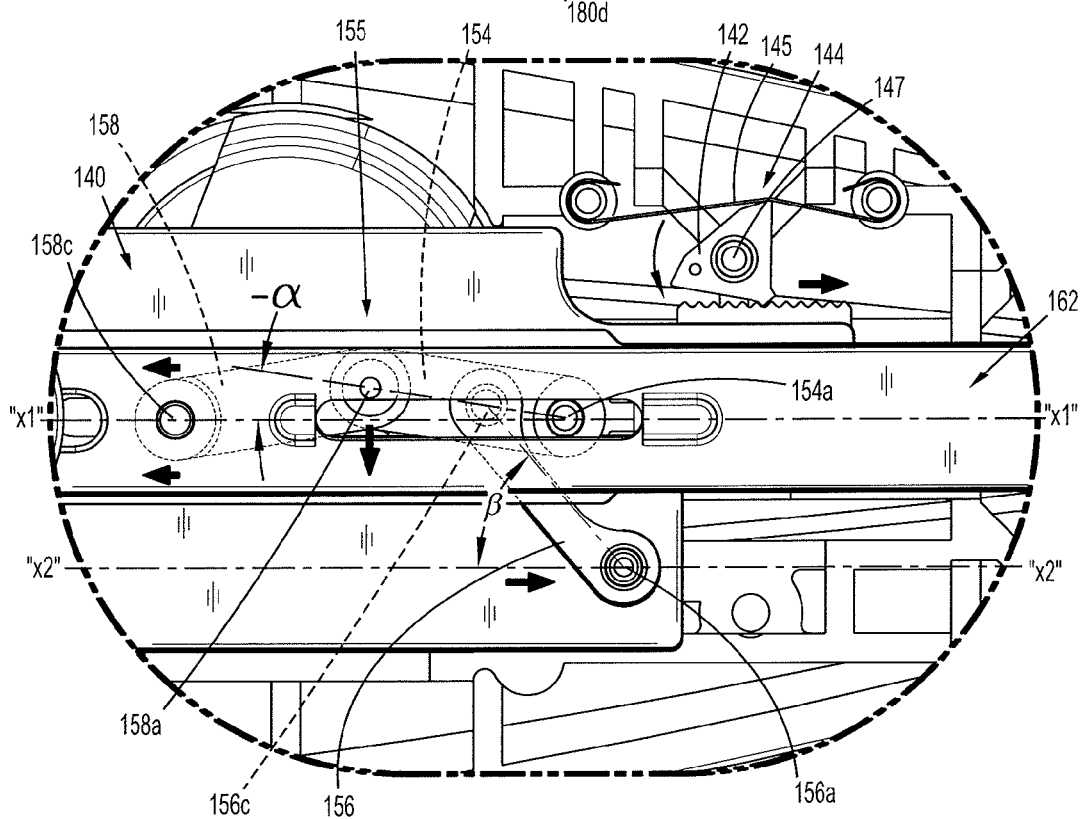
FIG. 46 is an enlarged view of the ratchet mechanism shown during the opening or release of the surgical clip applier of FIGS. 1-4.

As seen in FIG. 44, surgical clip "C1" may be formed or crimped onto a vessel "V" or any other biological tissue.

Drive channel 140 is permitted to move distally relative to pusher bar 160 due to the translation of bosses 148b of indicator 148 through slot 160d of pusher bar 160.

Figure 41:
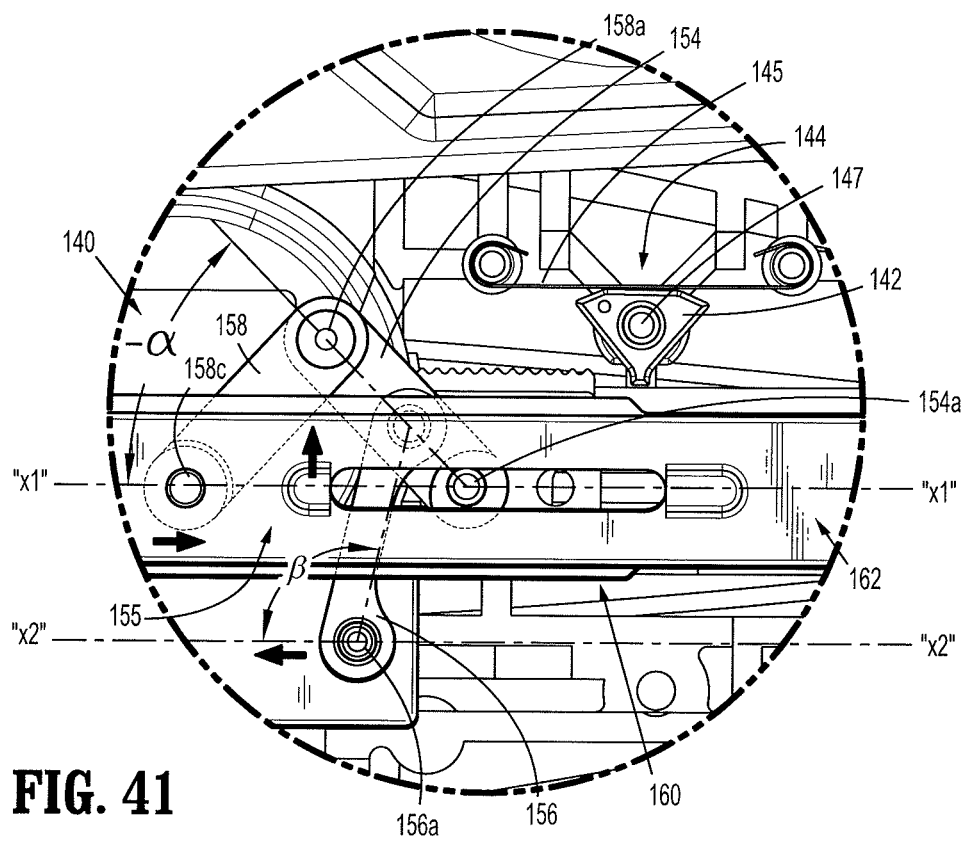
FIG. 41 is an enlarged view of the indicated area of detail of FIG. 39.
Figure 41A:
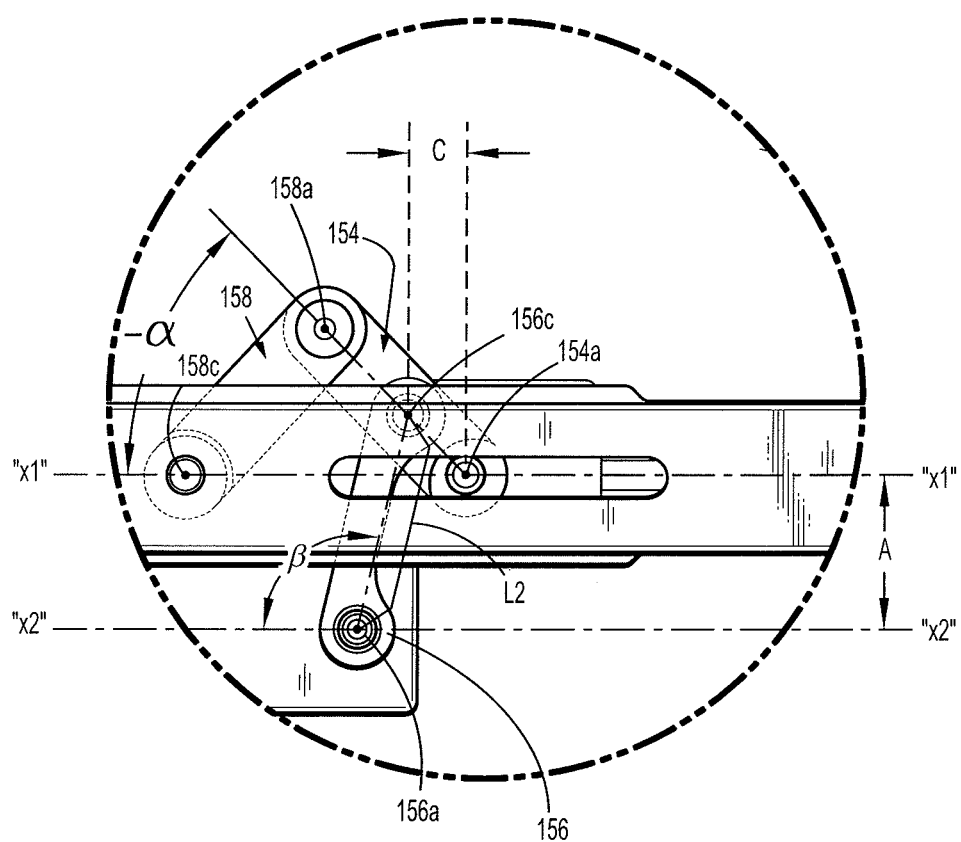
FIG. 41A is a schematic illustration of the motion multiplier system of FIG. 41.

Also, as drive channel 140 is fully advanced distally, as seen in FIG. 41, rack member 141 of ratchet mechanism 144 is moved distally to a location beyond pawl 142 such that the teeth 141a of rack member 141 are moved distally of the tooth of pawl 142 thereby disengaging rack member 141 and pawl 142 from one another. In this manner, drive channel 140 is permitted or free to return to a home or proximal-most position.

Figure 42:
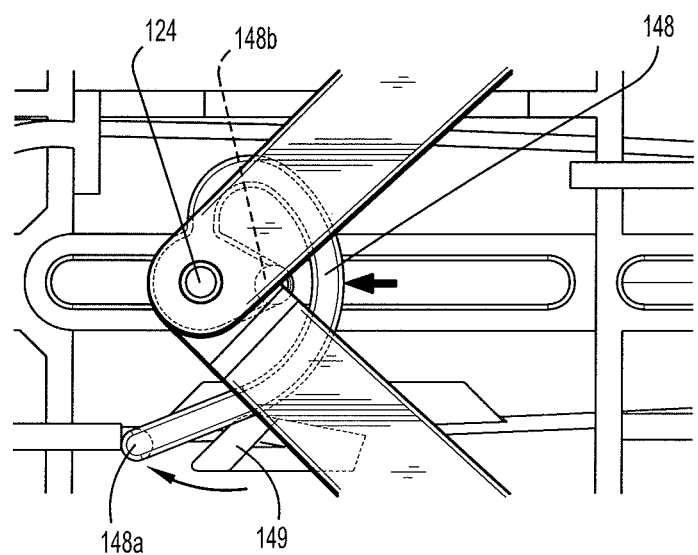
FIG. 42 is an enlarged view illustrating the position of the audible/tactile indicator following an actuation of the surgical clip applier of FIGS. 1-4.

As seen in FIG. 42, as drive channel 140 is moved distally, resilient arm 148a of audible/tactile indicator 148 snaps over the distal end of ledge 149 and comes into contact with a surface 149a of ledge 149, thereby creating an audible sound and/or a tactile vibration. Such audible sound and/or tactile vibration coincide with the loading of surgical clip "C".

Referring now to FIGS. 45-52, during an opening or release of handles 106, distal ends 122a of link members 122 are caused to be moved proximally relative to housing 104. As distal ends 122a of link members 122 are moved proximally, drive pin 124 is caused to be moved proximally thereby transmitting proximal axial movement to drive channel 140 and, in turn, pusher bar 160. The proximal movement of drive channel 140 is facilitated by the constriction of biasing members 146. Alternatively, the release of handles 106 results in biasing member 146 withdrawing drive channel 140 in a proximal direction.

As drive channel 140 is moved proximally, the distal edge of drive channel 140 and/or drive channel strap 143 disengages from against camming surfaces 120b of jaws 120 thus freeing jaws 120 for separation from one another for reinsertion of distal end 180a of wedge plate 180 therebetween, and to receive another surgical clip "C" therebetween. In particular, as drive channel 140 is moved proximally, the transverse portion of slot 140g acts on finger 179c to cause pivot arm 179 to rotate and cause finger 179b of pivot arm 179 to urge wedge plate 180 distally. As wedge plate 180 is moved in a distal direction, as seen in FIGS. 51 and 52, distal end 180a of wedge plate 180 is reinserted or reintroduced into jaws 120, thereby spreading jaws 120 apart.

Figure 50:
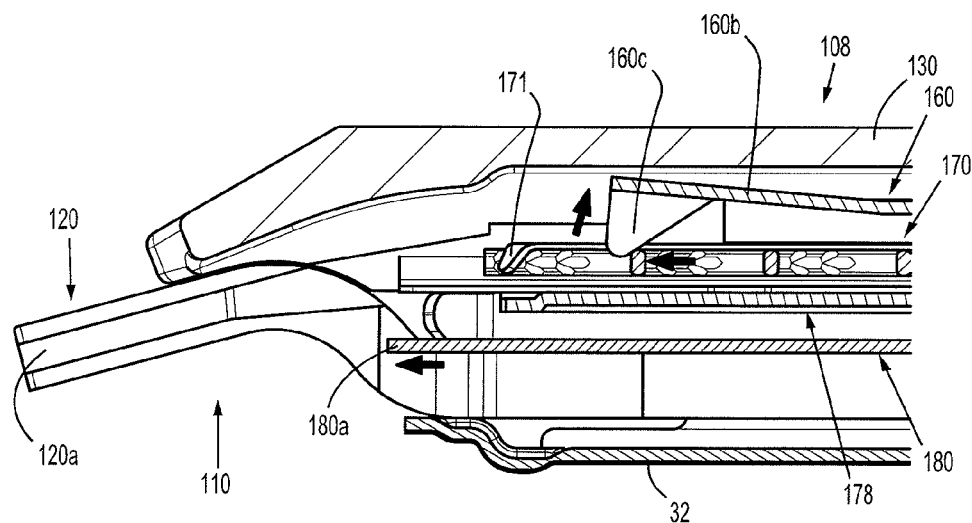
FIGS. 50 and 51 are longitudinal, cross-sectional views of the distal end of the channel assembly illustrating the movement of the pusher bar and wedge plate during the opening or release of the surgical clip applier of FIGS. 1-4.

As seen in FIGS. 48 and 49, as wedge plate 180 is moved distally, proximal tab 176 of clip follower 174 engages in a window 180b of wedge plate 180 and is thus urged distally a given distance. As clip follower 174 is urged distally, stack of clips "C" is also urged distally. As seen in FIG. 50, when wedge plate 180 reaches a distal-most position, clip channel 170 abuts, engages, urges or otherwise cams against proximal portion 175b of distal tab 175 until web 180f of wedge plate 180 rests substantially beneath distal portion 175a of distal tab 175. In so doing, proximal portion 175b of distal tab 175 is moved to extend into an incrementally more distal window 172 of clip channel 170.

Figure 51:
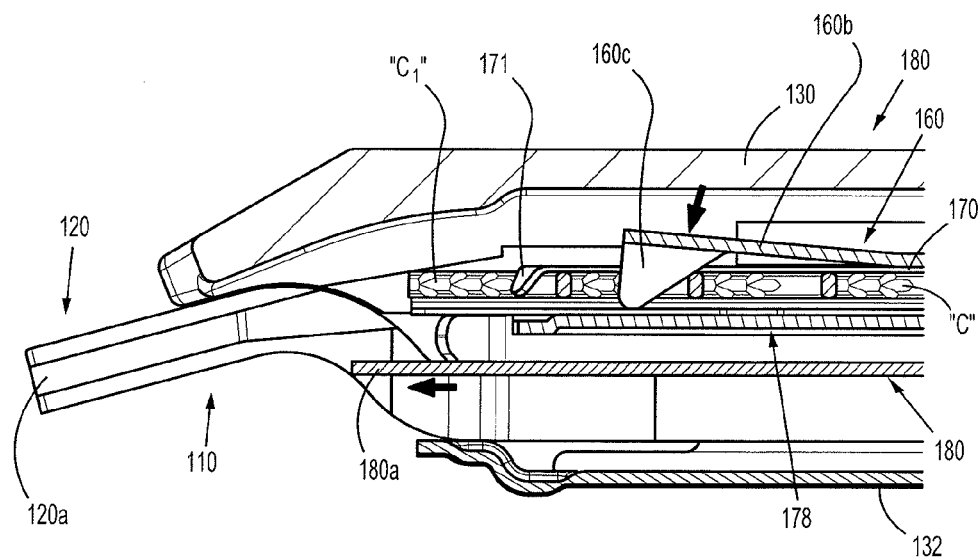
Figure 52:
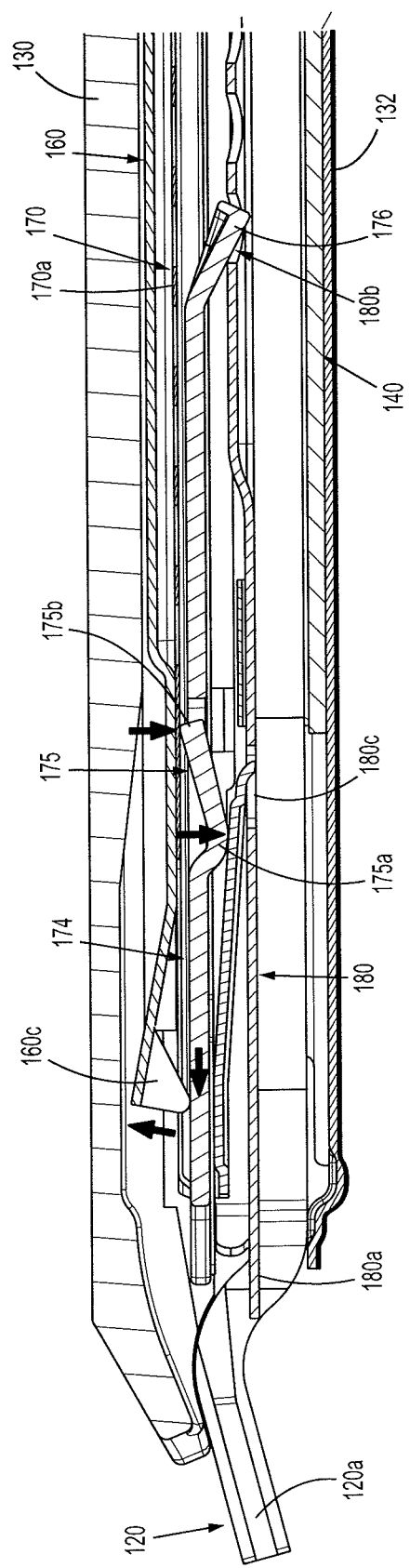
FIG. 52 is a longitudinal, cross-sectional view of the distal end of the channel assembly illustrating the surgical clip applier of FIGS. 1-4 in a locked-out condition following firing of the last surgical clip therefrom.

As seen in FIGS. 50 and 51, as clip follower 174 is urged forward, moving the stack of clips "C" forward, a distal-most clip "C1" moves distal of pusher 160c by camming beneath pusher 160c of pusher bar 160 until distal-most clip "C1" is caught by tangs 171 of clip applier 170.

Figure 47:
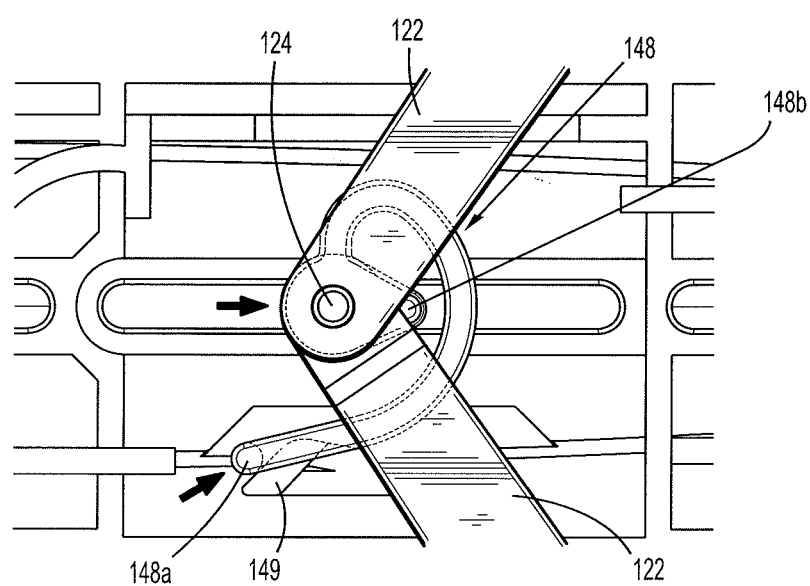
FIG. 47 is an enlarged view illustrating the operation of the audible/tactile indicator during the opening or release of the surgical clip applier of FIGS. 1-4.

Turning momentarily to FIG. 47, as drive channel 140 is moved in a proximal direction, arm 148a of audible/tactile indicator 148 snaps back over ledge 149 and re-sets itself for the next firing stroke or squeeze of handles 106.

As drive channel 140 is moved further in a proximal direction, drive channel 140 effectuates proximal movement of pivoting drive arm 156, which, in turn, reverses the movement of the motion multiplier system.

Figure 39:
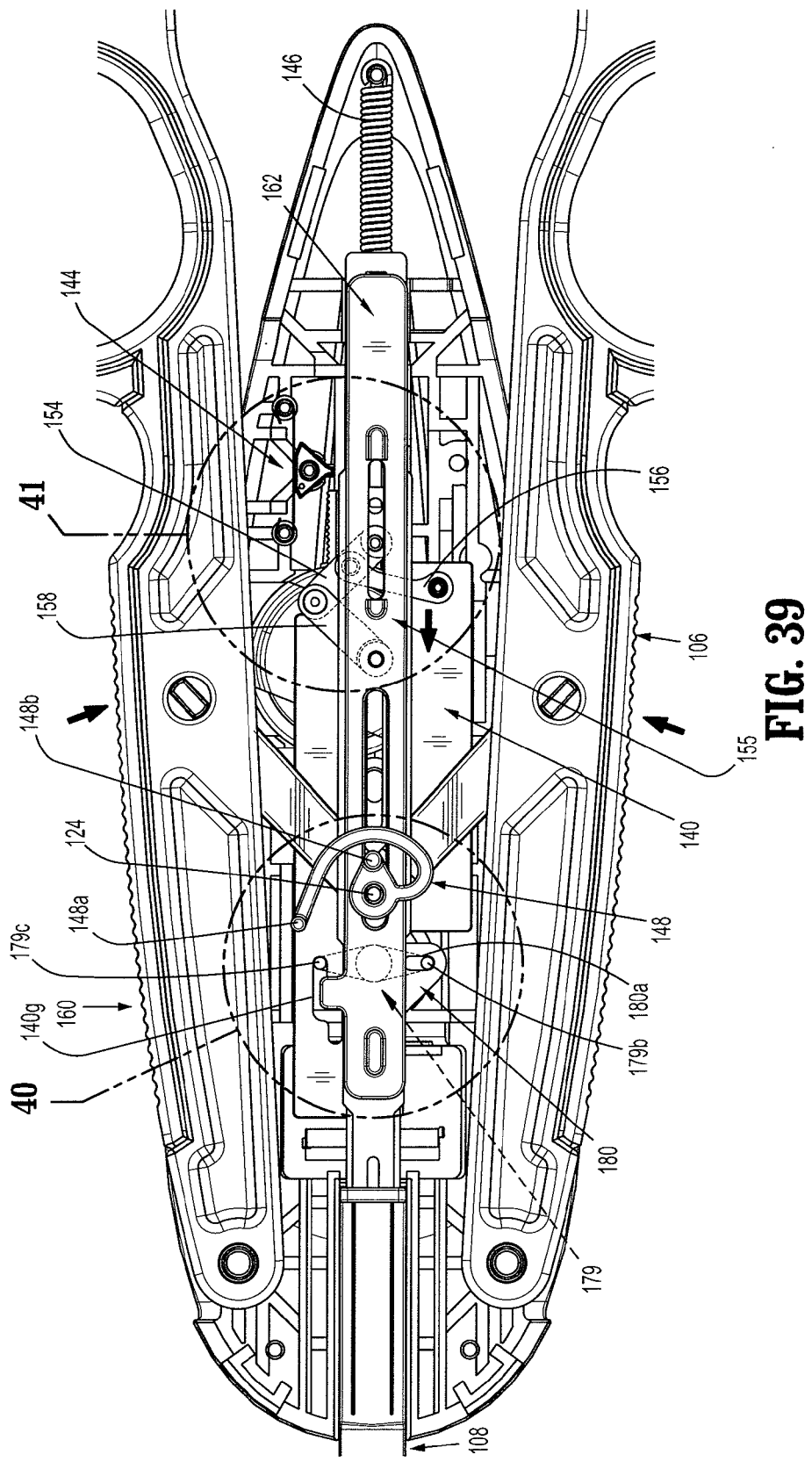
FIG. 39 is a top, plan view of the surgical clip applier of FIGS. 1-4, with the upper housing half removed therefrom and shown at a final condition after an actuation of the surgical clip applier.
Figure 40:
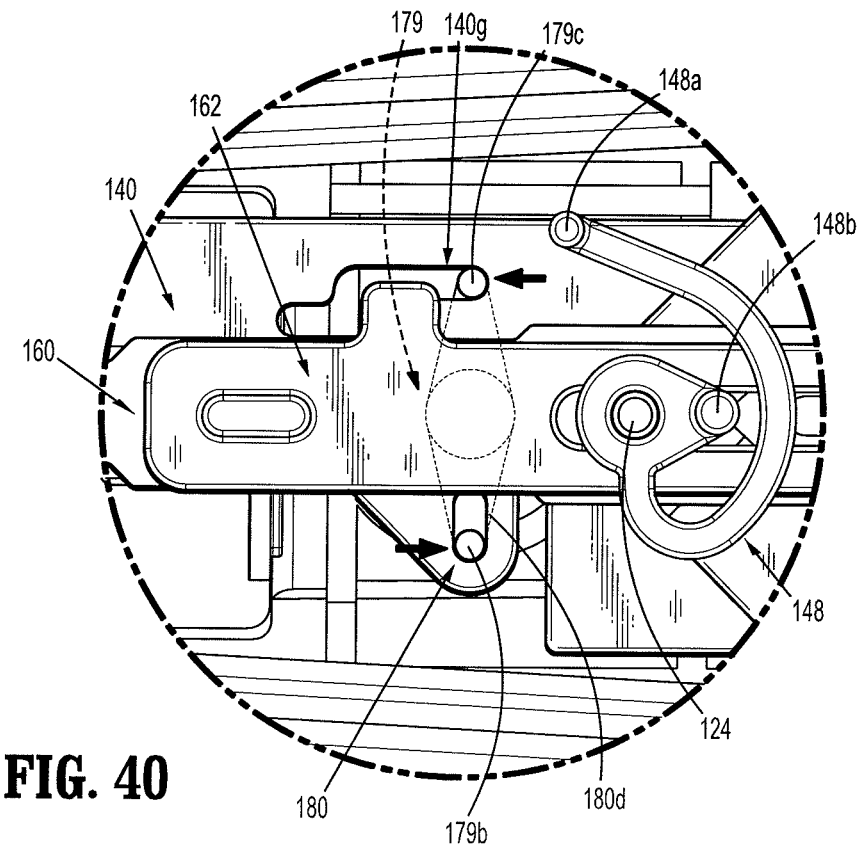
FIG. 40 is an enlarged view of the indicated area of detail of FIG. 39.

As seen in FIGS. 45-51, while handles 106 are released and driving channel 140 is moved in a proximal direction via biasing member 146 (as shown in FIG. 39), coupling pin 156a of pivoting drive arm 156 moves in a proximal direction such that angle "β," between pivoting drive arm 156 and longitudinal axis "X2" of drive channel 140, continuously decreases as drive channel 140 also moves in the proximal direction. In this manner, driving post 158c of distal linkage member 158 starts to move in a distal direction, such that, pusher bar 160 and stabilizer 162 via sliding post 158c distally move back to the "fully extended" position. At substantially the same time, as driving post 158c of distal linkage member 158 starts to move in a distal direction, angle "−α" of proximal linkage member 154, positioned on the second side of longitudinal axis "X1," increases from about −60° to about 0°. As drive channel 140 further moves in the proximal direction, proximal linkage member 154 pivots from the second side to the first side of longitudinal axis "X1," such that, in the "fully extended" position, proximal and distal linkage members 154 and 158 are again pivotally located in alignment with each other, such that angle "α" is about 0°. In other words, proximal and distal linkage member 154 and 158 are between the first side and the second side of longitudinal axis "X1."

In this configuration, as driving channel is 140 further continues to move in the proximal direction, pusher bar 160 is moved proximally with drive channel 140, as described above, until pivoting drive aim 156 has reached a position, such that angle "β," between pivoting drive arm 156 and longitudinal axis "X2" of drive channel 140, is about 45°. In this manner, proximal linkage member 154 moves to the first side, such that angle "α" starts to increase from about 0° to about 60°.

Subsequently, as drive channel 140 is moved proximally, the reversing motion multiplier system 155 moves from the "fully extended" position to the "home" position. More particularly, drive channel 140 advances in a proximal direction, which, in turn, causes pivoting drive arm 156 to move in a proximal direction. That is, pivoting drive arm 156 pivots and drives proximal linkage member 154 in a direction such that angle "β," between pivoting drive arm 156 and longitudinal axis "X2" of drive channel 140, decreases to about 22° to about 45°. In this manner, proximal linkage member causes distal linkage member to pivotally slide proximally along slot 162b of stabilizer 162 and proximal window 160d of pusher bar 160. In this configuration, distal linkage member 158 drives pusher bar 160 in a proximal direction.

When drive channel 140 and pusher bar 160 are located at the distal-most position, sliding post 156c of pivoting drive arm 156 is located at a distal-most position and second resilient finger 148b of indicator 148 is disposed proximal of edge 149. Also, as handles 106 of clip applier 100 are released, with wedge plate 180 located at a distal-most position, distal end 180a thereof is interposed between jaws 120. Additionally, as drive channel 140 is moved in a proximal direction, nub 140e thereof disengages contact 194a of processor 194.

Turning now to FIG. 52, a distal end of clip applier 100 is illustrated following a complete stroke or squeezing of handles 106 and after a final clip has been expelled therefrom. Following firing of the last clip, as seen in FIG. 52, proximal tab 176 of clip follower is disposed within a distal-most aperture or window of apertures 180b of wedge plate 180. In this manner, as wedge plate 180 is moved distally following a firing of a clip, in the manner described above, clip follower 174 is also moved distally. Accordingly; as clip follower 174 is moved distally, distal tab 175 thereof is moved distal of a distal-most window of windows 172 of clip carrier 170. In this manner, proximal portion 175b of distal tab 175 engages against an inner surface of a top wall of clip carrier 170 and is cammed or urged downwardly.

As proximal portion 175b of distal tab 175 is cammed or urged downwardly, distal portion 175a of distal tab 175 engages against an upper surface of tab 178a of lockout 178 and cams or urges tab 178a of lockout 178 downwardly, across a path of strap 143, supported on drive channel 140, and into distal window 180c of wedge plate 180. In this manner, if drive channel 140 is advanced distally, in the manner described above, strap 143 will abut against tab 178a of lockout 178 and prevent or block strap 143 and, in turn, drive channel 140 from moving distally. At this stage, pawl 142 is located in a dwell, distal of rack 140d, and handles 106 are arranged in a fully opened position and are thus not capable of being opened any further. In this configuration, clip applier is locked out and can no longer be used.

Depending on the size of the surgical clip, the size of components of clip applier 100 will have to be scaled accordingly. The majority of the components of the various sized clip appliers will be substantially identical to one another. Components size relating to the width of the clips, such as the jaws 120 and the wedge plate 180, or components size relating to the length of the clip, such as the pusher bar 160 and the pivot arm 179, are adjusted accordingly. In this manner, each clip applier, of varying size, will be assembled in substantially the same manner and the inner mechanism thereof will operate in substantially the same manner.

For example, clip applier 100 may be provided in a relatively small, medium and large scale, wherein each of the sizes of clip appliers stores and fires a relatively small, medium or large surgical clip. Based on the relative dimensions of the surgical clips, the corresponding clip appliers, and their corresponding components, must be scaled appropriately. However, in accordance with the present disclosure, each of the various sized clip appliers comprise the same component and may be assembled in the same sequence as one another. In this manner, a technician assembling the clip appliers will only have to learn the sequence and/or steps required for the assembly of one of the sizes of clip appliers and, in turn, be able to assemble the other sizes of clip appliers equally, without having to learn a new sequence or step of assembly.

Accordingly, the assembly method and/or steps for a relatively small, medium or large clip applier are substantially identical to one another.

Many other remaining components or parts are identical or have minor variations in feature size or scale. However, if desired, the shapes of the following parts may be modified in order to achieve the same result, namely, the length of proximal linkage member 154, the length of pivoting drive arm 156, and/or the length of distal linkage member 158.

It is contemplated that varying the starting angle of angle "α," for example, at about 45° versus at about 60°, is more effective, such that the angle difference creates a smoother starting action for the working stroke of clip applier 100. However, when starting angle "α" is about 45°, more area is taken up within housing 104 of clip applier 100 due to longer proximal and distal linkage members 154 and 158 than when the starting angle "α" is about 60°. All parameters of the motion multiplier system 155 can and should be individually designed for any configuration need in the specific device in which the motion multiplier system is considered to be implemented within.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

The invention claimed is:

1. A surgical clip applier for applying surgical clips to body tissue, the surgical clip applier comprising:
   a housing;
   at least one handle pivotably connected to the housing;
   a channel assembly extending distally from the housing;
   a clip carrier disposed within the channel assembly and defining a channel and a plurality of windows therein;
   a plurality of clips slidably disposed within the channel of the clip carrier;
   a drive channel reciprocally disposed within at least one of the housing and the channel assembly, the drive channel having a first end operatively connected to the at least one handle and a second end operatively connected to a distal end of the channel assembly;
   a wedge plate reciprocally disposed within the channel assembly, the wedge plate being operatively connected to the at least one handle and including a plurality of apertures formed along a length thereof;
   a pusher bar reciprocally positioned within the housing and the channel assembly, the pusher bar having a proximal end operatively connected to at least one handle and a distal end defining a pusher, wherein the distal end of the pusher bar is configured for engagement with a distal-most clip of the plurality of clips; and
   a motion multiplier system having a plurality of linkage members configured to distally move the pusher bar by an incremental amount upon an initial actuation of the handles, and configured to proximally move the pusher bar and the wedge plate subsequent to the initial actuation of the handles; wherein the plurality of linkages of the motion multipliers system includes:
   a proximal linkage member pivotally supported in the housing and operatively connected to the drive channel, wherein the proximal linkage member is configured to receive a fixed rod therethrough such that a pivotable connection between the proximal linkage member and the housing is established;
   a pivoting drive arm interconnecting the drive channel and the proximal linkage member; and
   a distal linkage member interconnecting the proximal linkage member the pusher bar;
   wherein a distal translation of the drive channel causes the proximal linkage member to pivotally rotate via the pivoting drive arm, such that proximal linkage member causes a first end of the distal linkage member to pivotally rotate in a first direction and a second end to slidably move the pusher bar in a distal direction.

2. The clip applier according to claim 1, wherein a further distal translation of the drive channel cause the proximal linkage member to pivotally rotate via the pivoting drive arm, such that the proximal linkage member causes the first end of the distal linkage member to pivotally rotate in a second direction and the second end to slidably move the pusher bar in a proximal direction.

3. The clip applier according to claim 1,
   wherein a distal translation of the drive channel causes a pivotal rotation of the proximal linkage member via the pivoting drive arm, wherein the pivotal rotation of the proximal linkage member causes a pivotal rotation of the distal linkage member, and wherein the pivotal rotation of the distal linkage member causes a distal translation of the pusher bar.

4. The clip applier according to claim 3, wherein a further distal translation of the drive channel causes a further pivotal rotation of the proximal linkage member via the pivoting drive arm, wherein the further pivotal rotation of the proximal linkage member causes a further pivotal rotation of the distal linkage member, and wherein the further pivotal rotation of the distal linkage member causes a proximal translation of the pusher bar.

5. The clip applier according to claim 3, wherein when the proximal linkage member, the distal linkage member, the pivoting drive arm, the drive channel and the pusher bar are in a first position, the proximal linkage member and the distal linkage member define a first angle, wherein proximal translation of the drive channel causes the proximal linkage member and the distal linkage member, via the pivoting drive arm, to pivotally rotate thereby increasing the first angle to a second angle of about 180 degrees such that the proximal linkage member and the distal linkage member are linear to each other, such that the proximal linkage member, the distal linkage member, the pivoting drive arm, the drive channel and the pusher bar are in a second position.

6. The clip applier according to claim 5, wherein when the proximal linkage member, the distal linkage member, the pivoting drive arm, the drive channel and the pusher bar are in the second position, further proximal translation of the drive channel causes the proximal linkage member and the distal linkage member, via the pivoting drive arm, to pivotally rotate thereby decreasing the second angle of about 180 degrees to a third angle, such that the distal linkage member, the pivoting drive arm, and the drive channel are in a third position, while the pusher bar is in the first position.

7. The clip applier according to claim 3, wherein the rotation of the proximal linkage member via the pivoting drive arm causes the proximal linkage member and the distal linkage member to be linear to each other and along a longitudinal axis defined by a reference axis between the proximal end of the proximal linkage member and the distal end of the distal linkage member, such that the distal linkage member causes a distal translation of the pusher bar.

8. The clip applier according to claim 7, wherein further rotation of the proximal linkage member via the pivoting drive arm causes the proximal member and the distal linkage member to be angularly offset from each other, such that the distal linkage member causes a proximal translation of the pusher bar.

9. The clip applier according to claim 3, wherein a longitudinal axis, defined by a reference axis between the proximal end of the proximal linkage member and the distal end of the distal linkage member, and the proximal linkage member define a first acute angle on a first side of the longitudinal axis, and the pusher bar is in a proximal position, wherein distal translation of the drive channel causes the proximal linkage member and the distal linkage member to pivot such that the first acute angle on the first side of the longitudinal axis increases until the proximal linkage member and the distal linkage member are linear to each other and the pusher bar has been distally translated via the distal linkage member to a distal position.

10. The clip applier according to claim 9, wherein further distal translation of the drive channel causes the proximal linkage member and the distal linkage member to pivot from the side of the longitudinal axis to a second side of the longitudinal axis such that the proximal linkage member and the longitudinal axis define a second acute angle and the pusher bar has been proximally translated via the distal linkage member to a proximal position.

11. The clip applier according to claim 1, wherein the clip follower is configured to engage the wedge plate and move distally upon distal translation of the wedge plate, and is configured to engage the clip carrier and stop proximal movement thereof upon proximal translation of the wedge plate.

12. The clip applier according to claim 1, further comprising a jaw assembly including a pair of jaws extending from an end of the channel assembly, opposite the housing, the jaw assembly adapted to accommodate a clip of the plurality of clips therein and being operable to effect formation of the clip in response to movement of the handles.

13. The clip applier according to claim 12, wherein the pusher bar is movable towards the jaws as the handles are approximated in a first direction by an initial amount in order to move a distal-most clip between the jaws, and the pusher bar being configured and adapted to move towards the housing as the handles are approximated an additional amount in the first direction to move the pusher behind a distal-most clip in the plurality of clips.

14. The clip applier according to claim 13, wherein the drive channel is configured and dimensioned to at least partially surround the jaws and the wedge plate, wherein the drive channel includes a strap extending across a distal end thereof for maintaining the jaws and the wedge plate within the drive channel.

15. The clip applier according to claim 13, wherein the drive channel is moved towards the jaw assembly as the at least one handle is moved actuated in a first direction to move the second end of the drive channel against the jaws to close the jaws, the drive channel being moved away from the jaws as the at least one handle is moved a second amount to move the second end of the drive channel away from the jaws to allow the jaws to open.

16. The clip applier according to claim 15, further comprising a motion reversing mechanism operatively connected to the wedge plate and the drive channel, wherein rotation of the motion reversing mechanism, during distal movement of the drive channel, results in proximal movement of the wedge plate.

17. The clip applier according to claim 1, further comprising:
a clip follower slidably disposed within the channel of the clip carrier and disposed proximally of the plurality of clips, the clip follower being configured and adapted for selective engagement with the windows of the clip carrier and the apertures of the wedge plate, wherein the clip follower is configured and adapted to urge the plurality of clips, in a distal direction relative to the clip carrier, upon reciprocal movement of the wedge plate.

18. The clip applier according to claim 1, further comprising:
a motion reversing mechanism operatively connected to the drive channel and the wedge plate and selectively engageable with the pusher bar, wherein rotation of the motion reversing mechanism, during the distal translation of the drive channel, results in proximal movement of the wedge plate and the pusher bar.

* * * * *